(12) United States Patent
David et al.

(10) Patent No.: US 11,465,998 B2
(45) Date of Patent: Oct. 11, 2022

(54) THERAPEUTIC COMPOUNDS AND METHODS OF USE THEREOF

(71) Applicant: Regents of the University of Minnesota, Minneapolis, MN (US)

(72) Inventors: Sunil A. David, Minneapolis, MN (US); Janardhan Banothu, Minneapolis, MN (US); Michael Brush, Minneapolis, MN (US); Collin Gustafson, Minneapolis, MN (US); Kathryn Trautman, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/856,588

(22) Filed: Apr. 23, 2020

(65) Prior Publication Data

US 2020/0339555 A1 Oct. 29, 2020

Related U.S. Application Data

(60) Provisional application No. 62/838,784, filed on Apr. 25, 2019.

(51) Int. Cl.
| | |
|---|---|
| *C07D 413/14* | (2006.01) |
| *C07D 409/04* | (2006.01) |
| *C07D 409/14* | (2006.01) |
| *C07D 417/04* | (2006.01) |
| *C07D 471/04* | (2006.01) |
| *C07D 413/04* | (2006.01) |
| *A61K 39/39* | (2006.01) |

(52) U.S. Cl.
CPC ............ *C07D 413/14* (2013.01); *A61K 39/39* (2013.01); *C07D 409/04* (2013.01); *C07D 409/14* (2013.01); *C07D 413/04* (2013.01); *C07D 417/04* (2013.01); *C07D 471/04* (2013.01)

(58) Field of Classification Search
None
See application file for complete search history.

(56) References Cited

U.S. PATENT DOCUMENTS 6,162,804 A  12/2000 Bilodeau et al.

FOREIGN PATENT DOCUMENTS

| WO | 1999016755 A1 | 4/1999 |
|---|---|---|
| WO | 2000012089 A1 | 3/2000 |
| WO | 2004000817 A2 | 12/2003 |
| WO | 2009137081 A2 | 11/2009 |
| WO | 2012044537 A1 | 4/2012 |
| WO | 2015120543 A1 | 8/2015 |

OTHER PUBLICATIONS

Database Registry Chemical Abstracts Service, Columbus, Ohio, Accession No. RN 1269038-33-6, Entered STN: Mar. 21, 2011.*
Database Registry Chemical Abstracts Service, Columbus, Ohio, Accession No. RN 2150993-56-7, Entered STN: Dec. 4, 2017.*
Database Registry Chemical Abstracts Service, Columbus, Ohio, Accession No. RN 1199589-76-8, Entered STN: Dec. 30, 2009.*
Database Registry Chemical Abstracts Service, Columbus, Ohio, Accession No. RN 1098997-99-9, Entered STN: Feb. 1, 2009.*
Al-Saleh, B , et al., "N-Azolylmethyl Ketones as Building Blocks in Heterocyclic Synthesis: Synthesis of New Polyfunctionally Substituted Azolylarylazophenols, Azolylpyridones and Azolylthiophenes", J. Heterocyclic Chem. 40, 171-175 (2003).
Ferreira De Freitas, R , et al., "Identification and Structure—Activity Relationship of HDAC6 Zinc-Finger Ubiquitin Binding Domain Inhibitors", J. Med Chem. 61, 4517-4527 (2018).
Huang, A , et al., "Discovery of the Selective CYP17A1 Lyase Inhibitor BMS-351 for the Treatment of Prostate Dancer", ACS Med Chem Lett 7, 40-45 (2016).
Mahboobi, S , et al., "[4-(Imidazol-1-yl)thiazol-2-yl]phenylamines. A Novel Class of Highly Potent Colchicine Site Binding Tubulin Inhibitors: Synthesis and Cytotoxic Activity on Selected Human Cancer Cell Lines", J Med Chem 49, 5769-5776 (2006).
Xu, R , et al., "Synthesis and evaluation of novel thiazole-based derivatives as selective inhibitors of DNA-binding domain of the androgen receptor", Chem Biol Drug Des 91,172-180 (2018).

* cited by examiner

*Primary Examiner* — Samantha L Shterengarts
(74) *Attorney, Agent, or Firm* — Viksnins Harris Padys Malen LLP

(57) ABSTRACT

The invention provides a compound of formula I:

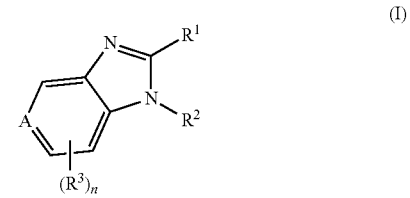

or a salt thereof, wherein $R^1$, $R^2$, $R^3$, A and n have any of the values described in the specification, as well as compositions comprising a compound of formula I, and methods of preparing and use thereof. The compounds are useful as vaccine adjuvant potentiators.

13 Claims, 13 Drawing Sheets

THERAPEUTIC COMPOUNDS AND METHODS OF USE THEREOF

CROSS REFERENCE TO RELATED APPLICATIONS

This non-provisional application claims the benefit of priority to U.S. provisional Application 62/838,784, filed 25 Apr. 2019, which is incorporated by reference in entirety.

STATEMENT REGARDING FEDERALLY SPONSORED RESEARCH

This invention was made with government support under HHSN272201400056C awarded by National Institutes of Health. The government has certain rights in the invention.

BACKGROUND

Efforts on the discovery of vaccine adjuvants have led to the examination of structure-activity relationships in a variety of innate immune stimuli, including small molecule agonists of Toll-like receptors (TLRs) such as TLR2 (Wu, W. et al. *J. Med. Chem.* 2010, 53, 3198-3213; Agnihotri, G. et al. *J. Med. Chem.* 2011, 54, 8148-8160; Salunke, D. B. et al. *J. Med. Chem.* 2013; Salunke, D. B. et al. *J. Med. Chem.* 2012, 55, 3353-3363 and Salyer, A. C. et al. *PloS one* 2016, 11, e0149848), TLR7 (Nuhn, L. et al. *Proceedings of the National Academy of Sciences of the United States of America* 2016, 113, 8098-8103; Ganapathi, L. et al. *PloS one* 2015, 10, e0134640; Hood, J. D. et al. *Human Vaccines* 2010, 6, 1-14; Shukla, N. M. et al. *Bioorg. Med. Chem. Lett.* 2009, 19, 2211-2214; Shukla, N. M. et al. *Bioorg. Med. Chem. Lett.* 2011, 21, 3232-3236; Shukla, N. M. et al. *J. Med. Chem.* 2010, 53, 4450-4465; Shukla, N. M. et al. *J. Med. Chem.* 2012, 55, 1106-1116; Shukla, N. M. et al. *Bioorg. Med. Chem. Lett.* 2010, 20, 6384-6386; Shukla, N. M. et al. *PloS one* 2012, 7, e43612; Yoo, E. et al. *Organic & biomolecular chemistry* 2013, 11, 6526-6545 and Yoo, E. et al. *J. Med. Chem.* 2014, 57, 7955-7970), TLR8 (Yoo, E. et al. *J. Med. Chem.* 2014, 57, 7955-7970; Kokatla, H. P. et al. *Organic & biomolecular chemistry* 2013, 11, 1179-1198; Salunke, D. B.; Yoo, E. et al. *J. Med. Chem.* 2012, 55, 8137-8151; Kokatla, H. P. et al. *J. Med. Chem.* 2013, 56, 6871-6885; Kokatla, H. P. et al. *Chem Med Chem* 2014, 9, 719-723; Beesu, M. et al. *J. Med. Chem.* 2016, 59, 8082-8093; Beesu, M. et al. *J. Med. Chem.* 2014, 57, 7325-7341; Beesu, M. et al. *J. Med. Chem.* 2015, 58, 7833-7849 and Beesu, M. et al. *J. Med. Chem.* 2016, 59, 3311-3330), NOD1 (Agnihotri, G. et al. *J. Med. Chem.* 2011, 54, 1490-1510), as well as C—C chemokine receptor type 1 (CCR1) (Ukani, R. et al. *Bioorg. Med. Chem. Lett.* 2012, 22, 293-295). Crystal structures of several TLRs (Zhang, Z. et al. *FEBS letters* 2017, 591, 3167-3181; Shimizu, T. *Current opinion in structural biology* 2017, 47, 52-59 and Botos, I. et al. *Structure* (London, England: 1993) 2011, 19, 447-459) confirm a common structural motif in the TLRs: these are type I integral membrane receptors containing an N-terminal extracellular leucine-rich repeat (LRR) domain, a transmembrane domain, and a C-terminal cytoplasmic domain. Ligand recognition occurs via the LRR domain (Narayanan, K. B. et al. *Apoptosis: an international journal on programmed cell death* 2015, 20, 196-209 and Leonard, J. N. et al. *Methods in molecular biology* (Clifton, N.J.) 2009, 517, 55-67), while the cytoplasmic domain known as the Toll/IL-1 receptor (TIR) region activates downstream signaling cascades by interacting with adaptor proteins such as MyD88, Mal, TRIF, and TRAM (Narayanan, K. B. et al. *Apoptosis: an international journal on programmed cell death* 2015, 20, 196-209; Watters, T. M. et al. *Immunology and cell biology* 2007, 85, 411-419; Miyake, K. et al. *International immunology* 2018, 30, 43-51 and Brikos, C. et al. *Handbook of experimental pharmacology* 2008, 21-50). The crystal structures also emphasize that ligand-induced dimerization, and the consequent apposition of the C-terminal regions of the two TLR protomers is the common mechanism of activation of TLRs (Zhang, Z. et al. *FEBS letters* 2017, 591, 3167-3181 and Song, D. H. et al. *Immunological reviews* 2012, 250, 216-229).

The ubiquitous presence of the 24-residue LRR motif in all of the TLRs (Botos, I et al. *Structure* (London, England: 1993) 2011, 19, 447-459 and Leonard, J. N. et al. *Methods in molecular biology* (Clifton, N.J.) 2009, 517, 55-67) suggests the possibility that small-molecule agonists may engage innate immune receptors such as TLR3 and TLR9 for which only canonical nucleic acid agonists are currently known. A high-throughput screen (HTS) utilized a multiplexed Poly-TLR/NLR readout (Salyer, A. C. et al. *PloS one* 2016, 11, e0149848), to examine cytokine (TNF-α/IL-1β) and interferon (IFN-α/β and IFN-γ) induction in porcine whole blood.

Currently there is a need for exploring the biological effects of NOD2-active compounds as agonists of TLRs and NLRs, including identifying novel, non-canonical immunostimulatory small molecules for innate immune receptors.

SUMMARY

In one aspect the present invention provides compounds having NOD2-agonistic activity that are useful as vaccine adjuvant potentiators.

Accordingly the invention provides a compound of formula I:

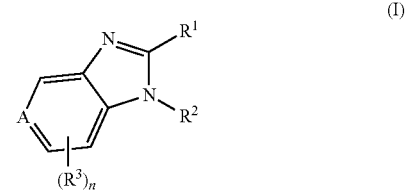

or a salt thereof, wherein:

$R^1$ is selected from the group consisting of H, $C_1$-$C_{20}$ alkyl, and $C_2$-$C_{20}$ alkenyl, where;

$R^2$ is phenyl or a 5-6 membered ring heteroaryl, where phenyl or 5-6 membered ring heteroaryl is substituted with one or more groups independently selected from the group consisting of F, Cl, —CN, $C_1$-$C_{12}$ alkyl, $C_2$-$C_{12}$ alkenyl, —($C_1$-$C_6$ alkyl)-$NR^aR^b$, —C(=NH)NH(OH), —C(=NH)NH$_2$, —C(=O)$NR^aR^b$, —C(=O)$NR^a$—$NR^aR^b$, —C(=O)NH($C_1$-$C_6$ alkyl)-$NR^aR^b$, —C(=O)$OR^a$, —$NR^aR^b$, —NO$_2$, —$OR^a$, —OC(=O)$R^a$, —$SR^a$, —S(O)$R^a$, —S(O)$_2R^a$, —S(O)$_2NR^a$, and —S(O)$_3$H;

each $R^3$ is independently selected from the group consisting of F, Cl, —CN, —$NR^aR^b$, —NO$_2$, —$OR^a$, and —($C_1$-$C_6$ alkyl)-$NR^aR^b$;

A is $CR^4$ or N, where $R^4$ is selected from H, F, Cl, —CN, —$NR^aR^b$, —NO$_2$, —$OR^a$, and —($C_1$-$C_6$ alkyl)-$NR^aR^b$;

$R^a$ and $R^b$ are independently selected from H, OH, phenyl, benzyl, 5-6 membered ring, and $C_1$-$C_6$ alkyl, where phenyl, benzyl or 5-6 membered ring is optionally substituted with one or more groups independently selected from the group consisting of F, Cl, —CN, $C_1$-$C_{12}$ alkyl, $C_2$-$C_{12}$ alkenyl, —($C_1$-$C_6$ alkyl)-$NR^aR^b$, —C(=NH)NH(OH), —C(=NH) $NH_2$, —C(=O)$NR^aR^b$, —C(=O)$NR^a$—$NR^aR^b$, —C(=O) NH($C_1$-$C_6$ alkyl)-$NR^aR^b$, —C(=O)$OR^a$, —$NR^aR^b$, —$NO_2$, —$OR^a$, —OC(=O)$R^a$, —$SR^a$, —S(O)$R^a$, —S(O)$_2R^a$, —S(O)$_2NR^a$, and —S(O)$_3$H;

each alkyl and alkenyl are optionally and independently substituted with one or more groups independently selected from the group consisting of F, Cl, —CN, —$NR^aR^b$, —$NO_2$, and —$OR^a$, —OC(=O)$R^a$, —$SR^a$, —S(O)$R^a$, —S(O)$_2R^a$, —S(O)$_2NR^a$, and —S(O)$_3$H; or $R^a$ and $R^b$ are taken together to form a 4-6 membered ring heterocycle with N;

n is 0, 1, 2, 3.

The invention also provides a pharmaceutical composition comprising a compound, or a pharmaceutically acceptable salt thereof, and a pharmaceutically acceptable excipient.

The invention also provides a compound of formula I, wherein stimulating the immune system in the animal comprises regulating the secretion of cytokines or chemokines in human blood, activating the nucleotide-binding oligomerization domain 2 (NOD2) receptor, or activating the Toll-like receptor (TLR7/8) receptor.

The invention also provides a method for stimulating immune activity in an animal comprising administering a compound of formula I, or a pharmaceutically acceptable salt thereof, to the animal.

The invention also provides a compound of formula I, or a pharmaceutically acceptable salt thereof, for use in medical therapy.

The invention also provides a compound of formula I, or a pharmaceutically acceptable salt thereof, for stimulating immune activity.

The invention also provides a compound of formula I, or a pharmaceutically acceptable salt thereof, used as vaccine adjuvant potentiators.

The invention also provides a use of a compound of formula I, or a pharmaceutically acceptable salt thereof, to prepare a medicament for stimulating immune activity in an animal.

The invention also provides processes and intermediates disclosed herein that are useful for preparing a compound of formula I or a salt thereof.

DETAILED DESCRIPTION

Figure 1:
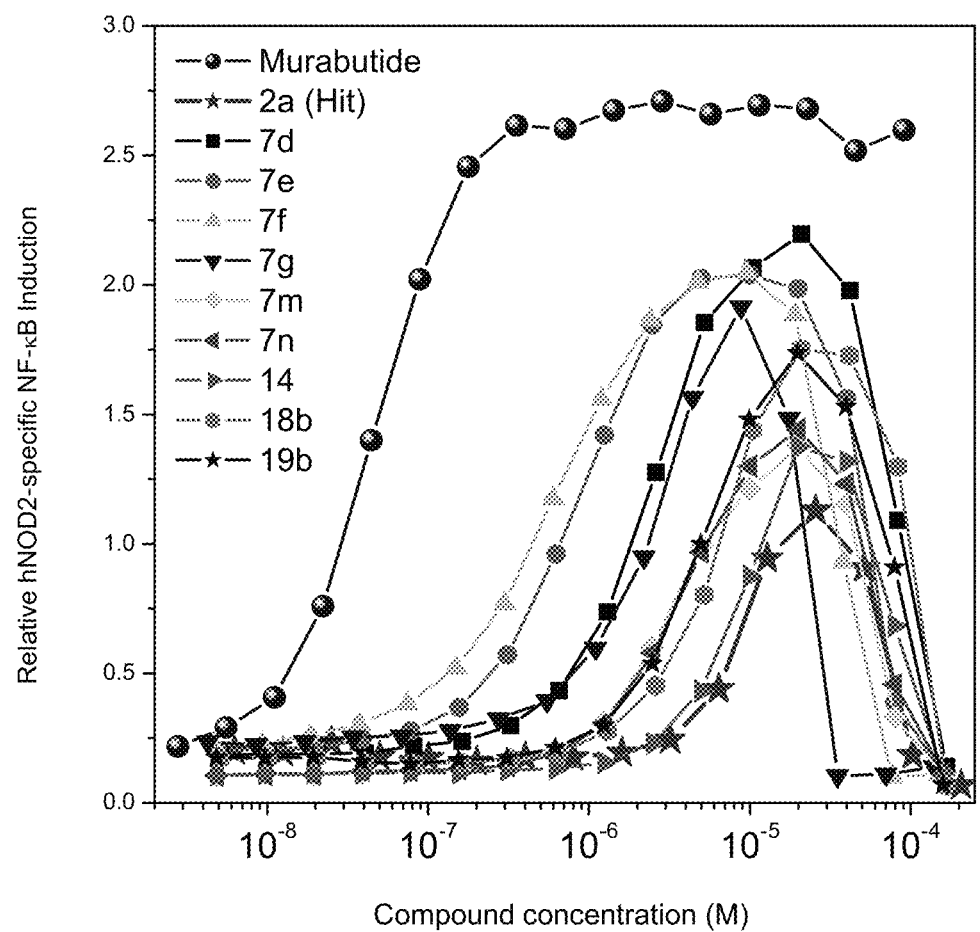
FIG. 1 shows agonistic activities of the benzimidazole thiophene carboxamide analogues (Table 1) in human NOD2 reporter gene assay. Murabutide (N-Acetyl-muramyl-LAlanyl-D-Glutamin-n-butyl-ester) was used as a canonical agonist/reference compound. Means of triplicate values are shown.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C_8$)alkyl, ($C_2$-$C_8$)alkyl, $C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, ($C_1$-$C_6$)alkyl can be methyl, ethyl, propyl, isopropyl, butyl, iso-butyl, sec-butyl, pentyl, 3-pentyl, or hexyl. The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers. Specifically, ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" refers to an unsaturated alkyl radical having one or more triple bonds. Examples of such unsaturated alkyl groups ethynyl, 1- and 3-propynyl, 3-butynyl, and higher homologs and isomers. Specifically, ($C_2$-$C_6$)

alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" refers to an alkyl groups attached to the remainder of the molecule via an oxygen atom ("oxy"). Specifically, $(C_1-C_6)$alkoxy can be methoxy, ethoxy, propoxy, isopropoxy, butoxy, iso-butoxy, sec-butoxy, pentoxy, 3-pentoxy, or hexyloxy.

The term "alkylthio" refers to an alkyl groups attached to the remainder of the molecule via a thio group. Specifically, $(C_1-C_6)$alkylthio can be methylthio, ethylthio, propylthio, isopropylthio, butylthio, isobutylthio, pentylthio, or hexylthio.

The term "cycloalkyl" refers to a saturated or partially unsaturated (non-aromatic) all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane. Specifically, $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl (or its N-oxide), pyrrolyl, pyrazinyl, pyrimidinyl (or its N-oxide), pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl (or its N-oxide), isoquinolyl (or its N-oxide), benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein. Specifically, ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl.

The term "alkanoyloxy" as used herein refers to a group (alkyl)-C(=O)—O—, wherein the term alkyl has the meaning defined herein. Specifically, ($C_2$-$C_6$)alkanoyloxy can be acetoxy, propanoyloxy, butanoyloxy, isobutanoyloxy, pentanoyloxy, or hexanoyloxy.

As used herein, the term "heteroatom" is meant to include oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethyl silyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line " $\sim$ " that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine,) followed by the removal of 1 or more atoms from the second functional group to create the open valence.

Formula (I) Compounds

From the deconvolution of hits observed in a high-throughput screen (HTS) identifying cytokine/interferon inducing compounds in porcine blood, 1-substituted-1H-benzo[d]imidazole compounds of formula I were identified and showed human NOD2-agonistic activity. Confirmatory screens and deconvolution assays using reporter gene platforms for hTLR2, hTLR3, hTLR4, hTLR5, hTLR7, hTLR8, hTLR9, hNOD1, hNOD2, and Stimulator of interferon genes (STING) led to the validation of the majority of hits (Bhat, N.; et al. *European journal of immunology* 2014, 44, 634-640; Barber, G. N. *Trends in immunology* 2014, 35, 88-93).

An embodiment of the formula I compounds is wherein R$^2$ is phenyl, substituted with one or more groups independently selected from the group consisting of F, Cl, —CN, C$_1$-C$_{12}$ alkyl, C$_2$-C$_{12}$ alkenyl, —(C$_1$-C$_6$ alkyl)-NR$^a$R$^b$, —C(=NH)NH(OH), —C(=NH)NH$_2$, —C(=O)NR$^a$R$^b$, —C(=O)OR$^a$, —NR$^a$R$^b$, —C(=O)NH(C$_1$-C$_6$ alkyl)-NR$^a$R$^b$, —NO$_2$, —OR$^a$, —OC(=O)R$^a$, —SR$^a$, —S(O)R$^a$, —S(O)$_2$R$^a$, —S(O)$_2$NR$^a$, and —S(O)$_3$H.

An embodiment of the formula I compounds is wherein R$^2$ is a 5-6 membered ring heteroaryl selected from the group consisting of pyridinyl, thiophenyl, pyrrolyl, oxazolyl and thiazolyl, wherein pyridinyl, thiophenyl, pyrrolyl, oxazolyl or thiazolyl, is substituted with one or more groups independently selected from the group consisting of F, Cl, —CN, C$_1$-C$_{12}$ alkyl, C$_2$-C$_{12}$ alkenyl, —(C$_1$-C$_6$ alkyl)-NR$^a$R$^b$, —C(=NH)NH(OH), —C(=NH)NH$_2$, —C(=O)NR$^a$R$^b$, —C(=O)OR$^a$, —NR$^a$R$^b$, —C(=O)NH(C$_1$-C$_6$ alkyl)-NR$^a$R$^b$, —NO$_2$, —OR$^a$, —OC(=O)R$^a$, —SR$^a$, —S(O)R$^a$, —S(O)$_2$R$^a$, —S(O)$_2$NR$^a$, and —S(O)$_3$H.

An embodiment of the formula I compounds is R$^2$ is thiophenyl.

Embodiments of formula I compounds have formula Ia or formula Ib:

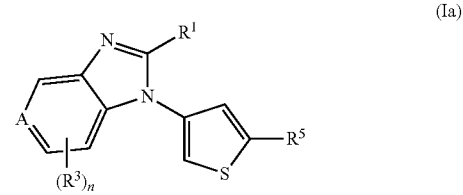

(Ia)

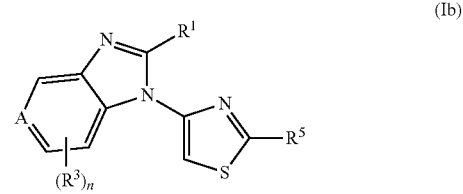

(Ib)

wherein R$^5$ is selected from the group consisting of F, Cl, —CN, C$_1$-C$_{12}$ alkyl, C$_2$-C$_{12}$ alkenyl, —(C$_1$-C$_6$ alkyl)-NR$^a$R$^b$, —C(=NH)NH(OH), —C(=NH)NH$_2$, —C(=O)NR$^a$R$^b$, —C(=O)NR$^a$—NR$^a$R$^b$, —C(=O)NH(C$_1$-C$_6$ alkyl)-NR$^a$R$^b$, —C(=O)OR$^a$, —NR$^a$R$^b$, —NO$_2$, —OR$^a$, —OC(=O)R$^a$, —SR$^a$, —S(O)R$^a$, —S(O)$_2$R$^a$, —S(O)$_2$NR$^a$, and —S(O)$_3$H.

Exemplary embodiments of formula Ia and formula Ib compounds include wherein R$^5$ is —C(=O)NR$^a$R$^b$, and R$^a$ is H and R$^b$ is phenyl, pyridinyl or benzyl; and R$^5$ is —C(=O)NH(C$_1$-C$_6$ alkyl)-NR$^a$R$^b$, and wherein R$^a$ and R$^b$ together form piperidinyl, morpholinyl or piperazinyl.

Exemplary embodiments of formula Ia and formula Ib compounds include wherein R$^5$ is —C(=O)OR$^a$, and R$^a$ is ethyl.

Exemplary embodiments of formula Ia and formula Ib compounds include wherein R$^1$ is H, methyl, ethyl, n-propyl, n-butyl, iso-pentyl, n-pentyl, n-hexyl, n-octyl, n-nonyl, n-undecyl, n-tridecyl, n-pentadecyl, n-heptadecyl or iso-pentenyl.

An embodiment of the formula I compounds is wherein A is CH.

An embodiment of the formula I compounds is wherein A is N.

An embodiment of the formula I compounds is wherein n is 0.

An embodiment of the formula I compounds is wherein $R^3$ is H.

An embodiment of the formula I compounds is wherein $R^3$ is $NH_2$.

Exemplary embodiments of formula I compounds are shown in Table 1.

A specific group of compounds are compounds of formula I wherein

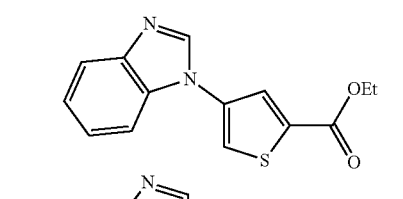

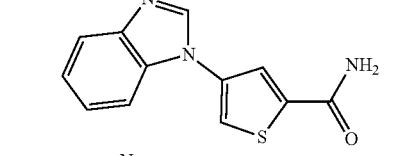

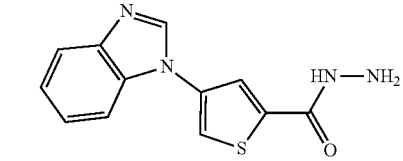

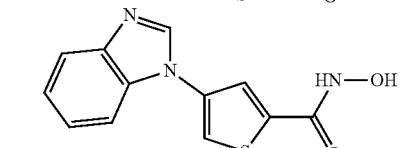

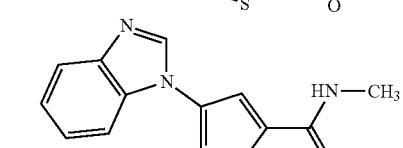

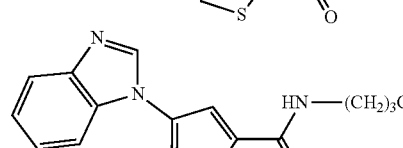

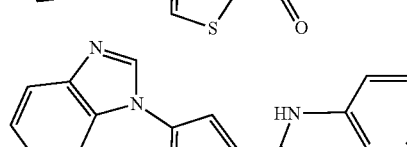

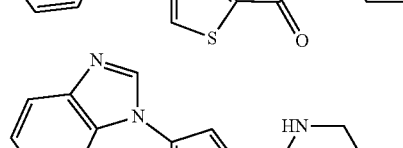

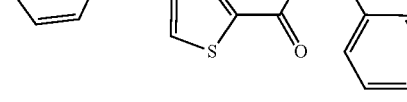

-continued

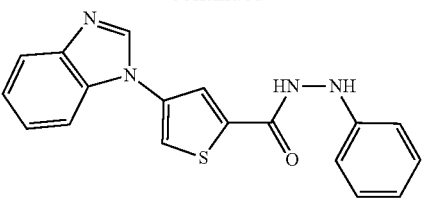

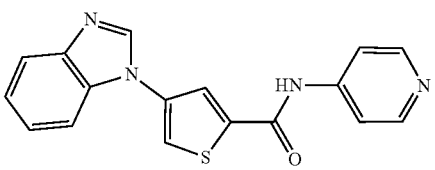

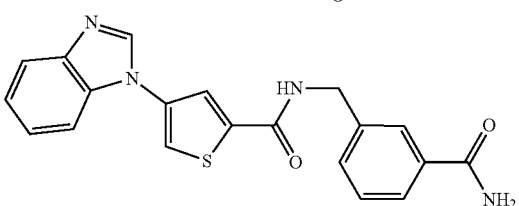

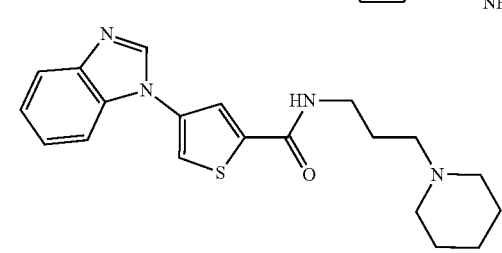

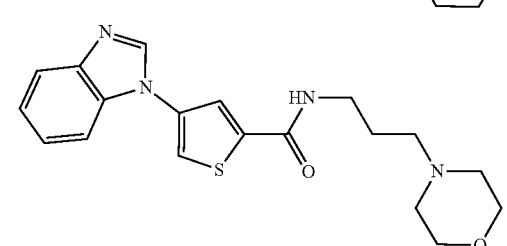

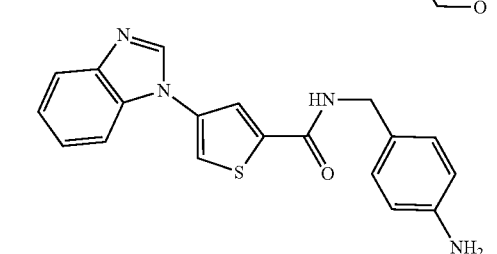

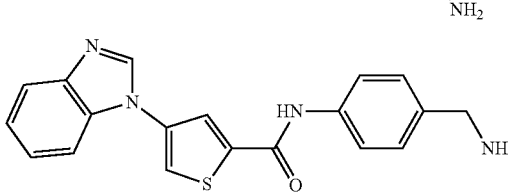

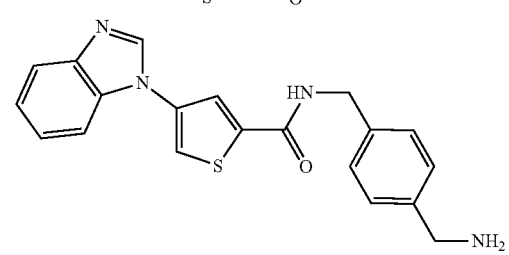

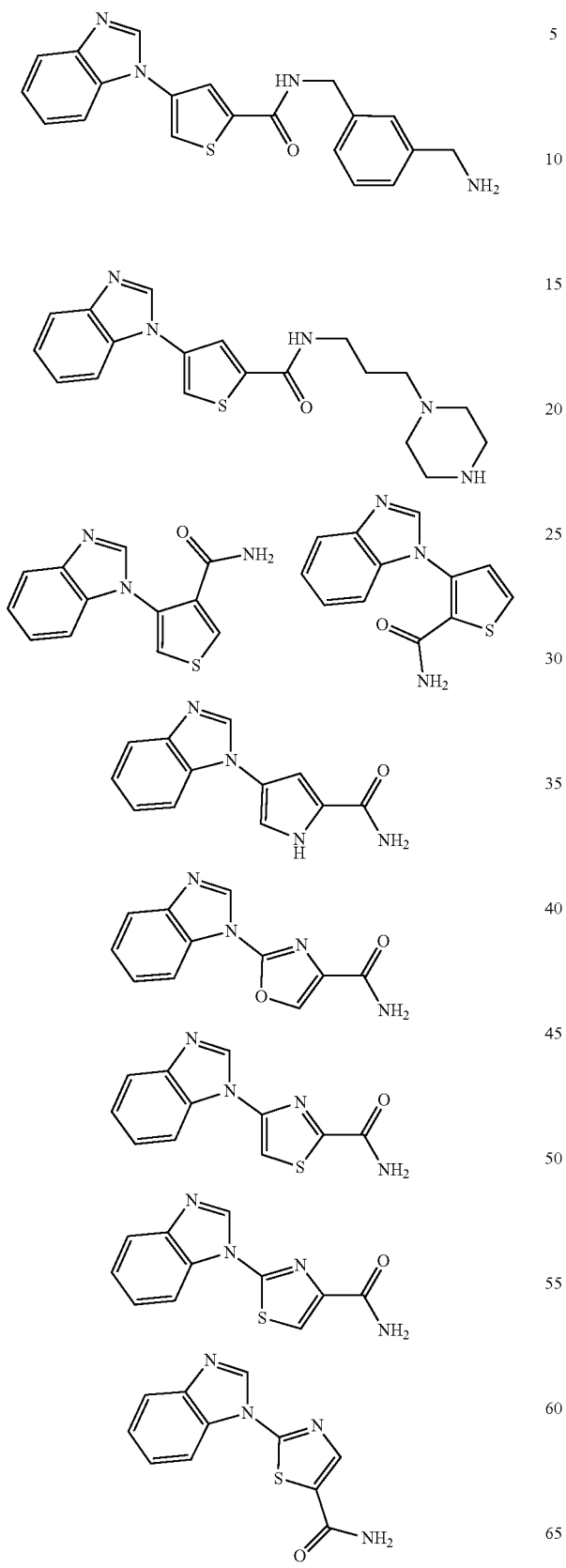
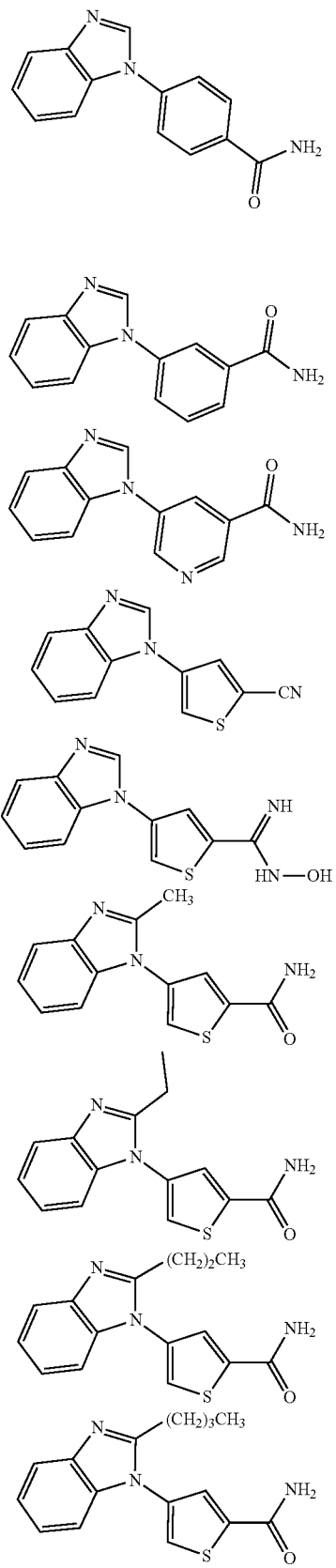

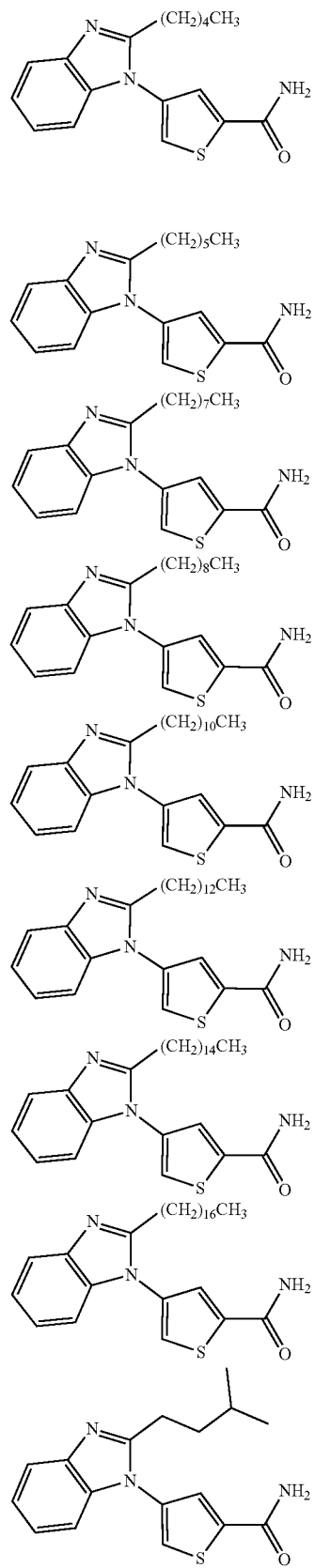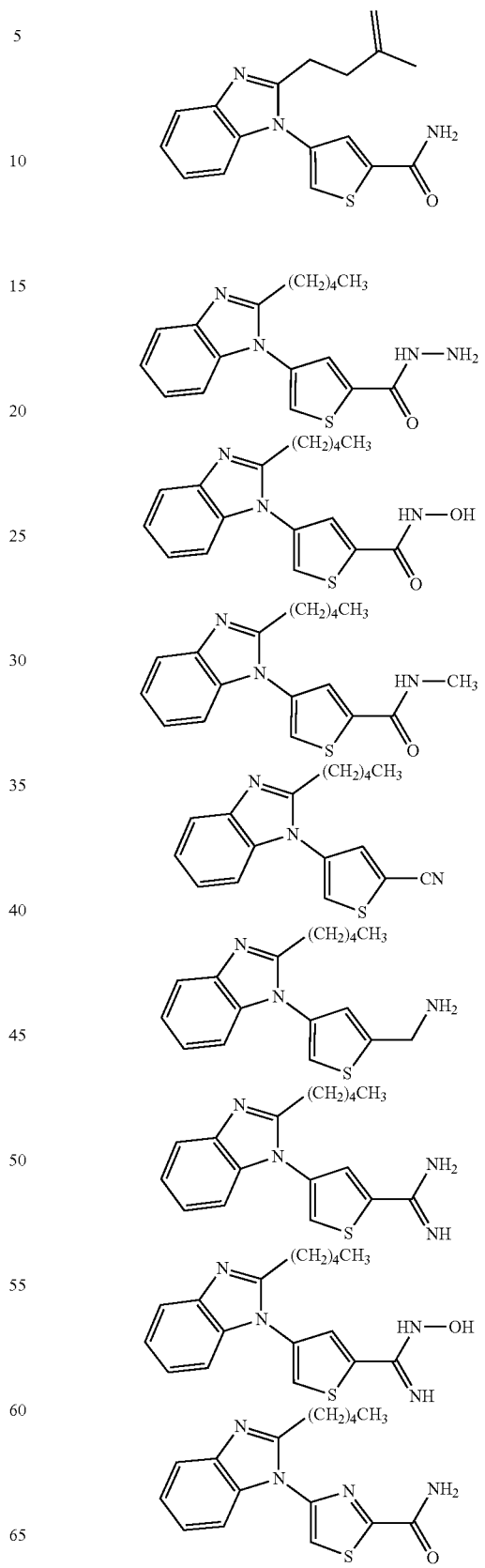

-continued

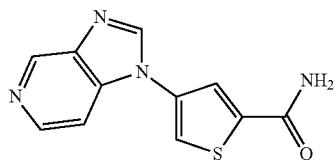

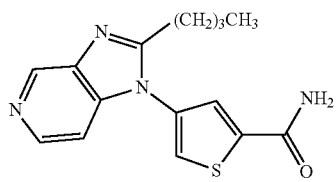

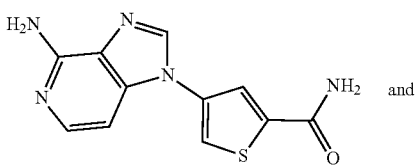 and

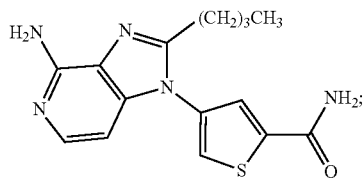

or a salt thereof.

Processes for preparing compounds of formula I are provided as further embodiments of the invention and are illustrated by the following procedures in which the meanings of the generic radicals are as given above unless otherwise qualified.

N-arylation of benzimidazole with ethyl 4-bromothiophene-2-carboxylate, followed by ammonolysis of the ester 1 yielded 2a (Example 1). Weak hNOD2-agonistic activity was confirmed (FIG. 1) versus murabutide (N-Acetyl-muramyl-LAlanyl-D-Glutamin-n-butyl-ester), a known immunomodulatory.

The hydrazides 2b, 2h, the N-hydroxy derivative 2c, the N-alkyl (2d, 2e, 2g, 2j-2m, 2o-2q) and N-aryl derivatives (2f, 2i, 2n) were all inactive (Scheme 1), pointing to the absolute requirement of an unsubstituted carboxamide, which was confirmed by the absence of NOD2 activity in the des-carboxamido analogue 3a. The regioisomeric thiophene carboxamides 3b and 3c were also inactive. Thiazole carboxamide analogues 3f, 3h, and 3i were devoid of activity, as were the pyrazole (3d), oxazole (3e), phenyl (3j, 3k) and pyridyl (3l) analogues. Homologated thiophene 2-carboxamide analogue 3g was also inactive, pointing to conformational rigidity imparted by the twisted, out-of-plane thiophene as an important determinant of activity. The obligatory presence of an unsubstituted carboxamide prompted the examination of the 2-cyanothiophene (4a) and the hydroxyamidine (4b) analogues, which were also found to be inactive. A homologous series of C2-alkyl compounds were accessed by mono-arylation of o-phenylenediamine with ethyl 4-bromothiophene-2-carboxylate, followed by a acylation-cyclization and ammonolysis of the ethyl ester to obtain the target compounds 7a-7l (Example 2). The isopentyl and isopentenyl derivatives were obtained by coupling the corresponding acid, followed by cyclization (Example 2).

A distinct bimodal effect of increasing chain length on human NOD2 agonistic potency was observed: whereas the C2-methyl (7a), ethyl (7b) and propyl (7c) compounds showed lower potency than the hit compound, progressive increases in potency were observed for the butyl-hexyl analogues (7d-7f), with the C2-pentyl (7e) and -hexyl analogues (7f) being virtually equipotent, displaying $EC_{50}$ values of 0.68 µM and 0.66 µM (relative to 7.265 µM for 2a; Table 1). A precipitous fall in potency was observed with further increases in chain length, with the tridecyl (7j) and higher homologues were inactive under the tested conditions (Table 1). The isopentyl (7m) and isopentenyl (7n) analogues showed potencies very similar to the butyl analogue (7d).

In order to examine the aromaticity of the thiophene in determining NOD2 activity, the thioether analogue 10 was constructed (Example 3). The intermediate 8 was synthesized by N-alkylation of 2-butylbenzimidazole with 2-bromoethanol, followed by conversion of the hydroxyl group to bromo using Appel conditions. S-alkylation with ethylthioglycolate and ammonolysis yielded 10, which was found to be inactive, consistent with the inactivity of the conformationally flexible homologated 3g Although the hydrazides 2b, 2h, the N-hydroxy derivative 2c, as well as N-methyl compound (2d) had previously been found to be inactive, functional groups in the C2-alkyl compounds were examined. The N-hydroxy compound 11b, as well as the N-methyl analogue 11c showed weak activity, as did the amidine 13b, perhaps pointing to the possibility that although the weakly acidic, H-bond donating carboxamide is preferred, the penalty incurred by introducing strongly basic H-bond donating groups is partially compensated for by the C2-alkyl group. This conjecture was borne out also by the observation that the C2-pentyl thiazole compound 14 is weakly active, whereas the C2-des-alkyl analogue 3f was inactive.

Analogues with the benzimidazole core replaced with imidazo[4,5-c]pyridinyl and 4-amino imidazo[4,5-c]pyridinyl moieties, with or without a C2-alkyl group were synthesized as shown in Example 4. Both the C2-butyl compounds 18b and 19b were weakly active, whereas 18a and 19a were inactive. The C2-pentyl-substituted benzologues (imidazo[4,5-c]quinolin-1-yl derivatives) 23a and 23b (Scheme 4) were inactive, suggesting that steric bulk was not tolerated at this position.

TABLE 1

EC$_{50}$ values of formula I compounds in human NOD2 specific reporter gene assays

| No. | Structure | IUPAC Name | hNOD2 Agonistic Activity (μM)$^a$ |
|---|---|---|---|
| 1 | 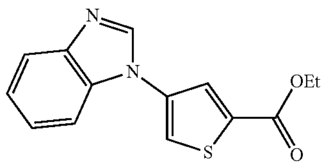 [SMILES: CCOC(=O)c1cc(-n2cnc3ccccc32)cs1] | ethyl 4-(1H-benzo[d]imidazol-1-yl)thiophene-2-carboxylate | NA* |
| 2a | 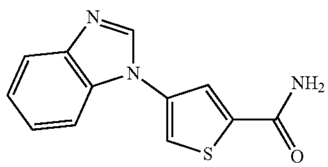 [SMILES: NC(=O)c1cc(-n2cnc3ccccc32)cs1] | 4-(1H-benzo[d]imidazol-1-yl)thiophene-2-carboxamide | 7.265 |
| 2b | 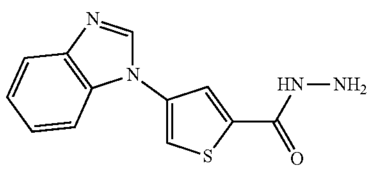 [SMILES: NNC(=O)c1cc(-n2cnc3ccccc32)cs1] | 4-(1H-benzo[d]imidazol-1-yl)thiophene-2-carbohydrazide | NA* |
| 2d | 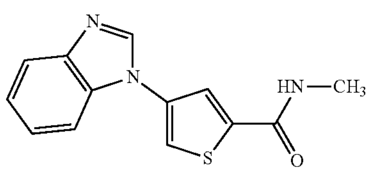 [SMILES: CNC(=O)c1cc(-n2cnc3ccccc32)cs1] | 4-(1H-benzo[d]imidazol-1-yl)-N-methylthiophene-2-carboxamide | NA* |
| 2e | 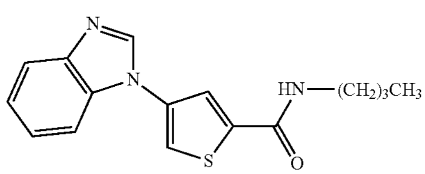 | 4-(1H-benzo[d]imidazol-1-yl)-N-butylthiophene-2-carboxamide | NA* |
| 2f | 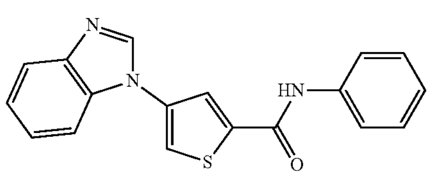 [SMILES: O=C(Nc1ccccc1)c1cc(-n2cnc3ccccc32)cs1] | 4-(1H-benzo[d]imidazol-1-yl)-N-phenylthiophene-2-carboxamide | NA* |
| 2g | 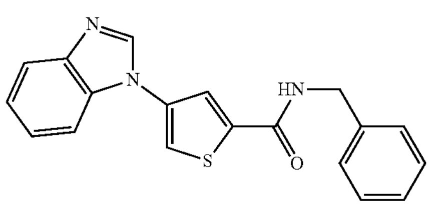 [SMILES: O=C(NCc1ccccc1)c1cc(-n2cnc3ccccc32)cs1] | 4-(1H-benzo[d]imidazol-1-yl)-N-benzylthiophene-2-carboxamide | NA* |
| 2h | 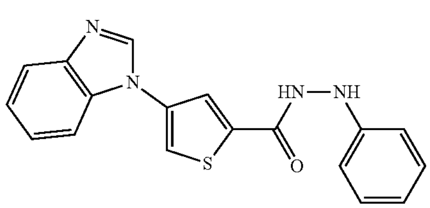 [SMILES: O=C(NNc1ccccc1)c1cc(-n2cnc3ccccc32)cs1] | 4-(1H-benzo[d]imidazol-1-yl)-N'-phenylthiophene-2-carbohydrazide | NA* |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 2i | 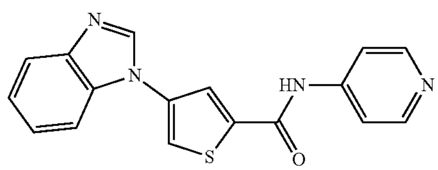 [SMILES: O=C(Nc1ccncc1)c1cc(-n2cnc3ccccc32)cs1] | 4-(1H-benzo[d]imidazol-1-yl)-N-(pyridin-4-yl)thiophene-2-carboxamide | NA* |
| 2j | 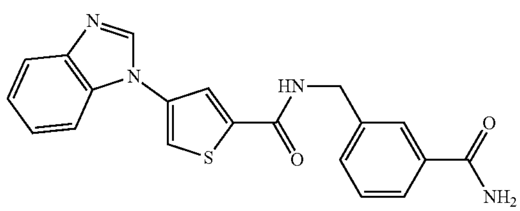 [SMILES: NC(=O)c1cccc(CNC(=O)c2cc(-n3cnc4ccccc43)cs2)c1] | 4-(1H-benzo[d]imidazol-1-yl)-N-(3-carbamoylbenzyl)thiophene-2-carboxamide | NA* |
| 2k | 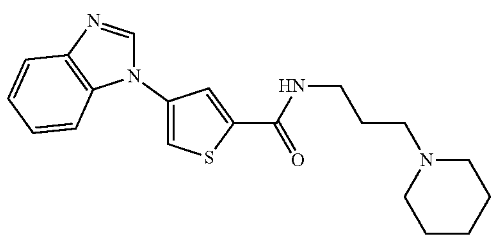 [SMILES: O=C(NCCCN1CCCCC1)c1cc(-n2cnc3ccccc32)cs1] | 4-(1H-benzo[d]imidazol-1-yl)-N-(3-(piperidin-1-yl)propyl)thiophene-2-carboxamide | NA* |
| 2l | 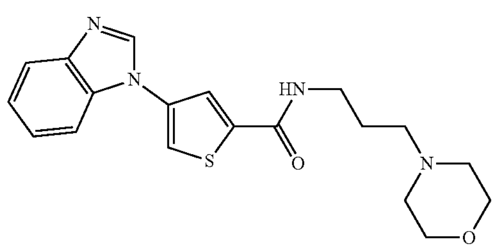 [SMILES: O=C(NCCCN1CCOCC1)c1cc(-n2cnc3ccccc32)cs1] | 4-(1H-benzo[d]imidazol-1-yl)-N-(3-morpholinopropyl)thiophene-2-carboxamide | NA* |
| 2m | 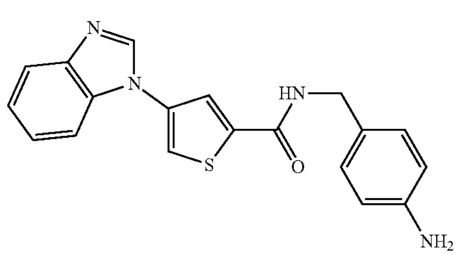 [SMILES: Nc1ccc(CNC(=O)c2cc(-n3cnc4ccccc43)cs2)cc1] | N-(4-aminobenzyl)-4-(1H-benzo[d]imidazol-1-yl)thiophene-2-carboxamide | NA* |
| 2n | 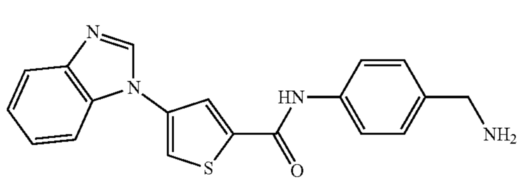 [SMILES: NCc1ccc(NC(=O)c2cc(-n3cnc4ccccc43)cs2)cc1] | N-(4-(aminomethyl)phenyl)-4-(1H-benzo[d]imidazol-1-yl)thiophene-2-carboxamide | NA* |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 2o | 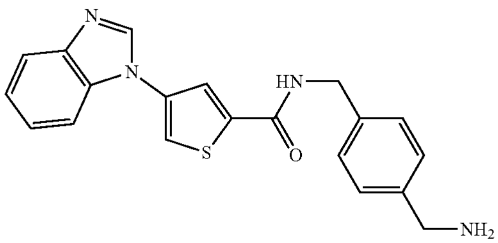 [SMILES: NCc1ccc(CNC(=O)c2cc(-n3cnc4ccccc43)cs2)cc1] | N-(4-(aminomethyl)benzyl)-4-(1H-benzo[d]imidazol-1-yl)thiophene-2-carboxamide | NA* |
| 2p | 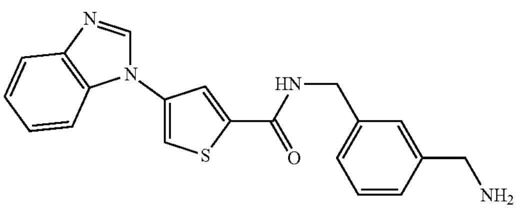 [SMILES: NCc1cccc(CNC(=O)c2cc(-n3cnc4ccccc43)cs2)c1] | N-(3-(aminomethyl)benzyl)-4-(1H-benzo[d]imidazol-1-yl)thiophene-2-carboxamide | NA* |
| 2q | 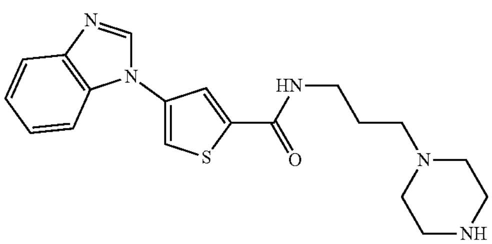 [SMILES: O=C(NCCCN1CCNCC1)c1cc(-n2cnc3ccccc32)cs1] | 4-(1H-benzo[d]imidazol-1-yl)-N-(3-(piperazin-1-yl)propyl)thiophene-2-carboxamide | NA* |
| 3b | 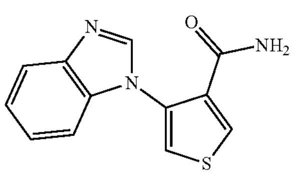 [SMILES: NC(=O)c1cscc1-n1cnc2ccccc21] | 4-(1H-benzo[d]imidazol-1-yl)thiophene-3-carboxamide | NA* |
| 3c | 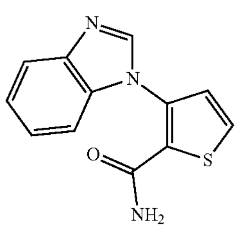 [SMILES: NC(=O)c1sccc1-n1cnc2ccccc21] | 3-(1H-benzo[d]imidazol-1-yl)thiophene-2-carboxamide | NA* |
| 3d | 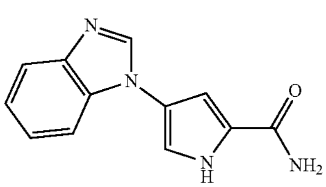 [SMILES: NC(=O)c1cc(-n2cnc3ccccc32)c[nH]1] | 4-(1H-benzo[d]imidazol-1-yl)-1H-pyrrole-2-carboxamide | NA* |
| 3e | 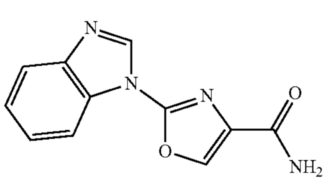 [SMILES: NC(=O)c1coc(-n2cnc3ccccc32)n1] | 2-(1H-benzo[d]imidazol-1-yl)oxazole-4-carboxamide | NA* |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 3f | 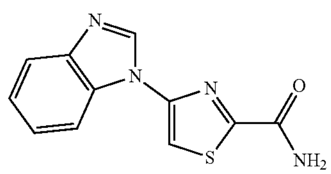 [SMILES: NC(=O)c1nc(-n2cnc3ccccc32)cs1] | 4-(1H-benzo[d]imidazol-1-yl)thiazole-2-carboxamide | NA* |
| 3h | 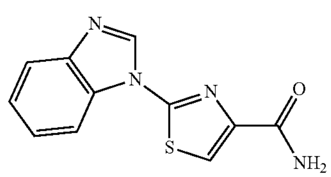 [SMILES: NC(=O)c1csc(-n2cnc3ccccc32)n1] | 2-(1H-benzo[d]imidazol-1-yl)thiazole-4-carboxamide | NA* |
| 3i | 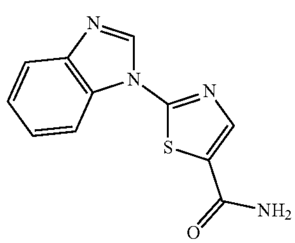 [SMILES: NC(=O)c1cnc(-n2cnc3ccccc32)s1] | 2-(1H-benzo[d]imidazol-1-yl)thiazole-5-carboxamide | NA* |
| 3j | 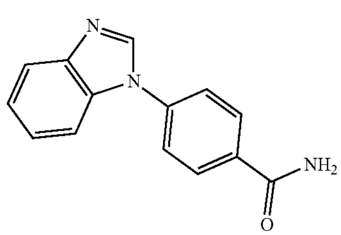 [SMILES: NC(=O)c1ccc(-n2cnc3ccccc32)cc1] | 4-(1H-benzo[d]imidazol-1-yl)benzamide | NA* |
| 3k | 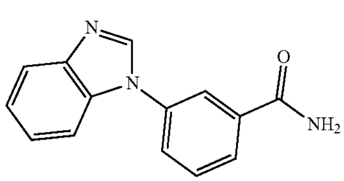 [SMILES: NC(=O)c1cccc(-n2cnc3ccccc32)c1] | 3-(1H-benzo[d]imidazol-1-yl)benzamide | NA* |
| 3l | 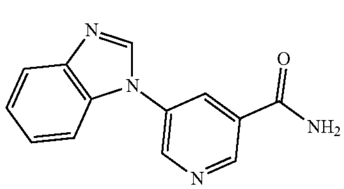 [SMILES: NC(=O)c1cncc(-n2cnc3ccccc32)c1] | 5-(1H-benzo[d]imidazol-1-yl)nicotinamide | NA* |
| 4a | 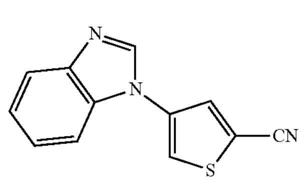 [SMILES: N#Cc1cc(-n2cnc3ccccc32)cs1] | 4-(1H-benzo[d]imidazol-1-yl)thiophene-2-carbonitrile | NA* |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 4b | 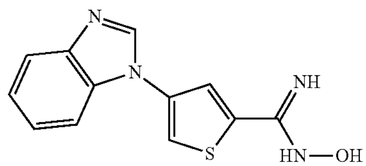 [SMILES: N=C(NO)c1cc(-n2cnc3ccccc32)cs1] | 4-(1H-benzo[d]imidazol-1-N-hydroxythiophene-2-carboximidamide | NA* |
| 7a | 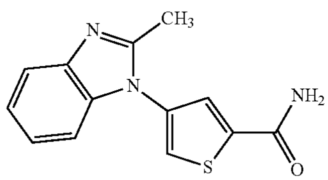 [SMILES: Cc1nc2ccccc2n1-c1csc(C(N)=O)c1] | 4-(2-methyl-1H-benzo[d]imidazol-1-yl)thiophene-2-carboxamide | 15.709 |
| 7b | 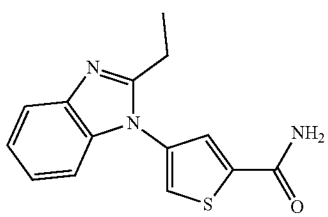 [SMILES: CCc1nc2ccccc2n1-c1csc(C(N)=O)c1] | 4-(2-ethyl-1H-benzo[d]imidazol-1-yl)thiophene-2-carboxamide | 13.196 |
| 7c | 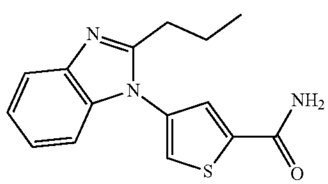 [SMILES: CCCc1nc2ccccc2n1-c1csc(C(N)=O)c1] | 4-(2-propyl-1H-benzo[d]imidazol-1-yl)thiophene-2-carboxamide | 8.263 |
| 7d | 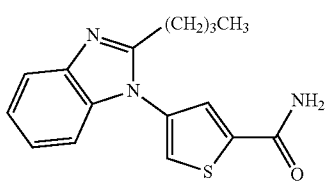 | 4-(2-butyl-1H-benzo[d]imidazol-1-yl)thiophene-2-carboxamide | 2.068 |
| 7e | 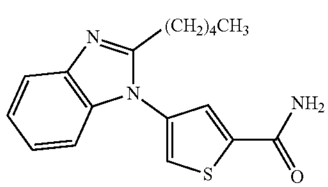 | 4-(2-pentyl-1H-benzo[d]imidazol-1-yl)thiophene-2-carboxamide | 0.684 |
| 7f | 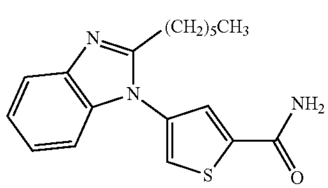 | 4-(2-hexyl-1H-benzo[d]imidazol-1-yl)thiophene-2-carboxamide | 0.664 |
| 7g | 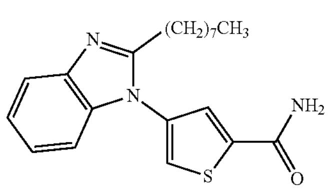 | 4-(2-octyl-1H-benzo[d]imidazol-1-yl)thiophene-2-carboxamide | 2.203 |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 7h | 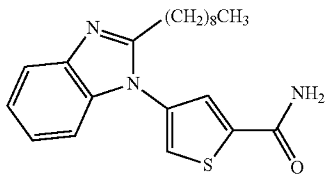 | 4-(2-nonyl-1H-benzo[d]imidazol-1-yl)thiophene-2-carboxamide | 3.056 |
| 7i | 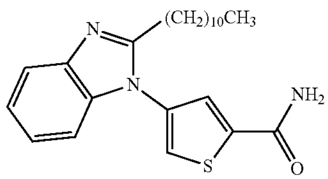 | 4-(2-undecyl-1H-benzo[d]imidazol-1-yl)thiophene-2-carboxamide | 5.811 |
| 7j | 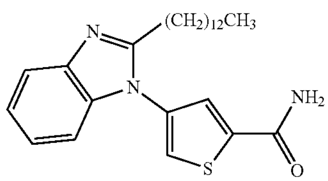 | 4-(2-tridecyl-1H-benzo[d]imidazol-1-yl)thiophene-2-carboxamide | NA* |
| 7k | 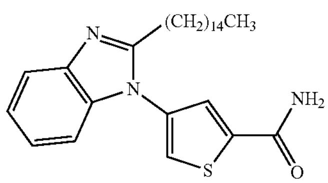 | 4-(2-pentadecyl-1H-benzo[d]imidazol-1-yl)thiophene-2-carboxamide | NA* |
| 7l | 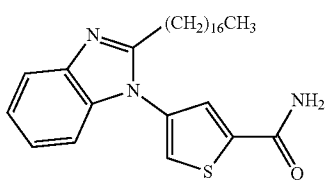 | 4-(2-heptadecyl-1H-benzo[d]imidazol-1-yl)thiophene-2-carboxamide | NA* |
| 7m | 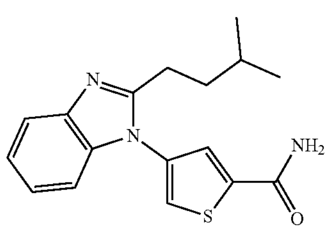 [SMILES: CC(C)CCc1nc2ccccc2n1-c1csc(C(N)=O)c1] | 4-(2-isopentyl-1H-benzo[d]imidazol-1-yl)thiophene-2-carboxamide | 2.914 |
| 7n | 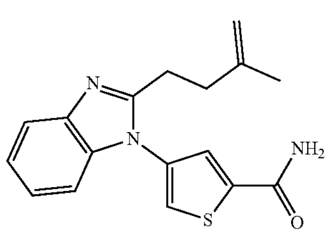 [SMILES: C=C(C)CCc1nc2ccccc2n1-c1csc(C(N)=O)c1] | 4-(2-(3-methylbut-3-en-1-yl)-1H-benzo[d]imidazol-1-yl)thiophene-2-carboxamide | 3.236 |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 11a | 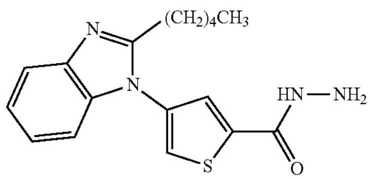 | 4-(2-pentyl-1H-benzo[d]imidazol-1-yl)thiophene-2-carbohydrazide | NA* |
| 11b | 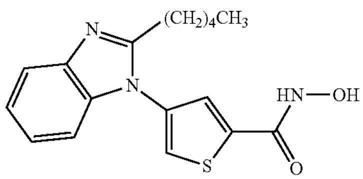 | N-hydroxy-4-(2-pentyl-1H-benzo[d]imidazol-1-yl)thiophene-2-carboxamide | 1.843 |
| 11c | 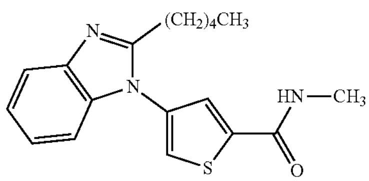 | N-methyl-4-(2-pentyl-1H-benzo[d]imidazol-1-yl)thiophene-2-carboxamide | 7.021 |
| 12 | 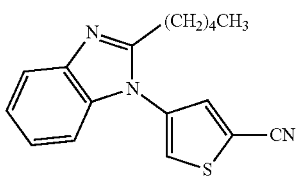 | 4-(2-pentyl-1H-benzo[d]imidazol-1-yl)thiophene-2-carbonitrile | NA* |
| 13a | 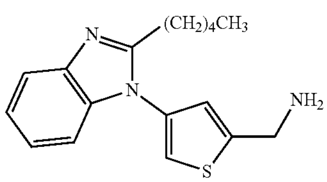 | (4-(2-pentyl-1H-benzo[d]imidazol-1-yl)thiophen-2-yl)methanamine | NA* |
| 13b | 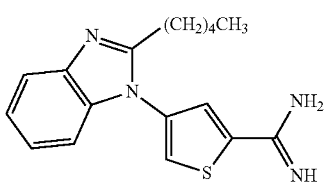 | 4-(2-pentyl-1H-benzo[d]imidazol-1-yl)thiophene-2-carboximidamide | 6.572 |
| 13c | 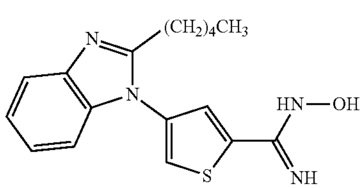 | N-hydroxy-4-(2-pentyl-1H-benzo[d]imidazol-1-yl)thiophene-2-carboximidamide | NA* |
| 14 | 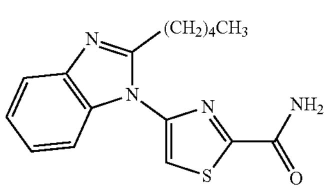 | 4-(2-pentyl-1H-benzo[d]imidazol-1-yl)thiazole-2-carboxamide | 7.395 |

TABLE 1-continued

EC$_{50}$ values of formula I compounds in human NOD2 specific reporter gene assays

| No. | Structure | IUPAC Name | hNOD2 Agonistic Activity (μM)$^a$ |
|---|---|---|---|
| 18a | 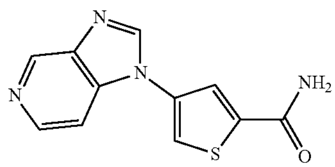 [SMILES: NC(=O)c1cc(-n2cnc3cnccc32)cs1] | 4-(1H-imidazo[4,5-c]pyridin-1-yl)thiophene-2-carboxamide | NA* |
| 18b | 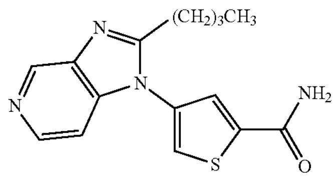 | 4-(2-butyl-1H-imidazo[4,5-c]pyridin-1-yl)thiophene-2-carboxamide | 5.647 |
| 19a | 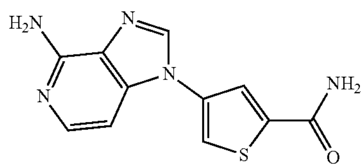 [SMILES: NC(=O)c1cc(-n2cnc3c(N)nccc32)cs1] | 4-(4-amino-1H-imidazo[4,5-c]pyridin-1-yl)thiophene-2-carboxamide | NA* |
| 19b | 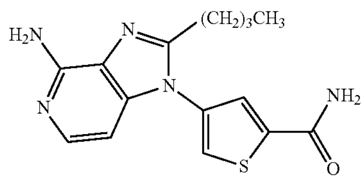 | 4-(4-amino-2-butyl-1H-imidazo[4,5-c]pyridin-1-yl)thiophene-2-carboxamide | 4.076 |

$^a$EC$_{50}$ values represent the arithmetic mean values obtained on quadruplicate samples.
NA* indicates inactive under the tested conditions.

Biological Activity of Formula I Compounds

NOD2 has been identified as a target for muramyl dipeptides (Inohara, N.; et al. *The Journal of biological chemistry* 2003, 278, 5509-5512; Girardin, S. E.; et al. *The Journal of biological chemistry* 2003, 278, 8869-8872). Cells of the monocyte/macrophage lineage are major targets (Wahl, S. M.; et al. *Journal of immunology* (Baltimore, Md.: 1950) 1979, 122, 2226-2231; Riveau, G. J.; et al. *Cellular immunology* 1991, 134, 147-156; Fevrier, M.; et al. *European journal of immunology* 1978, 8, 558-562; Ogura, Y.; et al. *J. Biol. Chem.* 2001, 276, 4812-4818) for this class of immunostimulatory compounds.

Figure 2:
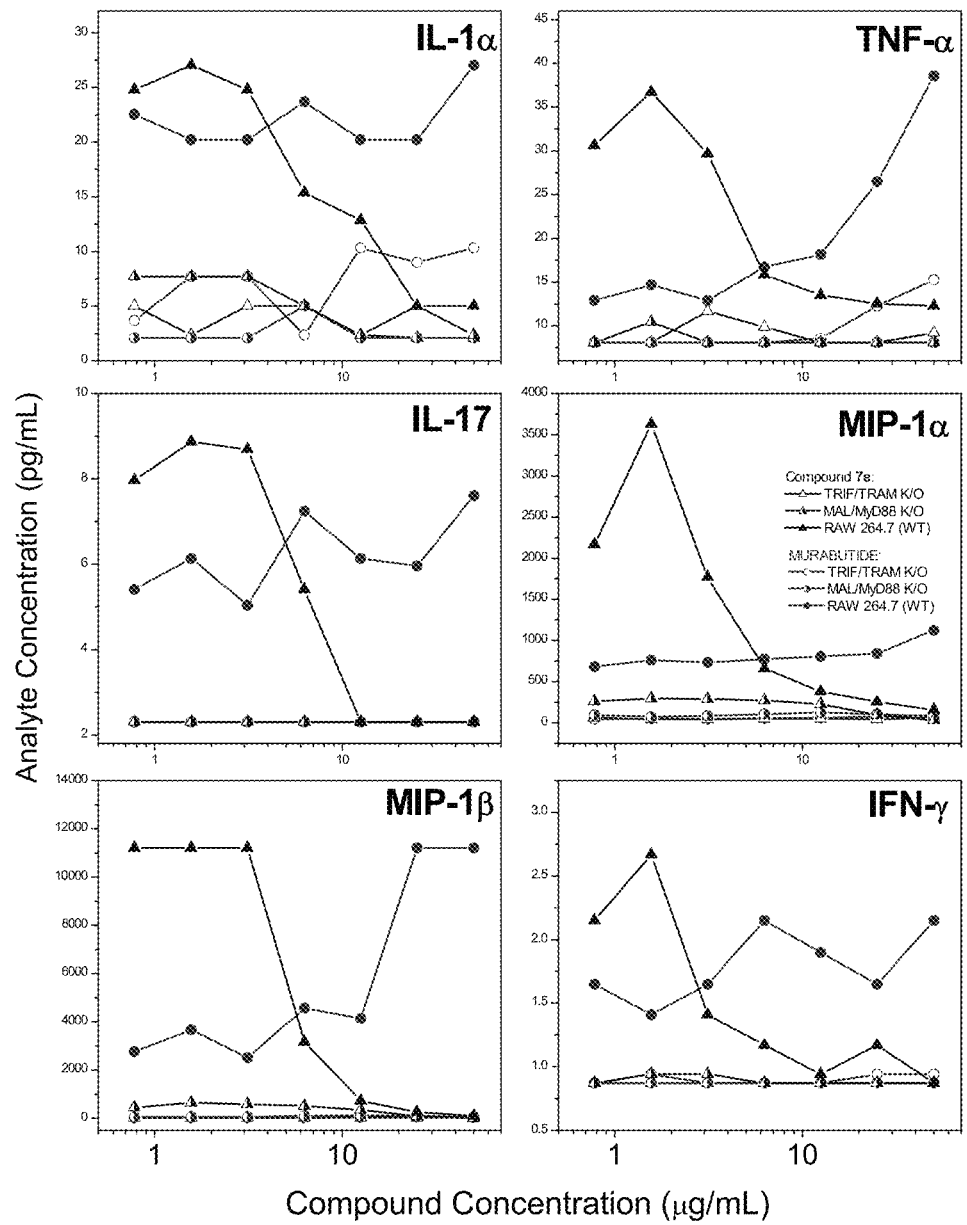
FIG. 2 shows induction of chemokines and cytokines by 7e and murabutide in wild-type RAW264.7 murine macrophages, and abrogation of responsiveness in both MAL/MyD88- and TRIF/TRAM-double-knockout cell-lines. Means of duplicates are shown. The activity was 7f (not shown) was essentially identical to that of 7e.
Figure 3:
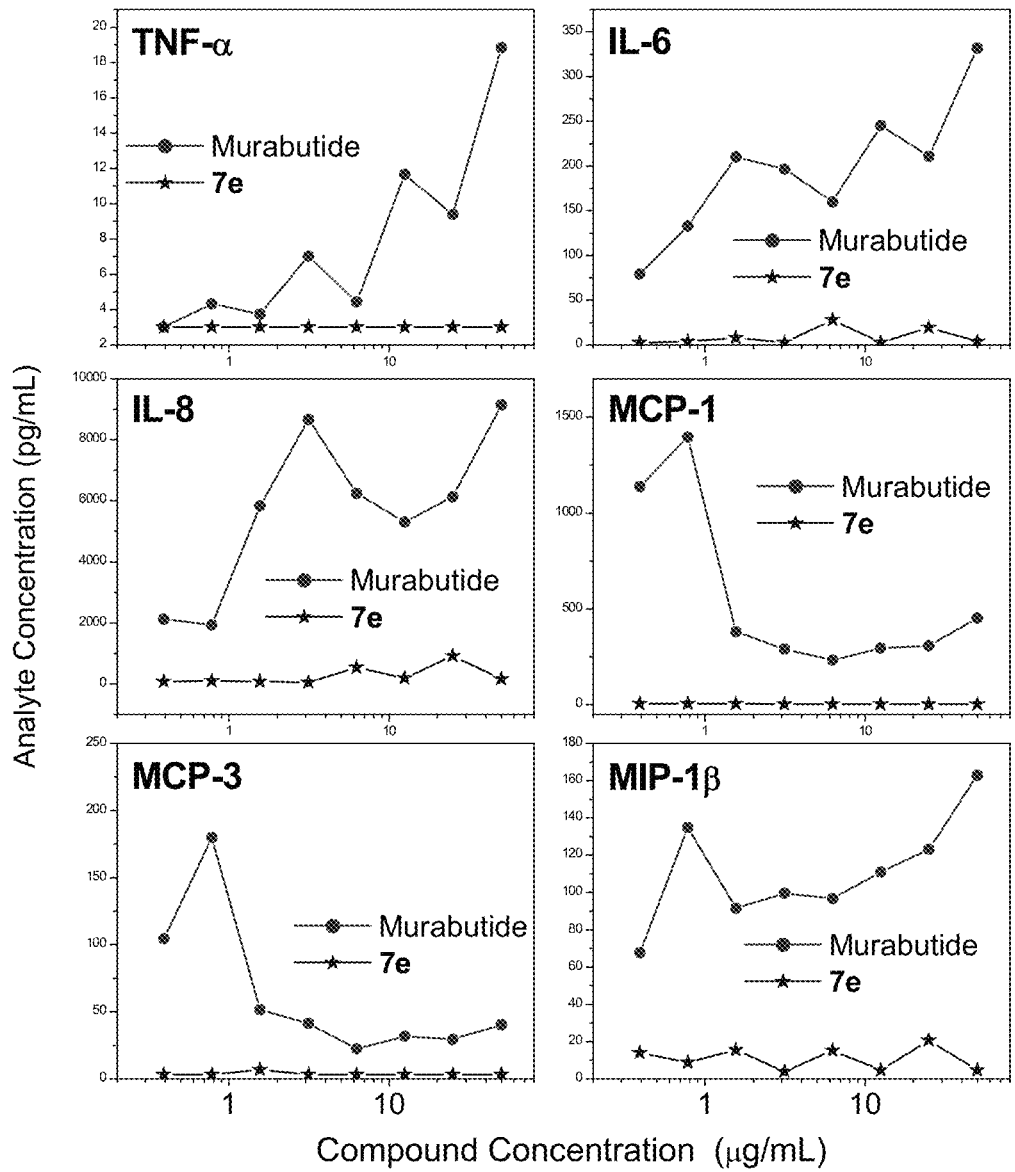
FIG. 3 shows absence of induction of chemokines and cytokines by 7e in human PBMCs. Means of duplicates are shown. The activity was 7f (not shown) was essentially identical to that of 7e.

Cytokine induction by 7e and 7f was examined in murine-derived cell lines. Both 7e and 7f, as well as murabutide, were potently immunostimulatory in the wild-type murine macrophage cell line RAW264.7, strongly inducing chemokines and proinflammatory cytokines (representative data for 7e and murabutide are shown in FIG. 2). Cytokine and chemokine induction of these NOD2-active compounds were significantly diminished in both TRIF/TRAM, as well as in MAL/MyD88 double-knockout murine macrophage/microglial cell lines (FIG. 3), suggesting that both pathways are obligatory for NOD2 signaling and that NOD2-mediated Rip2 recruitment simultaneously engages both MAL/MyD88 and TRIF/TRAM signaling pathways. Murabutide induced significant levels of cytokines and chemokines both in human peripheral blood mononuclear cells (PBMCs; FIG. 3), and in human whole blood. None of the small molecules (including 1, as well as the optimized, equipotent analogues 7e and 7f) showed any activity (see FIG. 3). The absence of activity was not due to extensive plasma protein binding by re-examining under near-serum-free conditions.

The apparent dissociation between activity in primary screens (FIG. 1) and quiescence in secondary screens in human blood (FIG. 3) was consistent with observations with TLR8-active 2,3-diamino-furo[2,3-c]pyridines; the most active compound of this series showed prominent adjuvantic effects in immunization studies, although no proinflammatory cytokine induction was observed in human blood-based assays (Salunke, D. B.; et al. *J. Med. Chem.* 2012, 55, 8137-8151).

Figure 4:
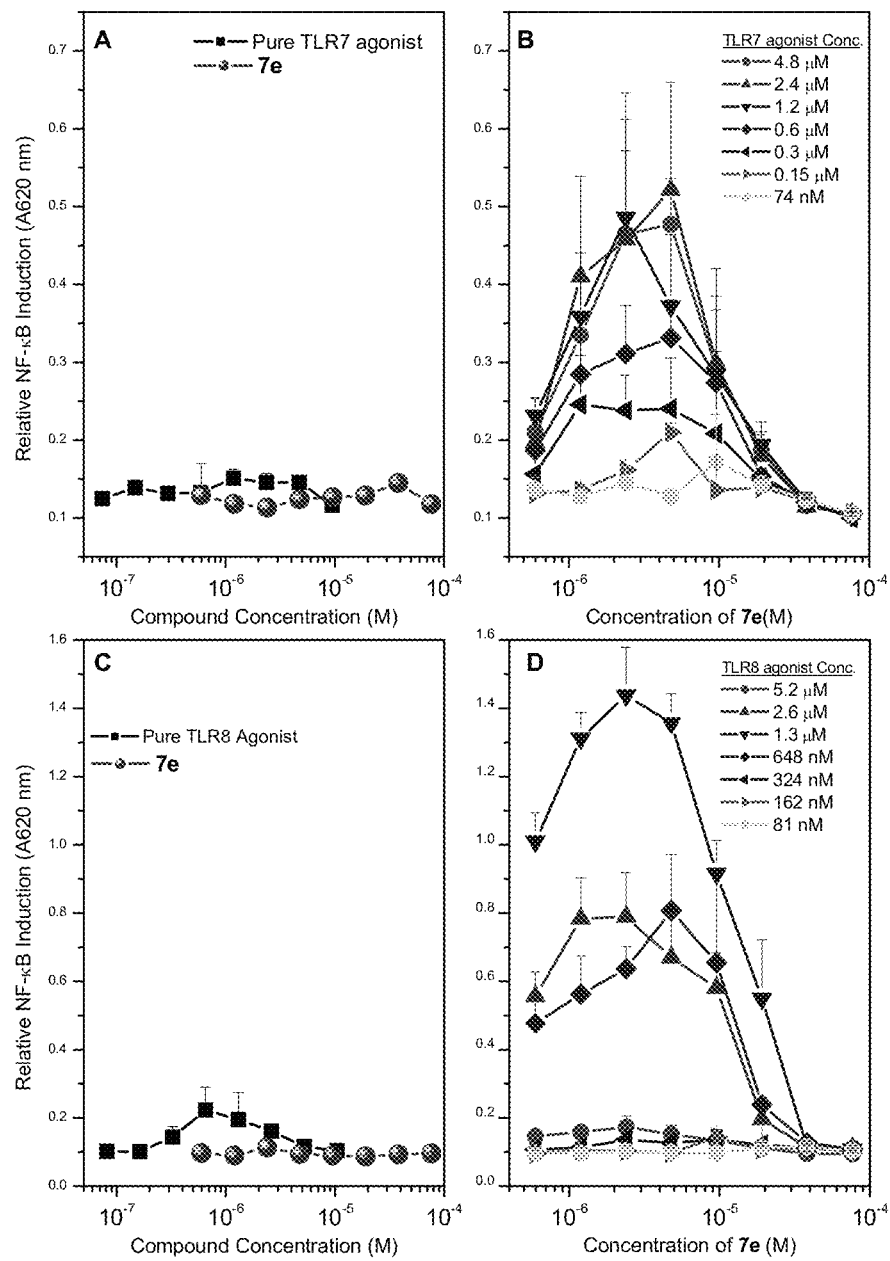
FIG. 4 shows enhancement of NF-κB translocation responses of THP-1 reporter cells to TLR7 (Panels A, B) and TLR8 (C, D) stimuli by 7e. THP-1 cells do not respond to TLR7 stimuli (Panel A), and very weakly to TLR8 agonists (C). The enhancement of TLR8 responses is distinctly biphasic, with concentrations above a threshold leading to diminishing responses (D).
Figure 5:
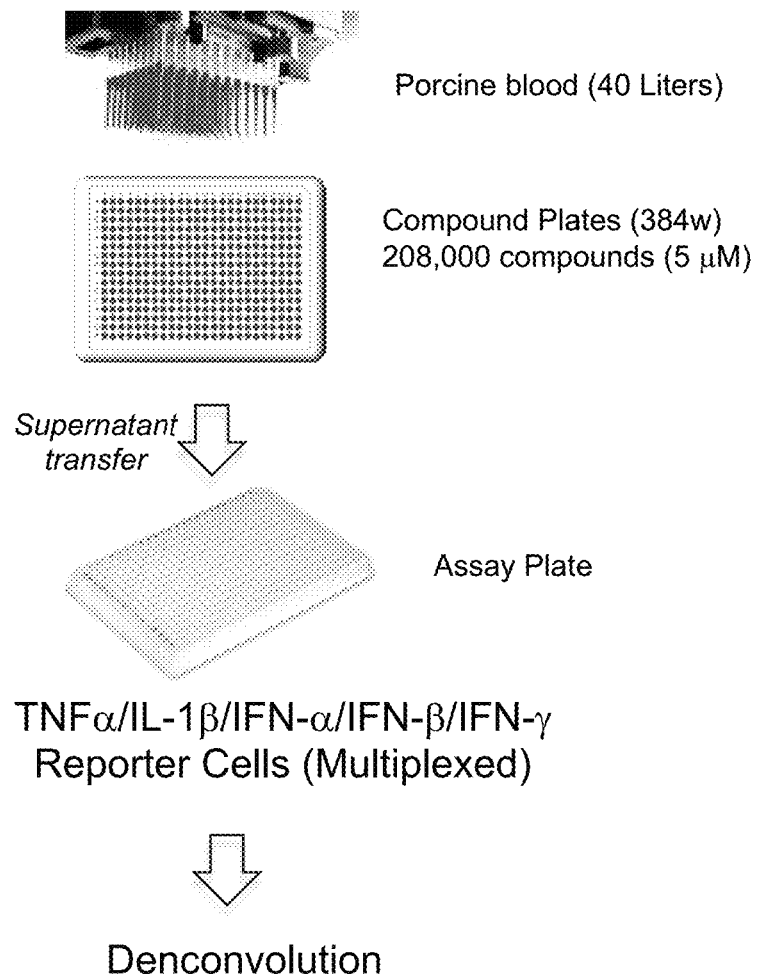
FIG. 5 shows the general schematic of a high throughput screen.
Figure 6:
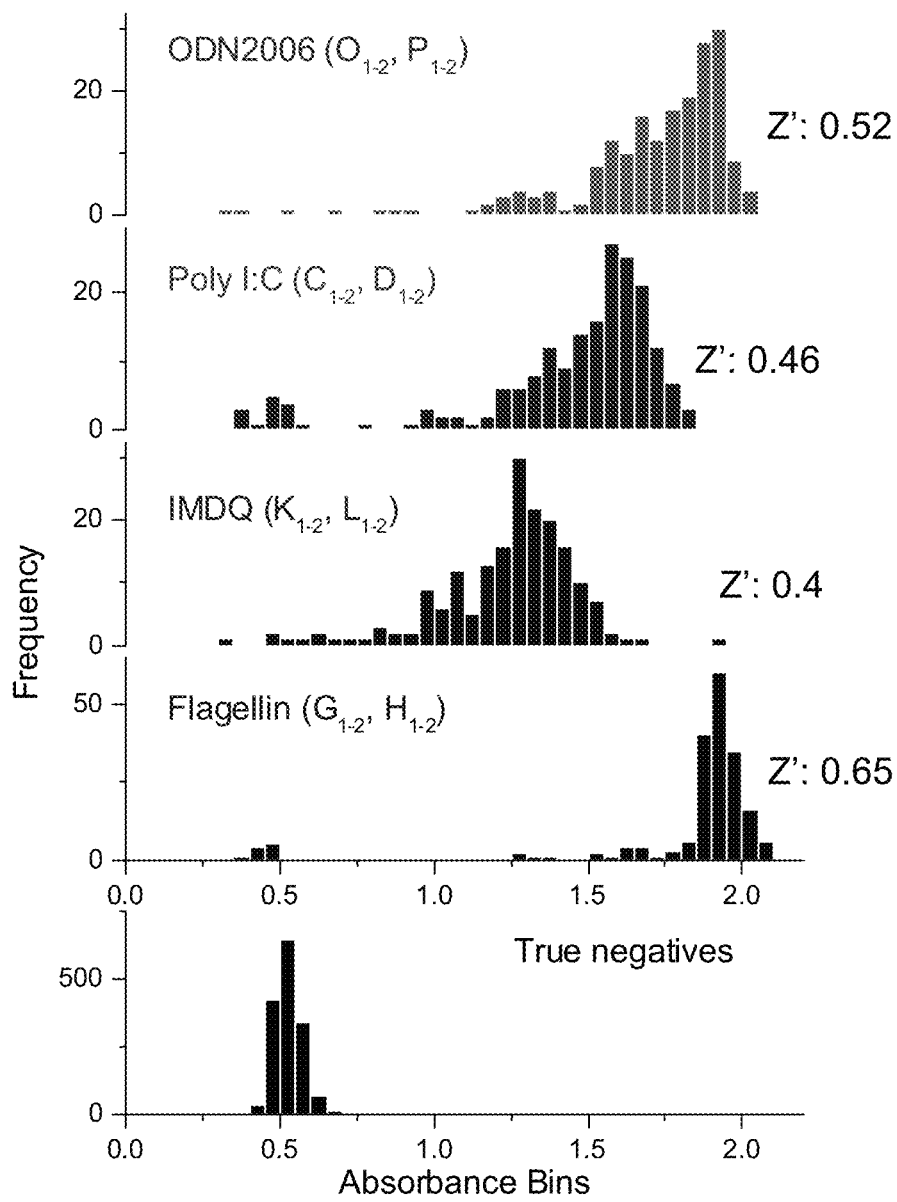
FIG. 6 shows the performance characteristics of high throughput screen. Medium alone (negative controls), Flagellin/TLR5 agonist (10 mg/mL), IMDQ (TLR7/8 agonist (100 ng/mL), Poly (I:C)/TLR3 agonist (10 mg/mL), and ODN2006/TLR9 agonist (10 mg/mL) were included as comparators in duplicate, in each compound plate. Z' values for the individual stimuli ranged between 0.4-0.65.
Figure 7:
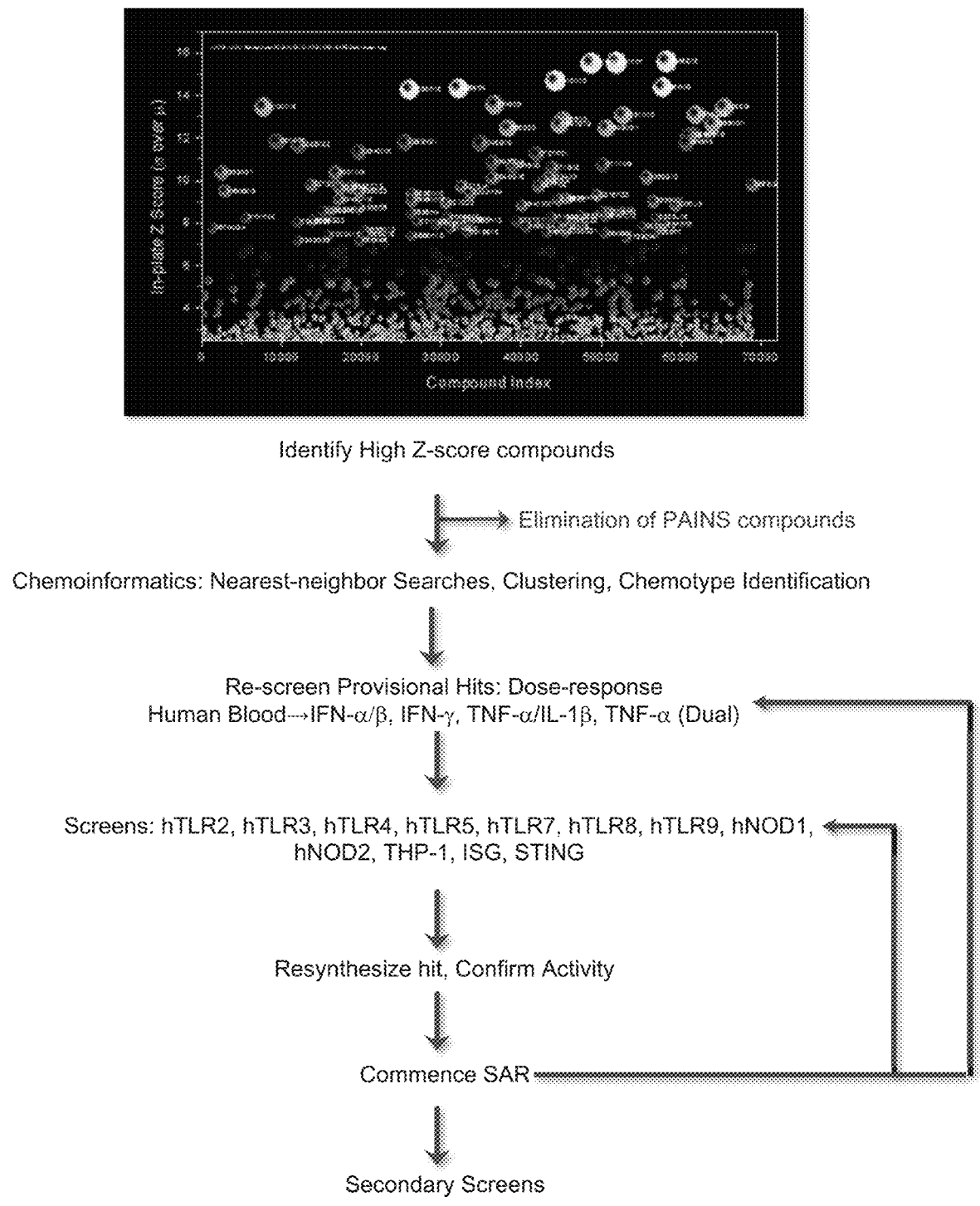
FIG. 7 shows the HTS hit identification workflow.
Figure 8:
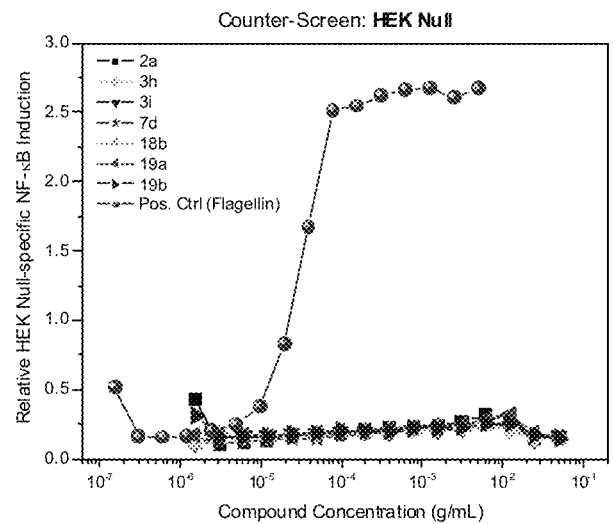
FIG. 8 shows Counter-Screen: HEK Null.
Figure 9:
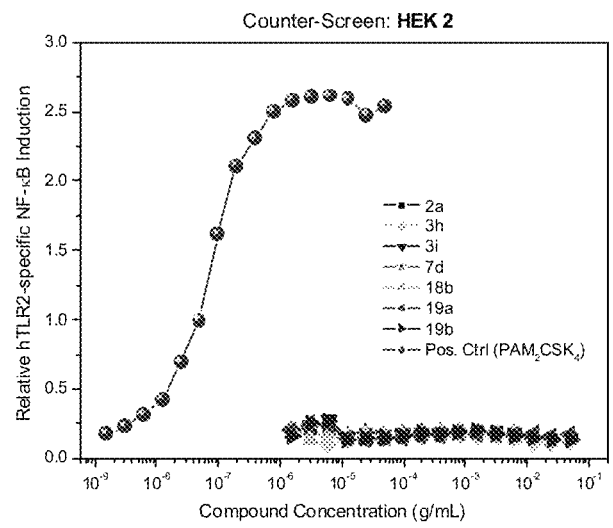
FIG. 9 shows Counter-Screen: HEK 2.
Figure 10:
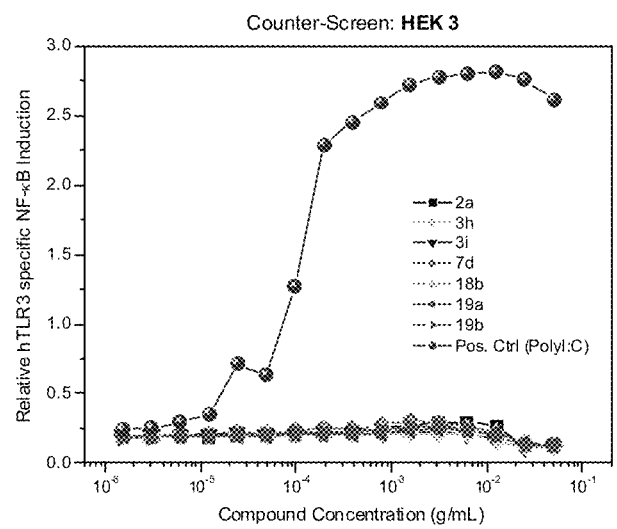
FIG. 10 shows Counter-Screen: HEK 3.
Figure 11:
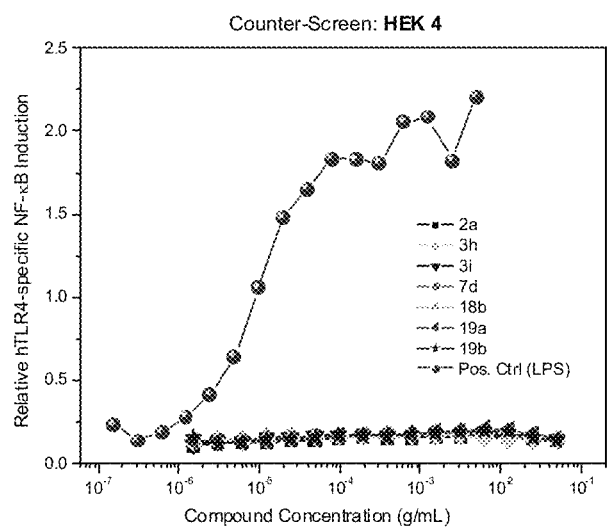
FIG. 11 shows Counter-Screen: HEK 4.
Figure 12:
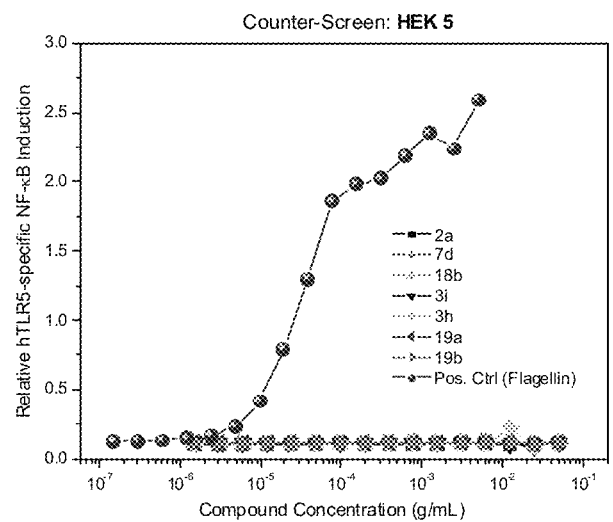
FIG. 12 shows Counter-Screen: HEK 5.
Figure 13:
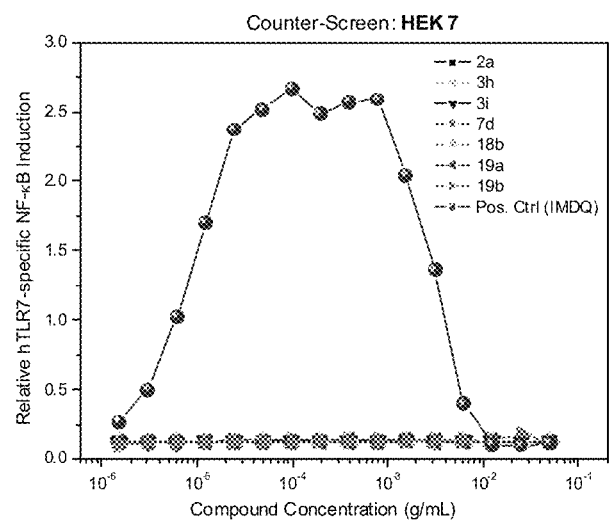
FIG. 13 shows Counter-Screen: HEK 7.
Figure 14:
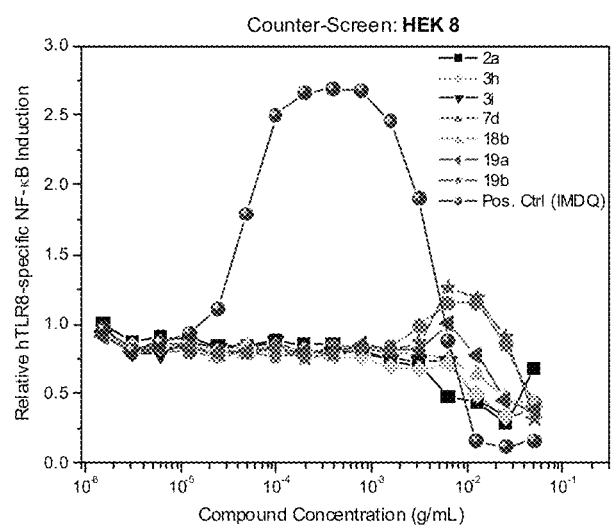
FIG. 14 shows Counter-Screen: HEK 8.
Figure 15:
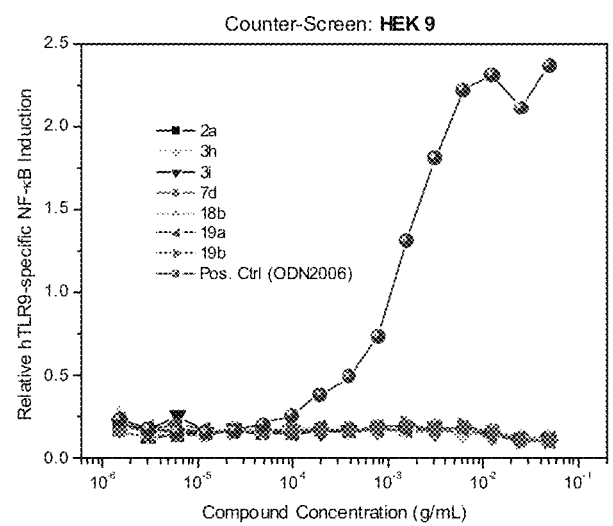
FIG. 15 shows Counter-Screen: HEK 9.
Figure 16:
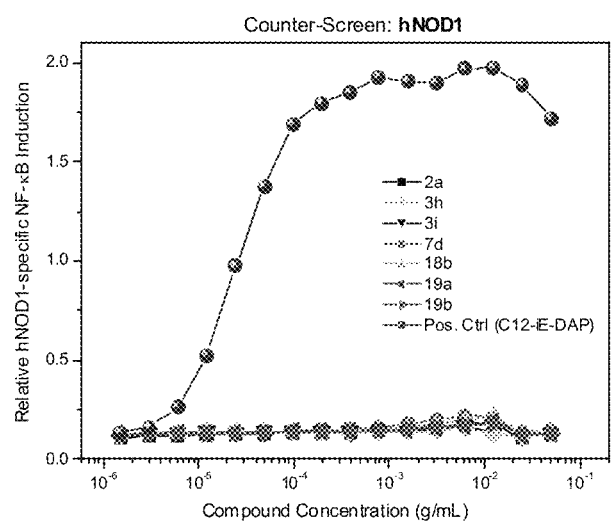
FIG. 16 shows Counter-Screen: hNOD1.
Figure 17:
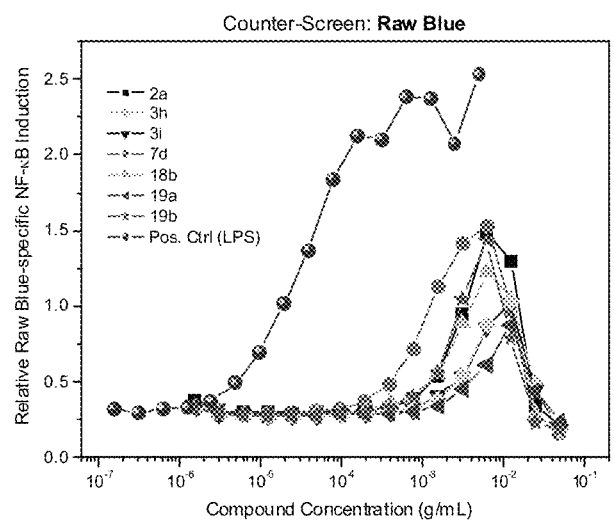
FIG. 17 shows Counter-Screen: Raw Blue.
Figure 18:
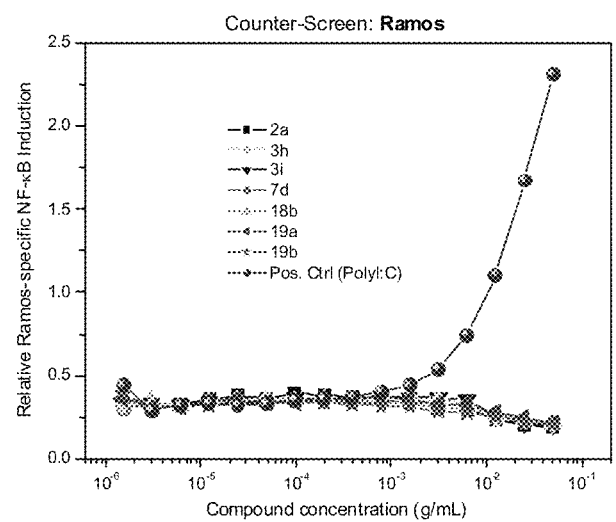
FIG. 18 shows Counter-Screen: Ramos.
Figure 19:
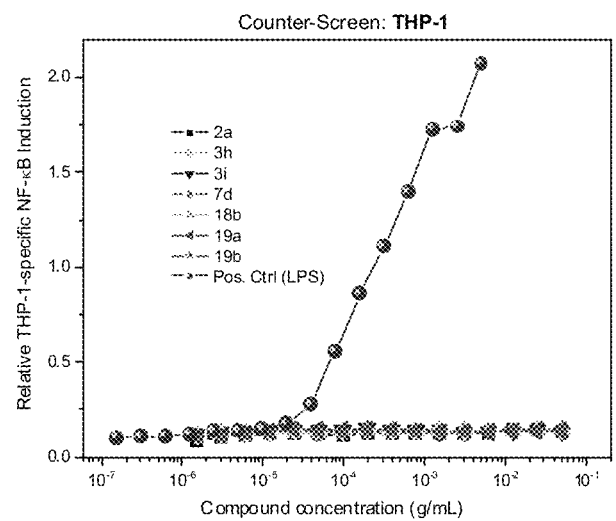
FIG. 19 shows Counter-Screen: THP-1.

Given that Rip2 activity is proximal to several of the components that constitute the multiprotein signaling complexes involved in innate immune signaling, and Rip2 participates in signaling through some, but not all, TLRs, it was of particular interest to examine if the benzimidazole-thiophene-2-carboxamide formula I compounds could synergize with other innate immune stimuli. THP-1 NF-κB reporter cells (human monocytic cell line-derived) respond very weakly to TLR5, TLR8, NOD1 and NOD2 stimuli, and not at all to TLR3, TLR7 and TLR9 agonists (Salyer, A. C.; et al. *PloS one* 2016, 11, e0149848), the benzimidazole-thiophene-2-carboxamide compounds also did not elicit activity in these cells. THP-1 NF-κB reporter cells were concurrently exposed to graded concentrations of either 7e or 7f, and a variety of innate immune stimuli, including TLR-2, -3, -4, -5, -7, -8, and -9 agonists. An enhancement in NF-κB translocation was observed. The amplification was particularly pronounced for TLR7 and TLR8 (FIG. 4), but was also evident for TLR5, and absent for TLR2 and TLR4 stimuli (data not shown), suggesting that engagement of NOD2 by these non-canonical small-molecule agonists upregulate intracellular innate immune sensing (flagellin is also recognized in a TLR5-independent manner by intracellular receptors including NLRC4 and NAIP5).

Formulation and Administration of Formula I Compounds

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be prepared.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilative edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Methods of Treatment

Formula I compounds may be useful as therapeutic adjuvants to vaccines in the treatment of immune-related disorders.

EXAMPLES

The invention will now be illustrated by the following non-limiting Examples.

Example 1: General Procedure for the Synthesis of Compounds 2a-q, 3a-l and 4a-b

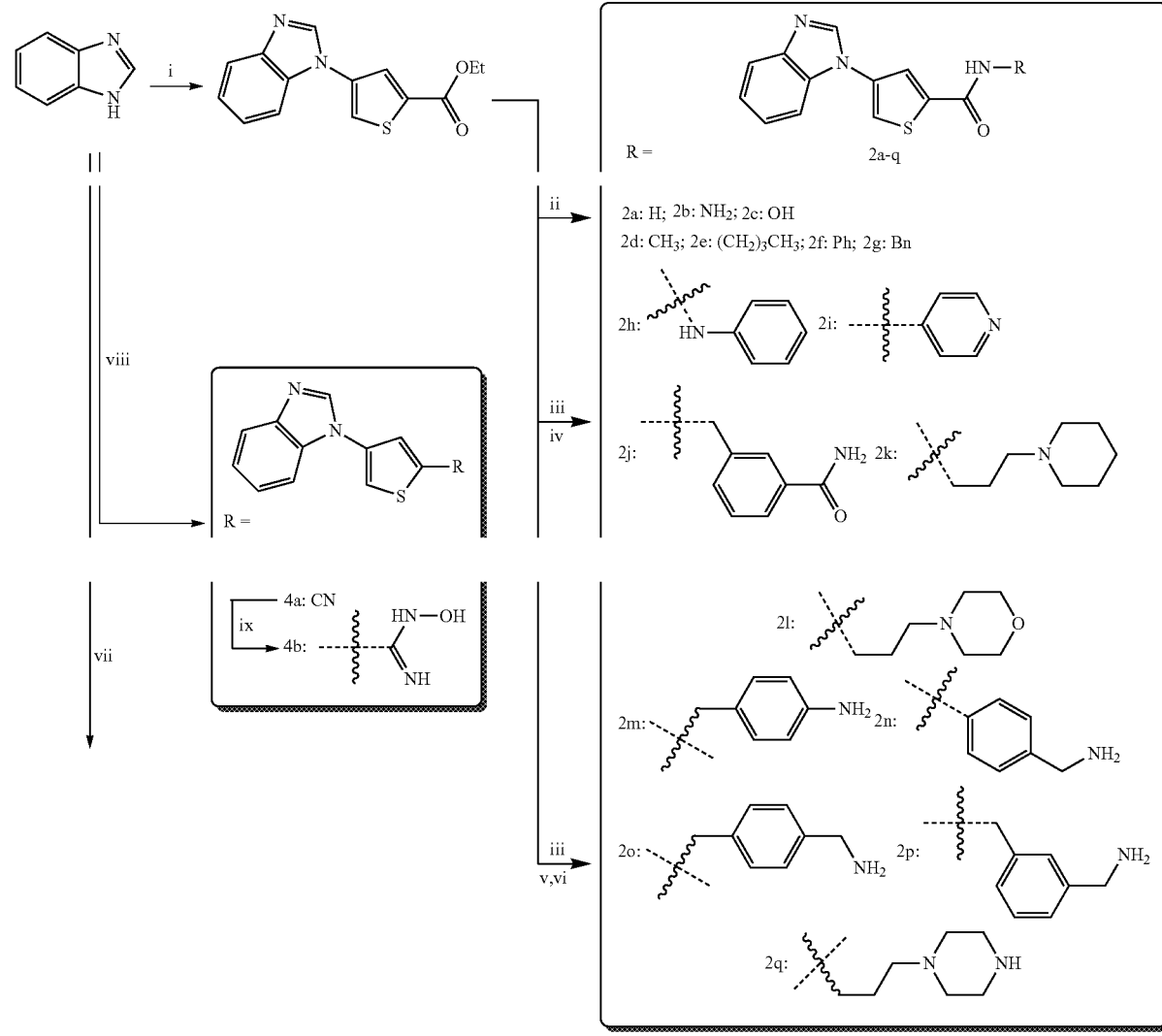

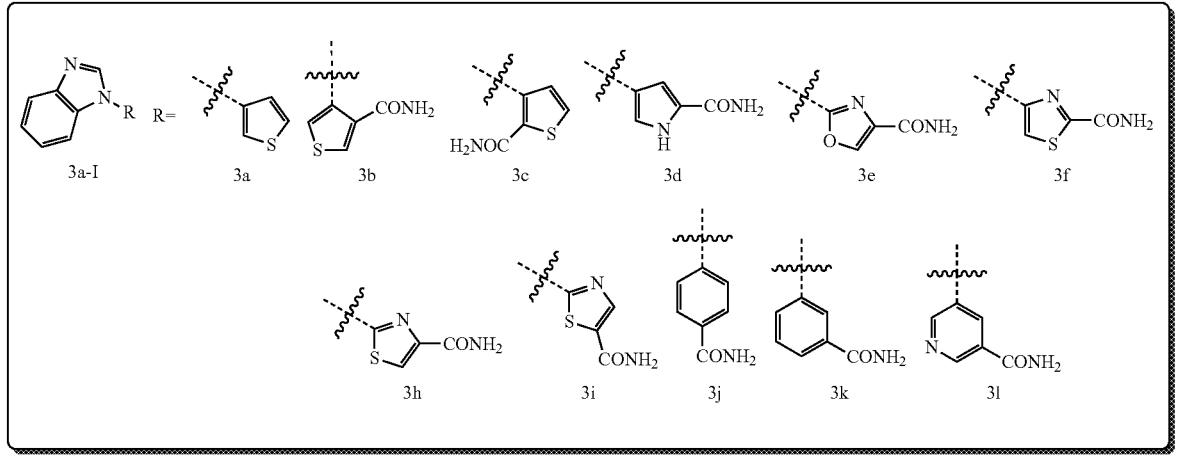

Reagents and Conditions
(i) Ethyl 4-bromothiophene-2-carboxylate, CuI, L-proline, K$_2$CO$_3$, DMF, 120° C., 36 h;
(ii) 7 N NH$_3$ in MeOH, 60° C., 12 h (for 2a); hydrazine hydrate, EtOH, 80° C., 24 h (for 2b); hydroxylamine hydrochloride, KOH, MeOH, 65° C., 12 h (for 2c);
(iii) NaOH, EtOH, 80° C., 3 h;
(iv) methylamine solution (2 M in MeOH) (for 2d), alkyl/aryl amine (for 2e-g, 2i-2l), phenylhydrazine (for 2h), HATU, DIPEA, DCM, 12 h;
(v) mono-N-Boc-protected alkyl/aryl bis-amine, HATU, DIPEA, DCM, 12 h;
(vi) 4 M HCl in dioxane, 1 h;
(vii) 3-bromothiophene, CuI, L-proline, K$_2$CO$_3$, DMF, 120° C., 36 h (for 3a); bromothiophene carbonitrile, CuI, L-proline, K$_2$CO$_3$, DMF, microwave, 150° C., 1 h; sulfuric acid, 6 h (for 3b, 3c); ethyl bromo(aryl/heteroaryl) carboxylate, CuI, L-proline, K$_2$CO$_3$, DMF, microwave, 120° C., 2 h; 7 N NH$_3$ in MeOH, 60° C., 12 h (3d, 3e, 3h-l); 4-bromothiazole-2-carboxamide, CuI, L-proline, K$_2$CO$_3$, DMF, microwave, 120° C., 1 h (for 3f);
(viii) 4-bromothiophene-2-carbonitrile, CuI, L-proline, K$_2$CO$_3$, DMF, 120° C., 36 h;
(ix) hydroxylamine hydrochloride, EtOH, DIPEA, 80° C., 4 h.

Ethyl 4-(1H-benzo[d]imidazol-1-yl)thiophene-2-carboxylate (1). To a solution of benzimidazole (472.56 mg, 4 mmol) in anhydrous DMF (10 mL) were added ethyl 4-bromothiophene-2-carboxylate (1128.48 mg, 4.8 mmol), CuI (76.18 mg, 0.4 mmol), L-proline (92.10 mg, 0.8 mmol), and K$_2$CO$_3$ (1105.68 mg, 8 mmol). The reaction mixture was stirred at 120° C. for 36 h. The reaction mixture was cooled to room temperature, diluted with water and extracted with 1:1 mixture of ethyl acetate and hexanes (4×20 mL). The combined organic layer was dried over Na$_2$SO$_4$ and concentrated under reduced pressure, and the crude material was purified by flash chromatography (20% EtOAc/hexanes) to obtain the compound 1 as white solid (414 mg, 38%). $^1$H NMR (500 MHz, CDCl$_3$) δ 8.10 (s, 1H), 7.97 (s, 1H), 7.90-7.84 (m, 1H), 7.62 (s, 1H), 7.56-7.51 (m, 1H), 7.41-7.33 (m, 2H), 4.42 (q, J=7.1 Hz, 2H), 1.42 (t, J=7.1 Hz, 3H). $^{13}$C NMR (126 MHz, CDCl$_3$) δ 161.41, 143.85, 142.06, 135.56, 134.92, 133.63, 128.21, 124.27, 123.29, 122.79, 120.95, 110.41, 62.02, 14.46. MS (ESI-TOF) for C$_{14}$H$_{12}$N$_2$O$_2$S [M+H]$^+$ calculated 273.0692; found, 273.0699.

4-(1H-Benzo[d]imidazol-1-yl)thiophene-2-carboxamide (2a). Compound 1 (27.23 mg, 0.1 mmol) was dissolved in 7 N ammonia in methanol (1 mL) and heated in a sealed vial at 60° C. for 12 h. The solvent was removed under reduced pressure and the crude product was purified by flash chromatography (10% MeOH/DCM) to obtain the compound 2a as white solid (20 mg, 82%). $^1$H NMR (500 MHz, Methanol-d$_4$) δ 8.44 (s, 1H), 8.05 (s, 1H), 7.98 (s, 1H), 7.76 (d, J=7.9 Hz, 1H), 7.68 (d, J=8.0 Hz, 1H), 7.45-7.32 (m, 2H). $^{13}$C NMR (126 MHz, DMSO-d$_6$) δ 162.12, 143.36, 143.11, 141.00, 133.86, 132.77, 123.67, 123.65, 122.64, 121.19, 119.93, 110.96. MS (ESI-TOF) for C$_{12}$H$_9$N$_3$OS [M+H]$^+$ calculated 244.0539; found, 244.0543.

4-(1H-Benzo[d]imidazol-1-yl)thiophene-2-carbohydrazide (2b). To a solution of compound 1 (27.23 mg, 0.1 mmol) in EtOH (2 mL) was added hydrazine hydrate (15.57 µL, 0.5 mmol), and then stirred at 80° C. for 24 h. The excess solvent was removed under reduced pressure and the residue was purified by flash chromatography (10% MeOH/DCM) to obtain the compound 2b as white solid (18 mg, 70%). $^1$H NMR (500 MHz, DMSO-d$_6$) δ 9.97 (s, 1H), 8.56 (s, 1H), 8.13 (d, J=8.6 Hz, 2H), 7.76 (dd, J=12.6, 8.0 Hz, 2H), 7.44-7.28 (m, 2H), 4.57 (s, 2H). $^{13}$C NMR (126 MHz, DMSO-d$_6$) δ 160.38, 143.37, 143.09, 139.14, 133.93, 132.70, 123.64, 122.66, 122.37, 120.31, 119.94, 110.98. MS (ESI-TOF) for C$_{12}$H$_{10}$N$_4$OS [M+H]$^+$ calculated 259.0648; found, 259.0641.

4-(1H-Benzo[d]imidazol-1-yl)-N-hydroxythiophene-2-carboxamide (2c). To a solution of compound 1 (27.23 mg, 0.1 mmol) in MeOH (3 mL) were added hydroxylamine hydrochloride (13.89 mg, 0.2 mmol) and KOH (22.44 mg, 0.4 mmol). The reaction mixture was stirred at 65° C. for 12 h. The solvent was removed under reduced pressure and the residue was dissolved in water (2 mL), and neutralized with 2 N HCl. The solid obtained was filtered, washed with water and purified by flash chromatography (10% MeOH/DCM) to obtain the compound 2c as white solid (20 mg, 77%). $^1$H NMR (500 MHz, Methanol-d$_4$) δ 8.44 (s, 1H), 7.99 (s, 1H), 7.90 (s, 1H), 7.76 (d, J=7.9 Hz, 1H), 7.67 (d, J=8.0 Hz, 1H), 7.45-7.33 (m, 2H). $^{13}$C NMR (126 MHz, DMSO-d$_6$) δ 158.41, 142.58, 142.46, 138.50, 132.13, 131.65, 125.41, 124.95, 123.05, 122.89, 117.47, 112.22. MS (ESI-TOF) for C$_{12}$H$_9$N$_3$O$_2$S [M+H]$^+$ calculated 260.0488; found, 260.0493.

4-(1H-Benzo[d]imidazol-1-yl)-N-methylthiophene-2-carboxamide (2d). To a solution of compound 1 (272.32 mg, 1 mmol) in EtOH (5 mL) was added NaOH (240 mg, 6 mmol), and the reaction mixture was stirred for 3 h at 80° C. The solvent was removed under reduced pressure, and the residue was dissolved in water (3 mL) and acidified with 2 N HCl. The solid obtained was filtered, washed with water, and purified by flash chromatography (10% MeOH/DCM) to obtain the intermediate 4-(1H-benzo[d]imidazol-1-yl)thiophene-2-carboxylic acid as brown solid (212 mg, 87%). $^1$H NMR (500 MHz, DMSO-$d_6$) δ 13.53 (s, 1H), 8.66 (s, 1H), 8.26 (s, 1H), 8.15 (s, 1H), 7.77 (d, J=7.9 Hz, 1H), 7.72 (d, J=7.9 Hz, 1H), 7.41-7.28 (m, 2H). $^{13}$C NMR (126 MHz, DMSO-$d_6$) δ 162.34, 143.40, 143.27, 135.34, 134.30, 132.76, 127.97, 123.72, 122.77, 122.67, 119.93, 110.88. MS (ESI-TOF) for $C_{12}H_8N_2O_2S$ [M+H]$^+$ calculated 245.0379; found, 245.0391. To the solution of above intermediate (24.43 mg, 0.1 mmol) in anhydrous DCM (3 mL) were added methylamine solution (2 M in MeOH, 250 μL), HATU (38 mg, 0.1 mmol) and DIPEA (52.26 μL, 0.3 mmol). The reaction mixture was stirred at room temperature for 12 h, and then the mixture was diluted with water and extracted with DCM (3×10 mL). The combined organic layer was dried over $Na_2SO_4$ and concentrated under reduced pressure. The crude product was purified by flash chromatography (40% EtOAc/hexanes) to obtain the compound 2d as white solid (12 mg, 47%). $^1$H NMR (500 MHz, DMSO-$d_6$) δ 8.71-8.65 (m, 1H), 8.57 (s, 1H), 8.14 (s, 1H), 8.10 (s, 1H), 7.78 (d, J=7.9 Hz, 1H), 7.74 (d, J=8.0 Hz, 1H), 7.38 (t, J=7.5 Hz, 1H), 7.33 (t, J=7.5 Hz, 1H), 2.82 (d, J=4.4 Hz, 3H). $^{13}$C NMR (126 MHz, DMSO-$d_6$) δ 160.85, 143.37, 143.10, 140.71, 133.84, 132.72, 123.63, 122.73, 122.65, 120.51, 119.95, 110.93, 26.04. MS (ESI-TOF) for $C_{13}H_{11}N_3OS$ [M+H]$^+$ calculated 258.0696; found, 258.0704.

Compounds 2e-l were synthesized similarly as compound 2d.

4-(1H-Benzo[d]imidazol-1-yl)-N-butylthiophene-2-carboxamide (2e). 4-(1H-Benzo[d]imidazol-1-yl)thiophene-2-carboxylic acid (24.43 mg, 0.1 mmol) and n-butylamine (9.88 μL, 0.1 mmol) were used as reagents. White solid (24 mg, 80%). $^1$H NMR (500 MHz, CDCl$_3$) δ 8.06 (s, 1H), 7.85 (dd, J=5.7, 3.2 Hz, 1H), 7.66 (s, 1H), 7.55-7.48 (m, 2H), 7.34 (dd, J=5.9, 3.0 Hz, 2H), 6.30 (s, 1H), 3.48 (q, J=6.7 Hz, 2H), 1.63 (p, J=7.3 Hz, 2H), 1.42 (h, J=7.3 Hz, 2H), 0.96 (t, J=7.3 Hz, 3H). $^{13}$C NMR (126 MHz, CDCl$_3$) δ 160.91, 143.71, 142.10, 140.81, 134.51, 133.72, 124.26, 123.30, 123.18, 120.84, 120.81, 110.44, 40.14, 31.83, 20.27, 13.90. MS (ESI-TOF) for $C_{16}H_{17}N_3OS$ [M+H]$^+$ calculated 300.1165; found, 300.1177.

4-(1H-Benzo[d]imidazol-1-yl)-N-phenylthiophene-2-carboxamide (2f). 4-(1H-Benzo[d]imidazol-1-yl)thiophene-2-carboxylic acid (24.43 mg, 0.1 mmol) and aniline (9.12 μL, 0.1 mmol) were used as reagents. White solid (30 mg, 94%). $^1$H NMR (500 MHz, Methanol-$d_4$) δ 8.47 (s, 1H), 8.26 (s, 1H), 8.03 (s, 1H), 7.80-7.73 (m, 2H), 7.70 (d, J=8.0 Hz, 2H), 7.48-7.32 (m, 4H), 7.16 (t, J=7.4 Hz, 1H). $^{13}$C NMR (126 MHz, DMSO-$d_6$) δ 159.13, 143.38, 143.17, 140.59, 138.35, 133.95, 132.80, 128.80, 124.12, 124.11, 123.70, 122.71, 122.01, 120.46, 119.99, 110.99. MS (ESI-TOF) for $C_{18}H_{13}N_3OS$ [M+H]$^+$ calculated 320.0852; found, 320.0870.

4-(1H-Benzo[d]imidazol-1-yl)-N-benzylthiophene-2-carboxamide (2g). 4-(1H-Benzo[d]imidazol-1-yl)thiophene-2-carboxylic acid (24.43 mg, 0.1 mmol) and benzylamine (10.92 μL, 0.1 mmol) were used as reagents. White solid (31 mg, 93%). $^1$H NMR (500 MHz, DMSO-$d_6$) δ 9.25 (t, J=5.7 Hz, 1H), 8.57 (s, 1H), 8.26 (s, 1H), 8.14 (s, 1H), 7.76 (dd, J=14.7, 8.0 Hz, 2H), 7.42-7.23 (m, 7H), 4.51 (d, J=5.8 Hz, 2H). $^{13}$C NMR (126 MHz, DMSO-$d_6$) δ 160.44, 143.37, 143.11, 140.49, 139.07, 133.93, 132.71, 128.38, 127.40, 126.97, 123.64, 123.15, 122.65, 120.91, 119.94, 110.95, 42.65. MS (ESI-TOF) for $C_{19}H_{15}N_3OS$ [M+H]$^+$ calculated 334.1009; found, 334.1018.

4-(1H-Benzo[d]imidazol-1-yl)-N'-phenylthiophene-2-carbohydrazide (2h). 4-(1H-Benzo[d]imidazol-1-yl)thiophene-2-carboxylic acid (24.43 mg, 0.1 mmol) and phenylhydrazine (9.85 μL, 0.1 mmol) were used as reagents. White solid (20 mg, 60%). $^1$H NMR (500 MHz, DMSO-$d_6$) δ 10.59 (s, 1H), 8.61 (s, 1H), 8.34 (s, 1H), 8.21 (s, 1H), 8.05 (s, 1H), 7.80 (t, J=7.9 Hz, 2H), 7.43-7.31 (m, 2H), 7.18 (t, J=7.4 Hz, 2H), 6.87-6.79 (m, 2H), 6.75 (t, J=7.2 Hz, 1H). $^{13}$C NMR (126 MHz, DMSO-$d_6$) δ 160.70, 149.15, 143.39, 143.15, 138.47, 134.11, 132.73, 128.81, 123.68, 123.49, 122.70, 121.28, 119.96, 118.86, 112.32, 111.03. MS (ESI-TOF) for $C_{18}H_{14}N_4OS$ [M+H]$^+$ calculated 335.0961; found, 335.0978.

4-(1H-Benzo[d]imidazol-1-yl)-N-(pyridin-4-yl)thiophene-2-carboxamide (2i). 4-(1H-Benzo[d]imidazol-1-yl)thiophene-2-carboxylic acid (24.43 mg, 0.1 mmol) and 4-aminopyridine (9.41 mg, 0.1 mmol) were used as reagents. White solid (30 mg, 94%). $^1$H NMR (500 MHz, Methanol-$d_4$) δ 8.51-8.43 (m, 3H), 8.35-8.29 (m, 1H), 8.12-8.08 (m, 1H), 7.83 (d, J=6.2 Hz, 2H), 7.77 (dd, J=15.8, 8.0 Hz, 2H), 7.48-7.36 (m, 2H). $^{13}$C NMR (126 MHz, DMSO-$d_6$) δ 159.97, 150.46, 145.29, 143.37, 143.18, 139.53, 134.05, 132.80, 125.09, 123.74, 123.09, 122.75, 120.01, 114.01, 110.95. MS (ESI-TOF) for $C_{17}H_{12}N_4OS$ [M+H]$^+$ calculated 321.0805; found, 321.0804.

4-(1H-Benzo[d]imidazol-1-yl)-N-(3-carbamoylbenzyl)thiophene-2-carboxamide (2j). 4-Benzo[d]imidazol-1-yl)thiophene-2-carboxylic acid (24.43 mg, 0.1 mmol) and 3-(aminomethyl)benzamide (15.02 mg, 0.1 mmol) were used as reagents. White solid (29 mg, 77%). $^1$H NMR (500 MHz, DMSO-$d_6$) δ 9.28 (t, J=5.7 Hz, 1H), 8.57 (s, 1H), 8.28-8.23 (m, 1H), 8.17-8.11 (m, 1H), 7.98 (s, 1H), 7.87 (s, 1H), 7.81-7.72 (m, 3H), 7.50 (d, J=7.6 Hz, 1H), 7.46-7.29 (m, 4H), 4.55 (d, J=5.7 Hz, 2H). $^{13}$C NMR (126 MHz, DMSO-$d_6$) δ 167.77, 160.48, 143.37, 143.12, 140.40, 139.21, 134.42, 133.95, 132.73, 130.26, 128.27, 126.75, 125.97, 123.65, 123.25, 122.65, 121.00, 119.95, 110.95, 42.58. MS (ESI-TOF) for $C_{20}H_{16}N_4O_2S$ [M+H]$^+$ calculated 377.1067; found, 377.1078.

4-(1H-Benzo[d]imidazol-1-yl)-N-(3-(piperidin-1-yl)propyl)thiophene-2-carboxamide (2k). 4-(1H-Benzo[d]imidazol-1-yl)thiophene-2-carboxylic acid (24.43 mg, 0.1 mmol) and 3-(piperidin-1-yl)propan-1-amine (15.95 μL, 0.1 mmol) were used as reagents. White solid (27 mg, 73%). $^1$H NMR (500 MHz, Methanol-$d_4$) δ 8.44 (s, 1H), 8.00 (s, 1H), 7.97 (s, 1H), 7.76 (d, J=8.0 Hz, 1H), 7.68 (d, J=8.0 Hz, 1H), 7.48-7.33 (m, 2H), 3.43 (t, J=6.9 Hz, 2H), 2.61-2.44 (m, 6H), 1.87 (p, J=7.0 Hz, 2H), 1.67-1.59 (m, 4H), 1.55-1.43 (m, 2H). $^{13}$C NMR (126 MHz, MeOD) δ 163.34, 143.99, 143.93, 141.70, 135.39, 134.54, 125.46, 124.64, 124.48, 123.09, 120.60, 111.95, 57.77, 55.41, 39.44, 27.14, 26.35, 24.95. MS (ESI-TOF) for $C_{20}H_{24}N_4OS$ [M+H]$^+$ calculated 369.1744; found, 369.1753.

4-(1H-Benzo[d]imidazol-1-yl)-N-(3-morpholinopropyl)thiophene-2-carboxamide (2l). 4-(1H-Benzo[d]imidazol-1-yl)thiophene-2-carboxylic acid (24.43 mg, 0.1 mmol) and 3-morpholinopropan-1-amine (14.61 μL, 0.1 mmol) were used as reagents. White solid (31 mg, 84%). $^1$H NMR (500 MHz, Methanol-$d_4$) δ 8.44 (s, 1H), 8.00 (s, 1H), 7.97 (s, 1H), 7.77 (d, J=7.9 Hz, 1H), 7.69 (d, J=8.0 Hz, 1H), 7.46-7.34 (m, 2H), 3.69 (t, J=4.5 Hz, 4H), 3.45 (t, J=7.0 Hz, 2H), 2.54-2.41 (m, 6H), 1.85 (p, J=7.1 Hz, 2H). $^{13}$C NMR (126 MHz, DMSO-$d_6$) δ 160.33, 143.37, 143.12, 140.85, 133.83, 132.75, 123.64, 122.85, 122.65, 120.67, 119.95, 110.93, 66.20, 55.87, 53.33, 37.65, 26.02. MS (ESI-TOF) for $C_{19}H_{22}N_4O_2S$ [M+H]$^+$ calculated 371.1536; found, 371.1543.

N-(4-Aminobenzyl)-4-(1H-benzo[d]imidazol-1-yl)thiophene-2-carboxamide (2m). To a solution of 4-(1H-benzo[d]imidazol-1-yl)thiophene-2-carboxylic acid (preparation shown in the compound 2d, 48.85 mg, 0.2 mmol) in anhydrous DCM (5 mL) were added tert-butyl (4-(aminomethyl)phenyl)carbamate (44.46 mg, 0.2 mmol), HATU (76.05 mg, 0.2 mmol) and DIPEA (104.51 μL, 0.6 mmol). The reaction mixture was stirred at room temperature for 12 h, and then the mixture was diluted with water and extracted with DCM (3×10 mL). The combined organic layer was dried over Na$_2$SO$_4$ and concentrated under reduced pressure. The crude product was purified by flash chromatography (40% EtOAc/hexanes) to obtain the N-Boc protected intermediate as white solid (88 mg, 98%). $^1$H NMR (500 MHz, Methanol-d$_4$) δ 8.43 (s, 1H), 8.04 (s, 1H), 7.99-7.94 (m, 1H), 7.75 (d, J=7.9 Hz, 1H), 7.68 (d, J=7.9 Hz, 1H), 7.46-7.32 (m, 4H), 7.28 (d, J=8.4 Hz, 2H), 4.52 (s, 2H), 1.51 (s, 9H). $^{13}$C NMR (126 MHz, MeOD) δ 163.16, 155.29, 143.97, 143.92, 141.72, 139.86, 135.44, 134.52, 133.88, 129.32, 125.45, 124.71, 124.46, 123.12, 120.55, 119.92, 112.01, 80.81, 44.21, 28.70. MS (ESI-TOF) for $C_{24}H_{24}N_4O_3S$ [M+H]$^+$ calculated 449.1642; found, 449.1658. To a stirred solution of N-Boc protected intermediate (44.85 mg, 0.1 mmol) in 1,4-dioxane (1 mL) was added hydrogen chloride (1 mL, 4 M in dioxane), and the reaction mixture was stirred at room temperature for 1 h. Excess solvent was removed under reduced pressure, and the resulting residue was thoroughly washed with diethyl ether to obtain the desired compound 2m as pale yellow solid (34 mg, 98%). $^1$H NMR (500 MHz, Methano-d$_4$) δ 9.69 (s, 1H), 8.28 (s, 1H), 8.21 (s, 1H), 7.93 (d, J=14.4 Hz, 2H), 7.71 (s, 2H), 7.58 (d, J=6.1 Hz, 2H), 7.40 (d, J=6.2 Hz, 2H), 4.63 (s, 2H). $^{13}$C NMR (126 MHz, MeOD) δ 162.91, 142.35, 141.33, 141.32, 131.01, 130.61, 128.44, 128.29, 128.25, 127.38, 127.36, 125.54, 124.28, 116.80, 116.76, 114.21, 43.96. MS (ESI-TOF) for $C_{19}H_{16}N_4OS$ [M+H]$^+$ calculated 349.1118; found, 349.1120.

Compounds 2n-q were synthesized similarly as compound 2m.

N-(4-(Aminomethyl)phenyl)-4-(1H-benzo[d]imidazol-1-yl)thiophene-2-carboxamide (2n). N-Boc protected intermediate. 4-(1H-Benzo[d]imidazol-1-yl)thiophene-2-carboxylic acid (48.85 mg, 0.2 mmol) and tert-butyl (4-aminobenzyl)carbamate (44.46 mg, 0.2 mmol) were used as reagents. White solid (79 mg, 88%). $^1$H NMR (500 MHz, Methanol-d$_4$) δ 8.47 (s, 1H), 8.26 (s, 1H), 8.04 (s, 1H), 7.81-7.72 (m, 2H), 7.66 (d, J=8.2 Hz, 2H), 7.49-7.35 (m, 2H), 7.29 (d, J=8.3 Hz, 2H), 4.22 (s, 2H), 1.46 (s, 9H). $^{13}$C NMR (126 MHz, MeOD) δ 161.55, 158.59, 144.01, 143.96, 142.30, 138.22, 137.53, 135.50, 134.56, 128.73, 125.49, 125.14, 124.51, 123.79, 122.15, 120.60, 112.05, 80.21, 44.63, 28.78. MS (ESI-TOF) for $C_{24}H_{24}N_4O_3S$ [M+H]$^+$ calculated 449.1642; found, 449.1655.

Compound 2n. N-Boc protected intermediate (44.85 mg, 0.1 mmol) was used as reagent. White solid (34 mg, 98%). $^1$H NMR (500 MHz, Methanol-d$_4$) δ 9.82 (s, 1H), 8.46 (s, 1H), 8.36 (s, 1H), 8.04-7.94 (m, 2H), 7.87 (d, J=8.3 Hz, 2H), 7.79-7.71 (m, 2H), 7.49 (d, J=8.3 Hz, 2H), 4.12 (s, 2H). $^{13}$C NMR (126 MHz, MeOD) δ 161.17, 143.12, 142.54, 140.29, 132.83, 132.35, 132.00, 130.78, 130.56, 128.80, 128.77, 128.29, 125.84, 122.43, 116.19, 114.48, 43.93. MS (ESI-TOF) for $C_{19}H_{16}N_4OS$ [M+H]$^+$ calculated 349.1118; found, 349.1120.

N-(4-(Aminomethyl)benzyl)-4-(1H-benzo[d]imidazol-1-yl)thiophene-2-carboxamide (2o). N-Boc protected intermediate. 4-(1H-Benzo[d]imidazol-1-yl)thiophene-2-carboxylic acid (48.85 mg, 0.2 mmol) and tert-butyl (4-(aminomethyl)benzyl)carbamate (47.26 mg, 0.2 mmol) were used as reagents. White solid (70 mg, 76%). $^1$H NMR (500 MHz, Methanol-d$_4$) δ 8.43 (s, 1H), 8.07-8.02 (m, 1H), 7.98 (s, 1H), 7.76 (d, J=7.8 Hz, 1H), 7.69 (d, J=7.9 Hz, 1H), 7.45-7.30 (m, 4H), 7.26 (d, J=7.9 Hz, 2H), 4.56 (s, 2H), 4.21 (s, 2H), 1.44 (s, 9H). $^{13}$C NMR (126 MHz, MeOD) δ 163.23, 158.56, 143.98, 143.93, 141.67, 140.17, 138.52, 135.45, 134.53, 128.86, 128.42, 125.45, 124.75, 124.47, 123.19, 120.56, 112.00, 80.18, 44.75, 44.35, 28.76. MS (ESI-TOF) for $C_{25}H_{26}N_4O_3S$ [M+H]$^+$ calculated 463.1798; found, 463.1808.

Compound 2o. N-Boc protected intermediate (46.26 mg, 0.1 mmol) was used as reagent. White solid (35 mg, 97%). $^1$H NMR (500 MHz, Methanol-d$_4$) δ 9.78 (s, 1H), 8.30 (s, 1H), 8.20 (s, 1H), 8.00-7.89 (m, 2H), 7.78-7.70 (m, 2H), 7.51-7.42 (m, 4H), 4.62 (s, 2H), 4.11 (s, 2H). $^{13}$C NMR (126 MHz, MeOD) δ 162.83, 142.56, 141.12, 133.44, 132.88, 132.64, 132.07, 130.26, 129.47, 128.68, 128.62, 127.49, 125.28, 116.29, 114.31, 44.20, 44.04. MS (ESI-TOF) for $C_{20}H_{18}N_4OS$ [M+H]$^+$ calculated 363.1274; found, 363.1260.

N-(3-(Aminomethyl)benzyl)-4-(1H-benzo[d]imidazol-1-yl)thiophene-2-carboxamide (2p). N-Boc protected intermediate. 4-(1H-Benzo[d]imidazol-1-yl)thiophene-2-carboxylic acid (48.85 mg, 0.2 mmol) and tert-butyl (3-(aminomethyl)benzyl)carbamate (44.58 μL, 0.2 mmol) were used as reagents. White solid (73 mg, 79%). $^1$H NMR (500 MHz, Methanol-d$_4$) δ 8.44 (s, 1H), 8.06 (s, 1H), 7.99 (d, J=1.2 Hz, 1H), 7.76 (d, J=7.8 Hz, 1H), 7.70 (d, J=7.9 Hz, 1H), 7.45-7.34 (m, 2H), 7.33-7.23 (m, 3H), 7.18 (d, J=7.5 Hz, 1H), 4.58 (s, 2H), 4.22 (s, 2H), 1.39 (s, 9H). $^{13}$C NMR (126 MHz, MeOD) δ 163.23, 158.58, 143.99, 143.91, 141.71, 139.99, 135.45, 134.52, 129.71, 127.38, 127.19, 127.17, 125.46, 124.76, 124.48, 123.17, 120.58, 112.01, 80.17, 44.91, 44.52, 28.74. MS (ESI-TOF) for $C_{25}H_{26}N_4O_3S$ [M+H]$^+$ calculated 463.1798; found, 463.1807.

Compound 2p. N-Boc protected intermediate (46.26 mg, 0.1 mmol) was used as reagent. White solid (34 mg, 94%). $^1$H NMR (500 MHz, Methanol-d$_4$) δ 9.77 (s, 1H), 8.30 (s, 1H), 8.24 (s, 1H), 7.98-7.89 (m, 2H), 7.76-7.70 (m, 2H), 7.52 (s, 1H), 7.49-7.41 (m, 2H), 7.38 (d, J=7.1 Hz, 1H), 4.63 (s, 2H), 4.13 (s, 2H). $^{13}$C NMR (126 MHz, MeOD) δ 162.88, 142.57, 141.04, 134.74, 132.88, 132.73, 132.10, 130.50, 129.56, 129.49, 128.96, 128.67, 128.59, 127.46, 125.37, 116.32, 114.33, 44.36, 44.29. MS (ESI-TOF) for $C_{20}H_{18}N_4OS$ [M+H]$^+$ calculated 363.1274; found, 363.1282.

4-(1H-Benzo[d]imidazol-1-yl)-N-(3-(piperazin-1-yl)propyl)thiophene-2-carboxamide (2q). N-Boc protected intermediate. 4-(1H-Benzo[d]imidazol-1-yl)thiophene-2-carboxylic acid (48.85 mg, 0.2 mmol) and tert-butyl 4-(3-aminopropyl)piperazine-1-carboxylate (46.71 μL, 0.2 mmol) were used as reagents. Colorless oil (83 mg 88%). $^1$H NMR (500 MHz, Methanol-d$_4$) δ 8.43 (s, 1H), 8.00 (s, 1H), 7.96 (s, 1H), 7.76 (d, J=7.9 Hz, 1H), 7.68 (d, J=8.0 Hz, 1H), 7.46-7.32 (m, 2H), 3.49-3.40 (m, 6H), 2.53-2.38 (m, 6H), 1.85 (p, J=6.5, 6.0 Hz, 2H), 1.44 (s, 9H). $^{13}$C NMR (126 MHz, MeOD) δ 163.29, 156.33, 143.98, 143.92, 141.76, 135.39, 134.53, 125.46, 124.59, 124.48, 123.04, 120.60, 111.95, 81.29, 57.12, 53.99, 39.42, 28.63, 27.31. MS (ESI-TOF) for $C_{24}H_{31}N_5O_3S$ [M+H]$^+$ calculated 470.2220; found, 470.2235.

Compound 2q. N-Boc protected intermediate (46.96 mg, 0.1 mmol) was used as reagent. White solid (35 mg, 95%). $^1$H NMR (500 MHz, Methanol-d$_4$) δ 9.78 (s, 1H), 8.29 (s, 1H), 8.24 (s, 1H), 7.99-7.91 (m, 2H), 7.80-7.68 (m, 2H), 3.71-3.53 (m, 10H), 3.44-3.37 (m, 2H), 2.23-2.11 (m, 2H). $^{13}$C NMR (126 MHz, MeOD) δ 161.93, 141.15, 140.90, 131.45, 131.28, 130.66, 127.30, 127.22, 126.06, 124.11, 114.89, 112.96, 54.71, 48.36, 40.67, 36.40, 23.85. MS (ESI-TOF) for C$_{19}$H$_{23}$N$_5$OS [M+H]$^+$ calculated 370.1696; found, 370.1714.

4-(1H-Benzo[d]imidazol-1-yl)thiophene-3-carboxamide (3b). To a solution of benzimidazole (118.14 mg, 1 mmol) in anhydrous DMF (2.5 mL) were added 4-bromothiophene-3-carbonitrile (225.66 mg, 1.2 mmol), CuI (19.04 mg, 0.1 mmol), L-proline (23.03 mg, 0.2 mmol), and K$_2$CO$_3$ (276.42 mg, 2 mmol). The reaction mixture was heated in a sealed vial at 150° C. for 1 h under microwave irradiation. The reaction mixture was cooled to room temperature, diluted with water and extracted with 1:1 mixture of ethyl acetate and hexanes (3×20 mL). The combined organic layer was dried over Na$_2$SO$_4$ and concentrated under reduced pressure, and the crude material was purified by flash chromatography (20% EtOAc/hexanes) to obtain the intermediate carbonitrile as a pale yellow solid (124 mg, 55%). MS (EST-TOF) for C$_{12}$H$_7$N$_3$S [M+H]$^+$ calculated 226.0433; found, 226.0422. The intermediate carbonitrile (22.53 mg, 0.1 mmol) was dissolved in concentrated sulfuric acid (0.5 mL) and stirred at room temperature for 6 h. The reaction mixture was poured into ice cold water (4 mL) and neutralized with saturated sodium bicarbonate. The mixture was extracted with ethyl acetate (3×10 mL). The combined organic layer was dried over Na$_2$SO$_4$ and concentrated under reduced pressure, and the crude material was purified by flash chromatography (5% MeOH/DCM) to obtain the desired product 3b as white solid (23 mg, 95%). $^1$H NMR (500 MHz, DMSO-d$_6$) δ 8.27 (s, 1H), 8.23 (d, J=3.3 Hz, 1H), 7.92 (d, J=3.3 Hz, 1H), 7.84 (s, 1H), 7.74-7.68 (m, 1H), 7.31-7.21 (m, 4H). $^{13}$C NMR (126 MHz, DMSO-d$_6$) δ 163.57, 144.46, 142.83, 134.71, 132.69, 132.46, 129.68, 123.39, 122.94, 121.87, 119.47, 110.39. MS (ESI-TOF) for C$_{12}$H$_9$N$_3$OS [M+H]$^+$ calculated 244.0539; found, 244.0532.

Compound 3c was synthesized similarly as compound 3b. 3-(1H-Benzo[d]imidazol-1-yl)thiophene-2-carboxamide (3c). Carbonitrile intermediate. 3-Bromothiophene-2-carbonitrile (225.66 mg 1.2 mmol) was used as reagent. Pale yellow solid (117 mg, 52%) MS (ESI-TOS) for C$_{12}$H$_7$N$_3$S [M+H]$^+$ calculated 226.0433; found, 226.0427.

Compound 3c. Carbonitrile intermediate (22.53 mg, 0.1 mmol) was used as reagent. White solid (23 mg, 95%). $^1$H NMR (500 MHz, DMSO-d$_6$) δ 8.37 (s, 1H), 7.93 (d, J=5.2 Hz, 1H), 7.77-7.70 (m, 1H), 7.49 (s, 2H), 7.37 (d, J=5.2 Hz, 1H), 7.32-7.25 (m, 3H). $^{13}$C NMR (126 MHz, DMSO-d$_6$) δ 161.73, 144.37, 143.01, 133.81, 133.50, 129.38, 128.57, 126.60, 123.22, 122.21, 119.65, 110.62. MS (ESI-TOF) for C$_{12}$H$_9$N$_3$OS [M+H]$^+$ calculated 244.0539; found, 244.0536.

4-(1H-Benzo[d]imidazol-1-yl)-1H-pyrrole-2-carboxamide (3d). To a solution of benzimidazole (118.14 mg, 1 mmol) in anhydrous DMF (2.5 mL) were added ethyl 4-bromo-1H-pyrrole-2-carboxylate (218.05 mg, 1 mmol), CuI (19.04 mg, 0.1 mmol), L-proline (23.03 mg, 0.2 mmol), and K$_2$CO$_3$ (276.42 mg, 2 mmol). The reaction mixture was heated in a sealed vial at 120° C. for 2 h under microwave irradiation. The reaction mixture was cooled to room temperature, diluted with water and extracted with 1:1 mixture of ethyl acetate and hexanes (3×20 mL). The combined organic layer was dried over Na$_2$SO$_4$ and concentrated under reduced pressure, and the crude material was purified by flash chromatography (20% EtOAc/hexanes) to obtain the intermediate ethyl carboxylate as brown solid (107 mg, 42%). MS (ESI-TOF) for C$_{14}$H$_{13}$N$_3$O$_2$ [M+H]$^+$ calculated 256.1081; found, 256.1088. The intermediate ethyl carboxylate (25.53 mg, 0.1 mmol) was dissolved in 7 N ammonia in methanol (1 mL) and heated in a sealed vial at 60° C. for 12 h. The solvent was removed under reduced pressure and the crude product was purified by flash chromatography (10% MeOH/DCM) to obtain the compound 3d as white solid (19 mg, 84%). $^1$H NMR (500 MHz, DMSO-d$_6$) δ 11.92 (s, 1H), 8.39 (s, 1H), 7.82-7.52 (m, 3H), 7.38-7.22 (m, 3H), 7.17 (s, 2H). $^{13}$C NMR (126 MHz, DMSO-d$_6$) δ 161.70, 143.42, 143.32, 133.66, 125.93, 123.09, 122.01, 120.70, 119.67, 114.94, 110.71, 104.97. MS (ESI-TOF) for C$_{12}$H$_{10}$N$_4$O [M+H]$^+$ calculated 227.0927; found, 227.0904.

Compound 3e was synthesized similarly as compound 3d. 2-(1H-Benzo[d]imidazol-1-yl)oxazole-4-carboxamide (3e). Ethyl carboxylate intermediate. Ethyl 2-bromooxazole-4-carboxylate (220.02 mg, 1 mmol) was used as reagent. Pale yellow solid (115 mg, 45%). MS (ESI-TOF) for C$_{13}$H$_{11}$N$_3$O$_3$ [M+H]$^+$ calculated 258.0873; found, 258.0878.

Compound 3e. Ethyl carboxylate intermediate (25.73 mg, 0.1 mmol) was used as reagent. White solid (19 mg, 83%). $^1$H NMR (500 MHz, DMSO-d$_6$) δ 8.86 (s, 1H), 8.65 (s, 1H), 8.45 (d, J=8.1 Hz, 1H), 7.94 (s, 1H), 7.83 (d, J=7.9 Hz, 1H), 7.67 (s, 1H), 7.50 (t, J=7.6 Hz, 1H), 7.43 (t, J=7.6 Hz, 1H). $^{13}$C NMR (126 MHz, DMSO-d$_6$) δ 161.33, 149.98, 143.12, 140.85, 139.24, 136.29, 130.56, 125.02, 124.27, 120.15, 113.89. MS (ESI-TOF) for C$_{11}$H$_8$N$_4$O$_2$ [M+H]$^+$ calculated 229.0720; found, 229.0715.

4-(1H-Benzo[d]imidazol-1-yl)thiazole-2-carboxamide (3f). To a solution of benzimidazole (59.07 mg, 0.5 mmol) in anhydrous DMF (2 mL) were added 4-bromothiazole-2-carboxamide (103.52 mg, 0.5 mmol), CuI (9.52 mg, 0.05 mmol), L-proline (11.51 mg, 0.1 mmol), and K$_2$CO$_3$ (138.21 mg, 1 mmol). The reaction mixture was heated in a sealed vial at 120° C. for 1 h under microwave irradiation. The reaction mixture was cooled to room temperature, diluted with water and extracted with ethyl acetate (3×10 mL). The combined organic layer was dried over Na$_2$SO$_4$ and concentrated under reduced pressure, and the crude material was purified by flash chromatography (5% MeOH/DCM) to obtain the product 3f as pale yellow solid (43 mg, 35%). $^1$H NMR (500 MHz, DMSO-d$_6$) δ 8.89 (s, 1H), 8.42 (s, 1H), 8.30 (s, 1H), 8.21 (d, J=8.0 Hz, 1H), 8.07 (s, 1H), 7.78 (d, J=7.9 Hz, 1H), 7.45-7.27 (m, 2H). $^{13}$C NMR (126 MHz, DMSO-d$_6$) δ 163.36, 160.30, 145.97, 143.50, 142.52, 131.85, 124.00, 123.03, 119.81, 113.04, 111.13. MS (ESI-TOF) for C$_{11}$H$_8$N$_4$OS [M+H]$^+$ calculated 245.0492; found, 245.0481.

Compounds 3h-l were synthesized similarly as compound 3d.

2-(1H-Benzo[d]imidazol-1-yl)thiazole-4-carboxamide (3h). Ethyl carboxylate intermediate. Ethyl 2-bromothiazole-4-carboxylate (236.09 mg, 1 mmol) was used as reagent. Pale yellow solid (142 mg, 52%). MS (ESI-TOF) for C$_{13}$H$_{11}$N$_3$O$_2$S [M+H]$^+$ calculated 274.0645; found, 274.0658.

Compound 3h. Ethyl carboxylate intermediate (27.33 mg, 0.1 mmol) was used as reagent. White solid (21 mg, 86%). $^1$H NMR (500 MHz, DMSO-d$_6$) δ 8.98 (s, 1H), 8.42 (d, J=8.1 Hz, 1H), 8.18 (s, 1H), 7.98 (s, 1H), 7.81 (d, J=7.9 Hz, 1H), 7.75 (s, 1H), 7.47 (t, J=7.7 Hz, 1H), 7.41 (t, J=7.6 Hz, 1H). $^{13}$C NMR (126 MHz, DMSO-d$_6$) δ 161.71, 156.39, 147.05, 143.62, 142.56, 131.34, 124.95, 124.05, 120.68, 120.11, 113.71. MS (ESI-TOF) for C$_{11}$H$_8$N$_4$OS [M+H]$^+$ calculated 245.0492; found, 245.0486.

2-(1H-Benzo[d]imidazol-1-yl)thiazole-5-carboxamide (3i). Ethyl carboxylate intermediate. Ethyl 2-bromothiazole-5-carboxylate (149.33 μL, 1 mmol) was used as reagent. Pale yellow solid (139 mg, 51%). MS (ESI-TOF) for $C_{13}H_{11}N_3O_2S$ [M+H]$^+$ calculated 274.0645; found, 274.0653.

Compound 3i. Ethyl carboxylate intermediate (27.33 mg, 0.1 mmol) was used as reagent. White solid (20 mg, 82%). $^1$H NMR (500 MHz, DMSO-d$_6$) δ 8.98 (s, 1H), 8.42 (d, J=8.1 Hz, 1H), 8.18 (s, 1H), 7.98 (s, 1H), 7.81 (d, J=7.9 Hz, 1H), 7.75 (s, 1H), 7.48 (t, J=7.6 Hz, 1H), 7.41 (t, J=7.6 Hz, 1H). $^{13}$C NMR (126 MHz, DMSO-d$_6$) δ 161.70, 156.39, 147.05, 143.62, 142.56, 131.34, 124.95, 124.05, 120.68, 120.11, 113.71. MS (ESI-TOF) for $C_{11}H_8N_4OS$ [M+H]$^+$ calculated 245.0492; found, 245.0484.

4-(1H-Benzo[d]imidazol-1-yl)benzamide (3j). Ethyl carboxylate intermediate. Ethyl 4-bromobenzoate (163.27 μL, 1 mmol) was used as reagent. White solid (178 mg, 67%). $^1$H NMR (500 MHz, Methanol-d$_4$) δ 8.50 (s, 1H), 8.25 (d, J=8.5 Hz, 2H), 7.77 (d, J=8.5 Hz, 3H), 7.68 (d, J=7.3 Hz, 1H), 7.45-7.30 (m, 2H), 4.41 (q, J=7.1 Hz, 2H), 1.42 (t, J=7.1 Hz, 3H). $^{13}$C NMR (126 MHz, MeOD) δ 166.97, 144.60, 143.89, 141.29, 134.17, 132.49, 131.12, 125.51, 124.67, 124.60, 120.75, 112.02, 62.50, 14.60. MS (ESI-TOF) for $C_{16}H_{14}N_2O_2$ [M+H]$^+$ calculated 267.1128; found, 267.1140.

Compound 3j. Ethyl carboxylate intermediate (26.63 mg, 0.1 mmol) was used as reagent. White solid (19 mg, 80%). $^1$H NMR (500 MHz, DMSO-d$_6$) δ 8.64 (s, 1H), 8.12 (d, J=8.4 Hz, 3H), 7.80 (d, J=8.4 Hz, 3H), 7.70 (d, J=7.9 Hz, 1H), 7.51 (s, 1H), 7.35 (p, J=7.2 Hz, 2H). $^{13}$C NMR (126 MHz, DMSO-d$_6$) δ 166.86, 143.95, 143.23, 138.26, 133.09, 132.72, 129.34, 123.68, 122.97, 122.69, 120.04, 110.86. MS (ESI-TOF) for $C_{14}H_{11}N_3O$ [M+H]$^+$ calculated 238.0975; found, 238.0989.

3-(1H-Benzo[d]imidazol-1-yl)benzamide (3k). Ethyl carboxylate intermediate. Ethyl 3-bromobenzoate (160.07 μL, 1 mmol) was used as reagent. Colorless oil (202 mg, 76%). MS (ESI-TOF) for $C_{16}H_{14}N_2O_2$ [M+H]$^+$ calculated 267.1128; found, 267.1132.

Compound 3k. Ethyl carboxylate intermediate (26.63 mg, 0.1 mmol) was used as reagent. White solid (21 mg, 88%). $^1$H NMR (500 MHz, Methanol-d$_4$) δ 8.47 (s, 1H), 8.13 (s, 1H), 8.02 (d, J=7.8 Hz, 1H), 7.84 (d, J=7.9 Hz, 1H), 7.81-7.71 (m, 2H), 7.65 (d, J=7.4 Hz, 1H), 7.43-7.34 (m, 2H). $^{13}$C NMR (126 MHz, MeOD) δ 170.82, 144.38, 144.02, 137.71, 137.27, 134.59, 131.54, 128.38, 125.39, 124.44, 124.39, 120.63, 111.85. MS (ESI-TOF) for $C_{14}H_{11}N_3O$ [M+H]$^+$ calculated 238.0975; found, 238.0977.

5-(1H-Benzo[d]imidazol-1-yl)nicotinamide (3l). Ethyl carboxylate intermediate. Ethyl 5-bromonicotinate (230.06 mg, 1 mmol) was used as reagent. White solid (200 mg, 75%). $^1$H NMR (500 MHz, Methanol-d$_4$) δ 9.23 (s, 1H), 9.10 (d, J=2.1 Hz, 1H), 8.61 (s, 1H), 8.56 (s, 1H), 7.80 (d, J=7.4 Hz, 1H), 7.62 (d, J=7.4 Hz, 1H), 7.48-7.35 (m, 2H), 4.47 (q, J=7.1 Hz, 2H), 1.43 (t, J=7.1 Hz, 3H). $^{13}$C NMR (126 MHz, MeOD) δ 165.44, 150.42, 149.69, 144.47, 144.08, 134.62, 134.45, 133.64, 129.09, 125.75, 124.80, 120.88, 111.44, 63.19, 14.50. MS (ESI-TOF) for $C_{15}H_{13}N_3O_2$ [M+H]$^+$ calculated 268.1081; found, 268.1076.

Compound 3l. Ethyl carboxylate intermediate (26.73 mg, 0.1 mmol) was used as reagent. White solid (20 mg, 84%). $^1$H NMR (500 MHz, DMSO-d$_6$) δ 9.11 (d, J=11.7 Hz, 2H), 8.69 (s, 1H), 8.52 (s, 1H), 8.32 (s, 1H), 7.81 (d, J=7.0 Hz, 2H), 7.72 (d, J=7.8 Hz, 1H), 7.37 (p, J=7.1 Hz, 2H). $^{13}$C NMR (126 MHz, DMSO-d$_6$) δ 165.47, 147.58, 146.89, 143.86, 143.45, 132.92, 132.53, 130.66, 129.97, 123.83, 122.87, 120.07, 110.68. MS (ESI-TOF) for $C_{13}H_{10}N_4O$ [M+H]$^+$ calculated 239.0927; found, 239.0923.

Compound 4a was synthesized similarly as compound 1.

4-(1H-Benzo[d]imidazol-1-yl)thiophene-2-carbonitrile (4a). 4-Bromothiophene-2-carbonitrile (902.64 mg, 4.8 mmol) was used as reagent. Pale orange solid (252 mg, 28%). $^1$H NMR (500 MHz, DMSO-d$_6$) δ 8.63 (s, 1H), 8.53-8.47 (m, 1H), 8.43 (s, 1H), 7.78 (d, J=7.8 Hz, 1H), 7.73 (d, J=7.9 Hz, 1H), 7.42-7.29 (m, 2H). $^{13}$C NMR (126 MHz, DMSO-d$_6$) δ 143.36, 143.23, 134.14, 133.95, 132.62, 124.46, 123.86, 122.86, 119.99, 113.90, 110.92, 109.45. MS (ESI-TOF) for $C_{12}H_7N_3S$ [M+H]$^+$ calculated 226.0433; found, 226.0445.

4-(1H-Benzo[d]imidazol-1-yl)-N-hydroxythiophene-2-carboximidamide (4b). To a solution of compound 4a (22.53 mg, 0.1 mmol) in anhydrous ethanol (3 mL) were added hydroxylamine hydrochloride (17.37 mg, 0.25 mmol) and DIPEA (52.26 μL, 0.3 mmol). The reaction mixture was stirred at 80° C. for 4 h. The solvent was removed under reduced pressure and the residue was purified by flash chromatography (10% MeOH/DCM) to obtain the compound 4a as a white solid (21 mg, 81%). $^1$H NMR (500 MHz, DMSO-d$_6$) δ 9.81 (s, 1H), 8.54 (s, 1H), 7.90 (s, 1H), 7.77 (dd, J=15.4, 7.9 Hz, 3H), 7.43-7.28 (m, 2H), 6.10 (s, 2H). $^{13}$C NMR (126 MHz, DMSO-d$_6$) δ 146.82, 143.39, 143.05, 137.72, 133.36, 132.76, 123.56, 122.55, 120.25, 119.88, 116.11, 111.12. MS (ESI-TOF) for $C_{12}H_{10}N_4OS$ [M+H]$^+$ calculated 259.0648; found, 259.0665.

Example 2: General Procedure for the Synthesis of Compounds 5, 6a-n and 7a-n

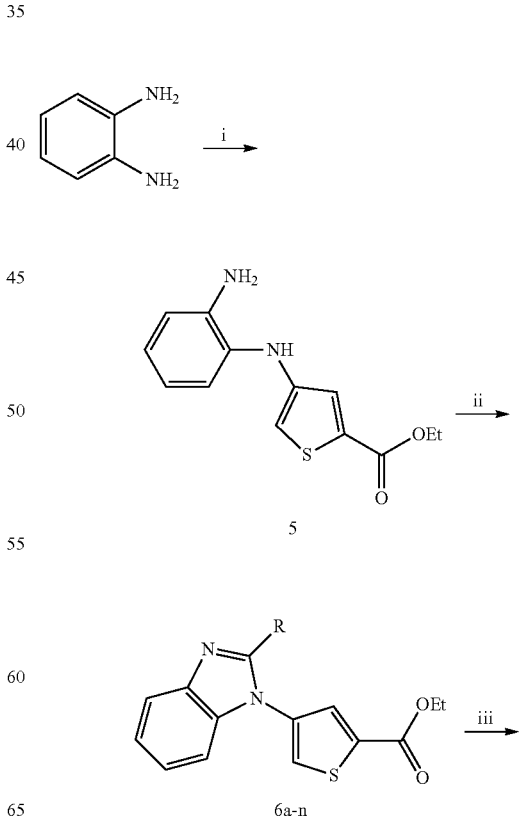

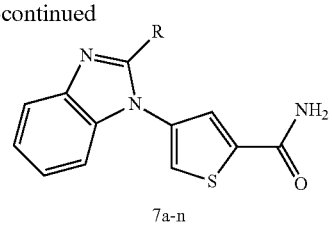

6a, 7a: R = CH₃   6g, 7g: R = (CH₂)₇CH₃
6b, 7b: R = CH₂CH₃   6h, 7h: R = (CH₂)₈CH₃
6c, 7c: R = (CH₂)₂CH₃   6i, 7i R = (CH₂)₁₀CH₃
6d, 7d: R = (CH₂)₃CH₃   6j, 7j: R = (CH₂)₁₂CH₃
6e, 7e: R = (CH₂)₄CH₃   6k, 7k: R = (CH₂)₁₄CH₃
6f, 7f: R = (CH₂)₅CH₃   6l, 7l: R = (CH₂)₁₆CH₃

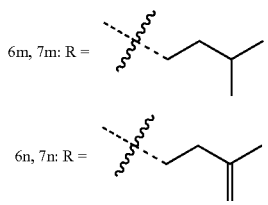

Reagents and Conditions
(i) Ethyl 4-bromothiophene-2-carboxylate, CuI, L-proline, K₂CO₃, DMF, 120° C., 36 h;
(ii) (a) acyl chloride, THF, TEA, 2 h; AcOH, 80° C., 12 h (for 6a-l); (b) 4-methylvaleric acid (for 6m), 4-methylpent-4-enoic acid (for 6n), HATU, DIPEA, DCM, 12 h; AcOH, 80° C., 12 h;
(iii) 7 N NH₃ in MeOH, 60° C., 12 h.

Compound 5 was synthesized similarly as compound 1.

Ethyl 4-((2-aminophenyl)amino)thiophene-2-carboxylate (5). o-Phenylenediamine (432.56 mg, 4 mmol) and ethyl 4-bromothiophene-2-carboxylate (940.4 mg, 4 mmol) were used as reagents. Red oil (546 mg, 52%). $^1$H NMR (500 MHz, DMSO-d₆) δ 7.41 (s, 1H), 7.33 (s, 1H), 7.00 (d, J=7.7 Hz, 1H), 6.77 (t, J=7.5 Hz, 1H), 6.71 (d, J=7.7 Hz, 1H), 6.66 (s, 1H), 6.54 (t, J=7.5 Hz, 1H), 4.75 (s, 2H), 4.26 (q, J=7.1 Hz, 2H), 1.27 (t, J=7.1 Hz, 3H). $^{13}$C NMR (126 MHz, DMSO-d₆) δ 161.45, 144.90, 140.32, 131.10, 129.05, 126.21, 123.11, 120.02, 116.64, 115.20, 107.02, 60.79, 14.18. MS (ESI-TOF) for $C_{13}H_{14}N_2O_2S$ [M+H]⁺ calculated 263.0849; found, 263.0833.

Ethyl 4-(2-methyl-1H-benzo[d]imidazol-1-yl)thiophene-2-carboxylate (6a). To a solution of compound 5 (78.69 mg, 0.3 mmol) in THF (4 mL) were added acetyl chloride (25.59 μL, 0.36 mmol) and triethylamine (83.68 μL, 0.6 mmol) under cooling condition in an ice bath. The reaction mixture was stirred for 2 h at room temperature. The solvent was removed under reduced pressure and the crude material was purified by flash chromatography (20% EtOAc/hexanes) to obtain the N-acyl intermediate as pale yellow solid (75 mg, 82%). $^1$H NMR (500 MHz, Methanol-d₄) δ 7.55 (s, 1H), 7.36 (d, J=7.8 Hz, 1H), 7.20 (d, J=8.1 Hz, 1H), 7.14 (t, J=7.6 Hz, 1H), 6.93 (t, J=7.6 Hz, 1H), 6.86 (s, 1H), 4.32 (q, J=6.9 Hz, 2H), 2.13 (s, 3H), 1.35 (t, J=7.0 Hz, 3H). $^{13}$C NMR (126 MHz, MeOD) δ 172.67, 163.67, 144.55, 139.81, 133.52, 128.67, 128.27, 127.93, 127.36, 122.28, 119.16, 112.93, 62.31, 23.23, 14.58. MS (ESI-TOF) for $C_{15}H_{16}N_2O_3S$ [M+H]⁺ calculated 305.0954; found, 305.0933. The N-acyl intermediate (60.87 mg, 0.2 mmol) was dissolved in acetic acid (2 mL) and stirred at 80° C. for 12 h. The solvent was removed under reduced pressure, and the crude material was purified by flash chromatography (20% EtOAc/hexanes) to obtain the desired product 6a as pale orange solid (53 mg, 93%). MS (ESI-TOF) for $C_{15}H_{14}N_2O_2S$ [M+H]⁺ calculated 287.0849; found, 287.0867.

Compounds 6b-l were synthesized similarly as compound 6a.

Ethyl 4-(2-ethyl-1H-benzo[d]imidazol-1-yl)thiophene-2-carboxylate (6b). N-Acyl intermediate. Propionyl chloride (33.31 μL, 0.36 mmol) was used as reagent. Pale yellow solid (83 mg, 87%). $^1$H NMR (500 MHz, Methanol-d₄) δ 7.52 (s, 1H), 7.40 (d, J=7.9 Hz, 1H), 7.20 (d, J=8.0 Hz, 1H), 7.14 (t, J=7.6 Hz, 1H), 6.95 (t, J=7.5 Hz, 1H), 6.80 (s, 1H), 4.31 (q, J=7.0 Hz, 2H), 2.40 (q, J=7.5 Hz, 2H), 1.35 (t, J=7.0 Hz, 3H), 1.17 (t, J=7.5 Hz, 3H). $^{13}$C NMR (126 MHz, MeOD) δ 176.16, 163.67, 144.80, 139.49, 133.53, 128.82, 128.46, 127.74, 127.09, 122.64, 119.77, 112.53, 62.30, 30.51, 14.58, 10.17. MS (ESI-TOF) for $C_{16}H_{18}N_2O_3S$ [M+H]⁺ calculated 319.1111; found, 319.1096.

Compound 6b. Pale orange solid (55 mg, 92%). MS (ESI-TOF) for $C_{16}H_{16}N_2O_2S$ [M+H]⁺ calculated 301.1005; found, 301.1028.

Ethyl 4-(2-propyl-1H-benzo[d]imidazol-1-yl)thiophene-2-carboxylate (6c). N-Acyl intermediate. Butyryl chloride (37.38 μL, 0.36 mmol) was used as reagent. Pale orange solid (84 mg, 84%). $^1$H NMR (500 MHz, Methanol-d₄) δ 7.51 (s, 1H), 7.39 (d, J=7.9 Hz, 1H), 7.21 (d, J=8.1 Hz, 1H), 7.15 (t, J=7.6 Hz, 1H), 6.96 (t, J=7.5 Hz, 1H), 6.80 (s, 1H), 4.31 (q, J=7.1 Hz, 2H), 2.36 (t, J=7.3 Hz, 2H), 1.70 (h, J=7.3 Hz, 2H), 1.35 (t, J=7.0 Hz, 3H), 0.99 (t, J=7.3 Hz, 3H). $^{13}$C NMR (126 MHz, MeOD) δ 175.34, 163.66, 144.83, 139.49, 133.58, 128.91, 128.37, 127.79, 127.04, 122.73, 119.91, 112.46, 62.31, 39.33, 20.27, 14.58, 14.04. MS (ESI-TOF) for $C_{17}H_{20}N_2O_3S$ [M+H]⁺ calculated 333.1267; found, 333.1278.

Compound 6c. Pale orange solid (59 mg, 94%). MS (ESI-TOF) for $C_{17}H_{18}N_2O_2S$ [M+H]⁺ calculated 315.1162; found, 315.1171.

Ethyl 4-(2-butyl-1H-benzo[d]imidazol-1-yl)thiophene-2-carboxylate (6d). N-Acyl intermediate. Valeroyl chloride (42.72 μL, 0.36 mmol) was used as reagent. Pale yellow solid (100 mg, 96%). $^1$H NMR (500 MHz, Methanol-d₄) δ 7.50 (s, 1H), 7.39 (d, J=7.9 Hz, 1H), 7.20 (d, J=8.0 Hz, 1H), 7.15 (t, J=7.6 Hz, 1H), 6.97 (t, J=7.5 Hz, 1H), 6.77 (s, 1H), 4.31 (q, J=7.0 Hz, 2H), 2.38 (t, J=7.5 Hz, 2H), 1.63 (p, J=7.5 Hz, 2H), 1.45-1.27 (m, 5H), 0.94 (t, J=7.3 Hz, 3H). $^{13}$C NMR (126 MHz, MeOD) δ 175.48, 163.67, 144.95, 139.40, 133.57, 129.09, 128.31, 127.77, 127.01, 122.86, 120.17, 112.30, 62.30, 37.23, 29.05, 23.44, 14.59, 14.17. MS (ESI-TOF) for $C_{18}H_{22}N_2O_3S$ [M+H]⁺ calculated 347.1424; found, 347.1445.

Compound 6d. Pale blue solid (64 mg, 97%). MS (ESI-TOF) for $C_{18}H_{20}N_2O_2S$ [M+H]⁺ calculated 329.1318; found, 329.1302.

Ethyl 4-(2-pentyl-1H-benzo[d]imidazol-1-yl)thiophene-2-carboxylate (6e). N-Acyl intermediate. Hexanoyl chloride (50.32 μL, 0.36 mmol) was used as reagent. Pale orange solid (95 mg, 88%). $^1$H NMR (500 MHz, DMSO-d₆) δ 9.22 (s, 1H), 7.56 (s, 1H), 7.49 (s, 1H), 7.42 (d, J=7.8 Hz, 1H), 7.19 (d, J=8.0 Hz, 1H), 7.09 (t, J=7.6 Hz, 1H), 6.96 (s, 1H), 6.90 (t, J=7.6 Hz, 1H), 4.27 (q, J=7.1 Hz, 2H), 2.31 (t, J=7.4 Hz, 2H), 1.57 (p, J=6.9 Hz, 2H), 1.28 (t, J=6.9 Hz, 7H), 0.86 (t, J=6.5 Hz, 3H). $^{13}$C NMR (126 MHz, DMSO-d₆) δ 171.77, 161.32, 142.90, 136.96, 131.42, 127.78, 127.08, 125.67, 125.63, 120.84, 117.62, 110.35, 60.89, 35.85, 30.92, 24.78, 21.92, 14.16, 13.85. MS (ESI-TOF) for $C_{19}H_{24}N_2O_3S$ [M+H]⁺ calculated 361.1580; found, 361.1538.

Compound 6e. Pale orange solid (64 mg, 93%). $^1$H NMR (500 MHz, DMSO-$d_6$) δ 8.30 (s, 1H), 8.01 (s, 1H), 7.64 (d, J=7.3 Hz, 1H), 7.32-7.10 (m, 3H), 4.34 (q, J=7.1 Hz, 2H), 2.77 (t, J=7.6 Hz, 2H), 1.69 (p, J=7.2 Hz, 2H), 1.32 (t, J=7.1 Hz, 3H), 1.29-1.21 (m, 4H), 0.82 (t, J=6.8 Hz, 3H). $^{13}$C NMR (126 MHz, DMSO-$d_6$) δ 160.82, 154.88, 142.09, 135.92, 133.68, 133.62, 131.37, 129.86, 122.52, 122.11, 118.63, 109.84, 61.44, 30.73, 26.84, 26.29, 21.71, 14.14, 13.74. MS (ESI-TOF) for $C_{19}H_{22}N_2O_2S$ [M+H]$^+$ calculated 343.1475; found, 343.1473.

Ethyl 4-(2-hexyl-1H-benzo[d]imidazol-1-yl)thiophene-2-carboxylate (6f). N-Acyl intermediate. Heptanoyl chloride (55.74 μL, 0.36 mmol) was used as reagent. Pale orange solid (95 mg, 85%). $^1$H NMR (500 MHz, Methanol-$d_4$) δ 7.49 (s, 1H), 7.39 (d, J=7.9 Hz, 1H), 7.21 (d, J=8.0 Hz, 1H), 7.15 (t, J=7.6 Hz, 1H), 6.97 (t, J=7.5 Hz, 1H), 6.75 (s, 1H), 4.31 (q, J=7.1 Hz, 2H), 2.37 (t, J=7.4 Hz, 2H), 1.64 (p, J=6.9 Hz, 2H), 1.40-1.26 (m, 9H), 0.94-0.85 (m, 3H). $^{13}$C NMR (126 MHz, MeOD) δ 175.48, 163.66, 144.99, 139.36, 133.58, 129.19, 128.25, 127.78, 126.99, 122.94, 120.33, 112.11, 62.30, 37.52, 32.74, 30.03, 26.89, 23.58, 14.59, 14.38. MS (ESI-TOF) for $C_{20}H_{26}N_2O_3S$ [M+H]$^+$ calculated 375.1737; found, 375.1722.

Compound 6f. Pale orange solid (65 mg, 91%). MS (ESI-TOF) for $C_{20}H_{24}N_2O_2S$ [M+H]$^+$ calculated 357.1631; found, 357.1615.

Ethyl 4-(2-octyl-1H-benzo[d]imidazol-1-yl)thiophene-2-carboxylate (6g). N-Acyl intermediate. Nonanoyl chloride (64.90 μL, 0.36 mmol) was used as reagent. Pale orange solid (94 mg, 78%). $^1$H NMR (500 MHz, Methanol-$d_4$) δ 7.49 (s, 1H), 7.39 (d, J=7.9 Hz, 1H), 7.21 (d, J=7.9 Hz, 1H), 7.15 (t, J=7.6 Hz, 1H), 6.97 (t, J=7.5 Hz, 1H), 6.76 (s, 1H), 4.31 (q, J=7.1 Hz, 2H), 2.37 (t, J=7.4 Hz, 2H), 1.75-1.55 (m, 2H), 1.40-1.23 (m, 13H), 0.89 (t, J=6.4 Hz, 3H). $^{13}$C NMR (126 MHz, MeOD) δ 175.49, 163.65, 144.99, 139.38, 133.58, 129.20, 128.24, 127.79, 126.99, 122.95, 120.34, 112.09, 62.29, 37.51, 33.00, 30.47, 30.35, 30.32, 26.93, 23.71, 14.60, 14.43. MS (ESI-TOF) for $C_{22}H_{30}N_2O_3S$ [M+H]$^+$ calculated 403.2050; found, 403.2032.

Compound 6g. Pale orange solid (70 mg, 91%). $^1$H NMR (500 MHz, Methanol-$d_4$) δ 8.04 (s, 1H), 7.91 (s, 1H), 7.64 (d, J=7.6 Hz, 1H), 7.32-7.23 (m, 2H), 7.19 (d, J=7.6 Hz, 1H), 4.40 (q, J=7.1 Hz, 2H), 2.86 (t, J=7.6 Hz, 2H), 1.72 (p, J=7.3 Hz, 2H), 1.39 (t, J=7.0 Hz, 3H), 1.34-1.18 (m, 10H), 0.87 (t, J=6.8 Hz, 3H). $^{13}$C NMR (126 MHz, MeOD) δ 162.65, 157.02, 142.71, 137.29, 136.33, 134.94, 132.15, 130.74, 124.47, 124.10, 119.28, 111.16, 62.92, 32.96, 30.13, 30.08, 28.64, 28.24, 23.67, 14.57, 14.42. MS (ESI-TOF) for $C_{22}H_{28}N_2O_2S$ [M+H]$^+$ calculated 385.1944; found, 385.1926.

Ethyl 4-(2-nonyl-1H-benzo[d]imidazol-1-yl)thiophene-2-carboxylate (6h). N-Acyl intermediate. Decanoyl chloride (74.71 μL, 0.36 mmol) was used as reagent. Pale orange solid (100 mg, 80%). $^1$H NMR (500 MHz, Methanol-$d_4$) δ 7.49 (s, 1H), 7.39 (d, J=7.9 Hz, 1H), 7.21 (d, J=8.0 Hz, 1H), 7.15 (t, J=7.6 Hz, 1H), 6.97 (t, J=7.5 Hz, 1H), 6.76 (s, 1H), 4.31 (q, J=7.1 Hz, 2H), 2.37 (t, J=7.4 Hz, 2H), 1.69-1.56 (m, 2H), 1.42-1.19 (m, 15H), 0.89 (t, J=6.3 Hz, 3H). $^{13}$C NMR (126 MHz, MeOD) δ 175.49, 163.65, 144.98, 139.39, 133.59, 129.19, 128.25, 127.80, 126.99, 122.94, 120.32, 112.11, 62.29, 37.50, 33.04, 30.60, 30.51, 30.41, 30.33, 26.93, 23.73, 14.60, 14.44. MS (ESI-TOF) for $C_{23}H_{32}N_2O_3S$ [M+H]$^+$ calculated 417.2206; found, 417.2192.

Compound 6h. Pale orange solid (72 mg, 90%). $^1$H NMR (500 MHz, Methanol-$d_4$) δ 8.04 (s, 1H), 7.91 (s, 1H), 7.64 (d, J=7.5 Hz, 1H), 7.32-7.23 (m, 2H), 7.19 (d, J=7.6 Hz, 1H), 4.40 (q, J=7.0 Hz, 2H), 2.86 (t, J=7.6 Hz, 2H), 1.72 (p, J=7.3 Hz, 2H), 1.39 (t, J=7.0 Hz, 3H), 1.33-1.18 (m, 12H), 0.88 (t, J=6.7 Hz, 3H). $^{13}$C NMR (126 MHz, MeOD) δ 162.65, 157.02, 142.73, 137.29, 136.33, 134.94, 132.15, 130.73, 124.47, 124.09, 119.28, 111.16, 62.92, 32.99, 30.40, 30.37, 30.10, 28.64, 28.24, 23.72, 14.57, 14.42. MS (ESI-TOF) for $C_{23}H_{30}N_2O_2S$ [M+H]$^+$ calculated 399.2101; found, 399.2123.

Ethyl 4-(2-undecyl-1H-benzo[d]imidazol-1-yl)thiophene-2-carboxylate (6i). N-Acyl intermediate. Lauroyl chloride (83.25 μL, 0.36 mmol) was used as reagent. Pale orange solid (105 mg, 79%). $^1$H NMR (500 MHz, Methanol-$d_4$) δ 7.49 (s, 1H), 7.39 (d, J=7.9 Hz, 1H), 7.21 (d, J=8.0 Hz, 1H), 7.15 (t, J=7.6 Hz, 1H), 6.97 (t, J=7.5 Hz, 1H), 6.76 (s, 1H), 4.31 (q, J=7.1 Hz, 2H), 2.37 (t, J=7.3 Hz, 2H), 1.74-1.54 (m, 2H), 1.44-1.20 (m, 19H), 0.89 (t, J=6.5 Hz, 3H). $^{13}$C NMR (126 MHz, MeOD) δ 175.49, 163.64, 144.97, 139.39, 133.58, 129.17, 128.25, 127.80, 126.99, 122.93, 120.30, 112.12, 62.29, 37.50, 33.08, 30.73, 30.63, 30.49, 30.48, 30.32, 26.92, 23.74, 14.61, 14.45. MS (ESI-TOF) for $C_{25}H_{36}N_2O_3S$ [M+H]$^+$ calculated 445.2519; found, 445.2510.

Compound 6i. Pale orange solid (76 mg, 89%). $^1$H NMR (500 MHz, Methanol-$d_4$) δ 8.03 (s, 1H), 7.90 (s, 1H), 7.64 (d, J=7.5 Hz, 1H), 7.30-7.22 (m, 2H), 7.19 (d, J=7.6 Hz, 1H), 4.39 (q, J=7.0 Hz, 2H), 2.86 (t, J=7.6 Hz, 2H), 1.72 (p, J=7.3 Hz, 2H), 1.39 (t, J=7.1 Hz, 3H), 1.33-1.18 (m, 16H), 0.89 (t, J=6.6 Hz, 3H). $^{13}$C NMR (126 MHz, MeOD) δ 162.63, 157.01, 142.72, 137.28, 136.32, 134.93, 132.14, 130.71, 124.46, 124.09, 119.29, 111.15, 62.91, 33.05, 30.68, 30.46, 30.43, 30.09, 28.63, 28.24, 23.73, 14.58, 14.44. MS (ESI-TOF) for $C_{25}H_{34}N_2O_2S$ [M+H]$^+$ calculated 427.2414; found, 427.2408.

Ethyl 4-(2-tridecyl-1H-benzo[d]imidazol-1-yl)thiophene-2-carboxylate (6j). N-Acyl intermediate. Myristoyl chloride (97.86 μL, 0.36 mmol) was used as reagent. Pale orange solid (108 mg, 76%). $^1$H NMR (500 MHz, Methanol-$d_4$) δ 7.49 (s, 1H), 7.39 (d, J=7.8 Hz, 1H), 7.21 (d, J=8.0 Hz, 1H), 7.15 (t, J=7.6 Hz, 1H), 6.97 (t, J=7.5 Hz, 1H), 6.76 (s, 1H), 4.31 (q, J=7.0 Hz, 2H), 2.37 (t, J=7.3 Hz, 2H), 1.76-1.53 (m, 2H), 1.39-1.20 (m, 23H), 0.90 (t, J=6.4 Hz, 3H). $^{13}$C NMR (126 MHz, MeOD) δ 175.50, 163.65, 144.99, 139.40, 133.59, 129.19, 128.25, 127.80, 126.99, 122.95, 120.32, 112.11, 62.29, 37.50, 33.09, 30.80, 30.76, 30.71, 30.63, 30.48, 30.32, 26.92, 23.74, 14.61, 14.44. MS (ESI-TOF) for $C_{27}H_{40}N_2O_3S$ [M+H]$^+$ calculated 473.2832; found, 473.2830.

Compound 6j. Pale orange solid (82 mg, 90%). $^1$H NMR (500 MHz, Methanol-$d_4$) δ 8.03 (s, 1H), 7.90 (s, 1H), 7.64 (d, J=7.6 Hz, 1H), 7.32-7.23 (m, 2H), 7.19 (d, J=7.6 Hz, 1H), 4.40 (q, J=7.1 Hz, 2H), 2.86 (t, J=7.6 Hz, 2H), 1.72 (p, J=7.4 Hz, 2H), 1.39 (t, J=7.1 Hz, 3H), 1.34-1.19 (m, 20H), 0.89 (t, J=6.6 Hz, 3H). $^{13}$C NMR (126 MHz, MeOD) δ 162.63, 157.01, 142.71, 137.28, 136.33, 134.93, 132.14, 130.72, 124.47, 124.10, 119.28, 111.16, 62.91, 33.07, 30.78, 30.74, 30.71, 30.67, 30.47, 30.42, 30.08, 28.63, 28.23, 23.74, 14.58, 14.44. MS (ESI-TOF) for $C_{27}H_{38}N_2O_2S$ [M+H]$^+$ calculated 455.2727; found, 455.2715.

Ethyl 4-(2-pentadecyl-1H-benzo[d]imidazol-1-yl)thiophene-2-carboxylate (6k). N-Acyl intermediate. Palmitoyl chloride (109.22 μL, 0.36 mmol) was used as reagent. Pale orange solid (117 mg, 78%). $^1$H NMR (500 MHz, Methanol-$d_4$) δ 7.49 (s, 1H), 7.39 (d, J=7.9 Hz, 1H), 7.21 (d, J=8.0 Hz, 1H), 7.15 (t, J=7.5 Hz, 1H), 6.97 (t, J=7.5 Hz, 1H), 6.76 (s, 1H), 4.31 (q, J=7.0 Hz, 2H), 2.37 (t, J=7.3 Hz, 2H), 1.71-1.56 (m, 2H), 1.41-1.20 (m, 27H), 0.90 (t, J=6.3 Hz, 3H). $^{13}$C NMR (126 MHz, MeOD) δ 175.48, 163.64, 144.97, 139.38, 133.59, 129.17, 128.25, 127.79, 126.98, 122.93, 120.30, 112.10, 62.29, 37.50, 33.08, 30.80, 30.77, 30.71, 30.63, 30.48, 30.31, 26.92, 23.74, 14.62, 14.45. MS (ESI-TOF) for $C_{29}H_{44}N_2O_3S$ [M+H]$^+$ calculated 501.3145; found, 501.3132.

Compound 6k. Pale orange solid (86 mg, 89%). $^1$H NMR (500 MHz, Methanol-d$_4$) δ 8.03 (s, 1H), 7.91 (s, 1H), 7.64 (d, J=7.6 Hz, 1H), 7.32-7.23 (m, 2H), 7.19 (d, J=7.6 Hz, 1H), 4.40 (q, J=7.0 Hz, 2H), 2.86 (t, J=7.6 Hz, 2H), 1.72 (p, J=7.2 Hz, 2H), 1.39 (t, J=7.1 Hz, 3H), 1.33-1.19 (m, 24H), 0.89 (t, J=6.4 Hz, 3H). $^{13}$C NMR (126 MHz, MeOD) δ 162.64, 157.01, 142.73, 137.29, 136.33, 134.94, 132.14, 130.72, 124.47, 124.09, 119.29, 111.16, 62.91, 33.08, 30.79, 30.76, 30.70, 30.67, 30.48, 30.41, 30.08, 28.63, 28.24, 23.74, 14.59, 14.45. MS (ESI-TOF) for $C_{29}H_{42}N_2O_2S$ [M+H]$^+$ calculated 483.3040; found, 483.3036.

Ethyl 4-(2-heptadecyl-1H-benzo[d]imidazol-1-yl)thiophene-2-carboxylate (6l). N-Acyl intermediate. Stearoyl chloride (121.57 µL, 0.36 mmol) was used as reagent. Pale orange solid (119 mg, 75%). $^1$H NMR (500 MHz, Methanol-d$_4$) δ 7.49 (s, 1H), 7.39 (d, J=7.6 Hz, 1H), 7.21 (d, J=7.9 Hz, 1H), 7.15 (t, J=7.4 Hz, 1H), 6.97 (t, J=7.4 Hz, 1H), 6.76 (s, 1H), 4.31 (q, J=7.0 Hz, 2H), 2.37 (t, J=7.3 Hz, 2H), 1.73-1.56 (m, 2H), 1.41-1.21 (m, 31H), 0.90 (t, J=6.5 Hz, 3H). $^{13}$C NMR (126 MHz, MeOD) δ 175.49, 163.64, 144.98, 139.39, 133.59, 129.19, 128.25, 127.80, 126.98, 122.94, 120.32, 112.10, 62.29, 37.50, 33.08, 30.79, 30.70, 30.62, 30.48, 30.31, 26.92, 23.74, 14.62, 14.44. MS (ESI-TOF) for $C_{31}H_{48}N_2O_3S$ [M+H]$^+$ calculated 529.3458; found, 529.3435.

Compound 6l. Pale orange solid (90 mg, 88%). $^1$H NMR (500 MHz, Methanol-d$_4$) δ 8.03 (s, 1H), 7.91 (s, 1H), 7.64 (d, J=7.5 Hz, 1H), 7.32-7.22 (m, 2H), 7.19 (d, J=7.5 Hz, 1H), 4.40 (q, J=7.0 Hz, 2H), 2.86 (t, J=7.6 Hz, 2H), 1.72 (p, J=7.3 Hz, 2H), 1.39 (t, J=7.0 Hz, 3H), 1.36-1.16 (m, 28H), 0.89 (t, J=6.4 Hz, 3H). $^{13}$C NMR (126 MHz, MeOD) δ 162.63, 157.01, 142.73, 137.29, 136.33, 134.94, 132.14, 130.71, 124.47, 124.10, 119.29, 111.16, 62.91, 33.08, 30.79, 30.75, 30.69, 30.66, 30.48, 30.41, 30.08, 28.63, 28.24, 23.74, 14.59, 14.45. MS (ESI-TOF) for $C_{31}H_{46}N_2O_2S$ [M+H]$^+$ calculated 511.3353; found, 511.3338.

Ethyl 4-(2-isopentyl-1H-benzo[d]imidazol-1-yl)thiophene-2-carboxylate (6m). To a solution of compound 5 (78.69 mg, 0.3 mmol) in anhydrous DCM (5 mL) were added 4-methylvaleric acid (45.31 µL, 0.36 mmol), HATU (114.07 mg, 0.3 mmol) and DIPEA (156.77 µL, 0.9 mmol). The reaction mixture was stirred at room temperature for 12 h. The mixture was diluted with water and extracted with DCM (3×10 mL). The combined organic layer was dried over Na$_2$SO$_4$ and concentrated under reduced pressure. The crude product was purified by flash chromatography (20% EtOAc/hexanes) to obtain the N-acyl intermediate as a pale yellow solid (89 mg, 82%). MS (ESI-TOF) for $C_{19}H_{24}N_2O_3S$ [M+H]$^+$ calculated 361.1580; found, 361.1590. The N-acyl intermediate (72.09 mg, 0.2 mmol) was dissolved in acetic acid (2 mL) and stirred at 80° C. for 12 h. The solvent was removed under reduced pressure, and the crude material was purified by flash chromatography (20% EtOAc/hexanes) to obtain the desired product 6m as pale orange solid (61 mg, 89%). MS (ESI-TOF) for $C_{19}H_{22}N_2O_2S$ [M+H]$^+$ calculated 343.1475; found, 343.1468.

Compound 6n was synthesized similarly as compound 6m. Ethyl 4-(2-(3-methylbut-3-en-1-yl)-1H-benzo[d]imidazol-1-yl)thiophene-2-carboxylate (6n). N-Acyl intermediate. 4-Methylpent-4-enoic acid (41.09 mg, 0.36 mmol) was used as reagent. Pale yellow solid (95 mg, 88%). $^1$H NMR (500 MHz, DMSO-d$_6$) δ 9.29 (s, 1H), 7.52 (d, J=12.4 Hz, 2H), 7.39 (d, J=7.8 Hz, 1H), 7.20 (d, J=8.0 Hz, 1H), 7.09 (t, J=7.6 Hz, 1H), 7.00 (s, 1H), 6.89 (t, J=7.6 Hz, 1H), 4.71 (s, 2H), 4.27 (q, J=7.1 Hz, 2H), 2.49-2.45 (m, 2H), 2.28 (t, J=7.6 Hz, 2H), 1.72 (s, 3H), 1.28 (t, J=7.1 Hz, 3H). $^{13}$C NMR (126 MHz, DMSO-d$_6$) δ 171.21, 161.33, 144.64, 142.74, 137.14, 131.41, 127.44, 127.23, 125.80, 125.75, 120.64, 117.23, 110.63, 110.08, 60.91, 34.14, 32.82, 22.41, 14.16. MS (ESI-TOF) for $C_{19}H_{22}N_2O_3S$ [M+H]$^+$ calculated 359.1424; found, 359.1420.

Compound 6n. Pale orange solid (63 mg, 93%). $^1$H NMR (500 MHz, Methanol-d$_4$) δ 8.05 (s, 1H), 7.92 (s, 1H), 7.65 (d, J=7.7 Hz, 1H), 7.33-7.23 (m, 2H), 7.20 (d, J=7.7 Hz, 1H), 4.69 (s, 1H), 4.60 (s, 1H), 4.40 (q, J=7.1 Hz, 2H), 3.07-2.96 (m, 2H), 2.44 (t, J=7.8 Hz, 2H), 1.66 (s, 3H), 1.39 (t, J=7.1 Hz, 3H). $^{13}$C NMR (126 MHz, MeOD) δ 162.65, 156.41, 145.21, 142.72, 137.25, 136.34, 134.84, 132.18, 130.76, 124.53, 124.13, 119.32, 111.75, 111.19, 62.92, 36.67, 27.13, 22.28, 14.55. MS (ESI-TOF) for $C_{19}H_{20}N_2O_2S$ [M+H]$^+$ calculated 341.1318; found, 341.1308.

Compounds 7a-n were synthesized similarly as compound 2a.

4-(2-Methyl-1H-benzo[d]imidazol-1-yl)thiophene-2-carboxamide (7a). Compound 6a (28.63 mg, 0.1 mmol) was used as reagent. White solid (23 mg, 89%). $^1$H NMR (500 MHz, Methanol-d$_4$) δ 7.96 (s, 1H), 7.86 (s, 1H), 7.62 (d, J=6.5 Hz, 1H), 7.31-7.22 (m, 3H), 2.55 (s, 3H). $^{13}$C NMR (126 MHz, MeOD) δ 165.34, 153.42, 142.68, 141.47, 137.20, 134.65, 128.62, 127.91, 124.43, 124.08, 119.17, 111.28, 13.97. MS (ESI-TOF) for $C_{13}H_{11}N_3OS$ [M+H]$^+$ calculated 258.0696; found, 258.0677.

4-(2-Ethyl-1H-benzo[d]imidazol-1-yl)thiophene-2-carboxamide (7b). Compound 6b (30.04 mg, 0.1 mmol) was used as reagent. White solid (24 mg, 88%). $^1$H NMR (500 MHz, DMSO-d$_6$) δ 8.11 (d, J=14.1 Hz, 2H), 7.95 (s, 1H), 7.71-7.57 (m, 2H), 7.31-7.16 (m, 3H), 2.82 (q, J=7.5 Hz, 2H), 1.27 (t, J=7.5 Hz, 3H). $^{13}$C NMR (126 MHz, DMSO-d$_6$) δ 162.09, 155.76, 142.01, 140.83, 135.78, 132.88, 126.87, 126.33, 122.57, 122.13, 118.69, 110.01, 20.61, 11.45. MS (ESI-TOF) for $C_{14}H_{13}N_3OS$ [M+H]$^+$ calculated 272.0852; found, 272.0838.

4-(2-Propyl-1H-benzo[d]imidazol-1-yl)thiophene-2-carboxamide (7c). Compound 6c (31.44 mg, 0.1 mmol) was used as reagent. White solid (26 mg, 91%). $^1$H NMR (500 MHz, DMSO-d$_6$) δ 8.11 (d, J=10.8 Hz, 2H), 7.94 (s, 1H), 7.71-7.58 (m, 2H), 7.28-7.12 (m, 3H), 2.78 (t, J=7.4 Hz, 2H), 1.73 (h, J=7.4 Hz, 2H), 0.92 (t, J=7.4 Hz, 3H). $^{13}$C NMR (126 MHz, DMSO-d$_6$) δ 162.09, 154.62, 142.04, 140.85, 135.74, 132.91, 127.01, 126.39, 122.55, 122.15, 118.67, 110.03, 28.90, 20.12, 13.72. MS (ESI-TOF) for $C_{15}H_{15}N_3OS$ [M+H]$^+$ calculated 286.1009; found, 286.1000.

4-(2-Butyl-1H-benzo[d]imidazol-1-yl)thiophene-2-carboxamide (7d). Compound 6d (32.84 mg, 0.1 mmol) was used as reagent. White solid (28 mg, 94%). $^1$H NMR (500 MHz, DMSO-d$_6$) δ 8.12 (s, 1H), 8.10 (s, 1H), 7.94 (s, 1H), 7.68-7.59 (m, 2H), 7.28-7.18 (m, 3H), 2.80 (t, J=7.5 Hz, 2H), 1.68 (p, J=7.5 Hz, 2H), 1.32 (h, J=7.3 Hz, 2H), 0.84 (t, J=7.4 Hz, 3H). $^{13}$C NMR (126 MHz, DMSO-d$_6$) δ 162.09, 154.80, 142.04, 140.85, 135.74, 132.92, 127.04, 126.40, 122.54, 122.15, 118.66, 110.02, 28.87, 26.58, 21.69, 13.60. MS (ESI-TOF) for C$_{16}$H$_{17}$N$_3$OS [M+H]$^+$ calculated 300.1165; found, 300.1176.

4-(2-Pentyl-1H-benzo[d]imidazol-1-yl)thiophene-2-carboxamide (7e). Compound 6e (34.24 mg, 0.1 mmol) was used as reagent. White solid (28 mg, 89%). $^1$H NMR (500 MHz, DMSO-d$_6$) δ 8.11 (d, J=14.3 Hz, 2H), 7.94 (s, 1H), 7.69-7.57 (m, 2H), 7.29-7.16 (m, 3H), 2.80 (t, J=7.5 Hz, 2H), 1.69 (p, J=7.2 Hz, 2H), 1.34-1.18 (m, 4H), 0.82 (t, J=6.8 Hz, 3H). $^{13}$C NMR (126 MHz, DMSO-d$_6$) δ 162.08, 154.81, 142.03, 140.85, 135.74, 132.92, 127.02, 126.39, 122.53, 122.14, 118.66, 110.01, 30.74, 26.87, 26.38, 21.71, 13.75. MS (ESI-TOF) for C$_{17}$H$_{19}$N$_3$OS [M+H]$^+$ calculated 314.1322; found, 314.1341.

4-(2-Hexyl-1H-benzo[d]imidazol-1-yl)thiophene-2-carboxamide (7f). Compound 6f (35.65 mg, 0.1 mmol) was used as reagent. White solid (28 mg, 86%). $^1$H NMR (500 MHz, DMSO-d$_6$) δ 8.10 (d, J=14.1 Hz, 2H), 7.94 (s, 1H), 7.71-7.58 (m, 2H), 7.29-7.18 (m, 3H), 2.80 (t, J=7.5 Hz, 2H), 1.68 (p, J=7.4 Hz, 2H), 1.35-1.15 (m, 6H), 0.82 (t, J=6.5 Hz, 3H). $^{13}$C NMR (126 MHz, DMSO-d$_6$) δ 162.07, 154.83, 142.04, 140.86, 135.73, 132.92, 127.01, 126.40, 122.53, 122.15, 118.66, 110.01, 30.82, 28.20, 26.88, 26.69, 21.90, 13.89. MS (ESI-TOF) for C$_{18}$H$_{21}$N$_3$OS [M+H]$^+$ calculated 328.1478; found, 328.1479.

4-(2-Octyl-1H-benzo[d]imidazol-1-yl)thiophene-2-carboxamide (7g). Compound 6g (38.45 mg, 0.1 mmol) was used as reagent. Green solid (30 mg, 84%). $^1$H NMR (500 MHz, Methanol-d$_4$) δ 7.96 (s, 1H), 7.84 (s, 1H), 7.64 (d, J=7.4 Hz, 1H), 7.34-7.16 (m, 3H), 2.88 (t, J=7.7 Hz, 2H), 1.72 (p, J=7.5 Hz, 2H), 1.42-1.14 (m, 10H), 0.87 (t, J=6.9 Hz, 3H). $^{13}$C NMR (126 MHz, CDCl$_3$) δ 162.65, 155.45, 142.39, 139.31, 136.30, 134.12, 127.02, 126.95, 123.15, 122.92, 119.37, 109.86, 31.93, 29.48, 29.31, 29.23, 27.87, 27.84, 22.77, 14.23. MS (ESI-TOF) for C$_{20}$H$_{25}$N$_3$OS [M+H]$^+$ calculated 356.1791; found, 356.1778.

4-(2-Nonyl-1H-benzo[d]imidazol-1-yl)thiophene-2-carboxamide (7h). Compound 6h (39.86 mg, 0.1 mmol) was used as reagent. Pale green solid (32 mg, 87%). $^1$H NMR (500 MHz, Methanol-d$_4$) δ 7.96 (s, 1H), 7.84 (s, 1H), 7.64 (d, J=7.5 Hz, 1H), 7.32-7.19 (m, 3H), 2.88 (t, J=7.7 Hz, 2H), 1.72 (p, J=7.5 Hz, 2H), 1.39-1.17 (m, 12H), 0.88 (t, J=6.9 Hz, 3H). $^{13}$C NMR (126 MHz, CDCl$_3$) δ 162.58, 155.44, 142.43, 139.30, 136.32, 134.15, 127.01, 126.95, 123.13, 122.91, 119.39, 109.86, 31.99, 29.54, 29.49, 29.38, 29.36, 27.88, 27.86, 22.80, 14.24. MS (ESI-TOF) for C$_{21}$H$_{27}$N$_3$OS [M+H]$^+$ calculated 370.1948; found, 370.1943.

4-(2-Undecyl-1H-benzo[d]imidazol-1-yl)thiophene-2-carboxamide (7i). Compound 6i (42.66 mg, 0.1 mmol) was used as reagent. Green solid (35 mg, 88%). $^1$H NMR (500 MHz, Methanol-d$_4$) δ 7.96 (s, 1H), 7.84 (s, 1H), 7.64 (d, J=7.4 Hz, 1H), 7.31-7.19 (m, 3H), 2.88 (t, J=7.7 Hz, 2H), 1.73 (p, J=7.5 Hz, 2H), 1.36-1.19 (m, 16H), 0.89 (t, J=6.9 Hz, 3H). $^{13}$C NMR (126 MHz, CDCl$_3$) δ 162.55, 155.44, 142.45, 139.27, 136.32, 134.17, 127.00, 126.95, 123.13, 122.91, 119.41, 109.85, 32.04, 29.74, 29.59, 29.50, 29.47, 29.38, 27.89, 22.83, 14.26. MS (ESI-TOF) for C$_{23}$H$_{31}$N$_3$OS [M+H]$^+$ calculated 398.2261; found, 398.2259.

4-(2-Tridecyl-1H-benzo[d]imidazol-1-yl)thiophene-2-carboxamide (7j). Compound 6j (45.47 mg, 0.1 mmol) was used as reagent. Green solid (38 mg, 89%). $^1$H NMR (500 MHz, Methanol-d$_4$) δ 7.95 (s, 1H), 7.84 (s, 1H), 7.64 (d, J=7.4 Hz, 1H), 7.32-7.19 (m, 3H), 2.87 (t, J=7.7 Hz, 2H), 1.73 (p, J=7.5 Hz, 2H), 1.37-1.16 (m, 20H), 0.89 (t, J=6.8 Hz, 3H). $^{13}$C NMR (126 MHz, CDCl$_3$) δ 162.56, 155.44, 142.44, 139.28, 136.32, 134.16, 127.00, 126.95, 123.13, 122.91, 119.40, 109.85, 32.06, 29.82, 29.79, 29.74, 29.60, 29.50, 29.38, 27.89, 22.84, 14.27. MS (ESI-TOF) for C$_{25}$H$_{35}$N$_3$OS [M+H]$^+$ calculated 426.2574; found, 426.2567.

4-(2-Pentadecyl-1H-benzo[d]imidazol-1-yl)thiophene-2-carboxamide (7k). Compound 6k (48.27 mg, 0.1 mmol) was used as reagent. Green solid (40 mg, 88%). $^1$H NMR (500 MHz, Methanol-d$_4$) δ 7.96 (s, 1H), 7.84 (s, 1H), 7.64 (d, J=7.5 Hz, 1H), 7.32-7.19 (m, 3H), 2.88 (t, J=7.7 Hz, 2H), 1.73 (p, J=7.5 Hz, 2H), 1.41-1.17 (m, 24H), 0.89 (t, J=6.8 Hz, 3H). $^{13}$C NMR (126 MHz, CDCl$_3$) δ 162.54, 155.44, 142.45, 139.26, 136.32, 134.17, 127.00, 126.95, 123.13, 122.91, 119.41, 109.85, 32.07, 29.84, 29.83, 29.80, 29.75, 29.61, 29.51, 29.39, 27.89, 22.84, 14.27. MS (ESI-TOF) for C$_{27}$H$_{39}$N$_3$OS [M+H]$^+$ calculated 454.2887; found, 454.2879.

4-(2-Heptadecyl-1H-benzo[d]imidazol-1-yl)thiophene-2-carboxamide (7l). Compound 6l (51.08 mg, 0.1 mmol) was used as reagent. Green solid (42 mg, 87%). $^1$H NMR (500 MHz, Methanol-d$_4$) δ 7.95 (s, 1H), 7.84 (s, 1H), 7.64 (d, J=7.5 Hz, 1H), 7.34-7.17 (m, 3H), 2.87 (t, J=7.7 Hz, 2H), 1.73 (p, J=7.5 Hz, 2H), 1.41-1.16 (m, 28H), 0.89 (t, J=6.7 Hz, 3H). $^{13}$C NMR (126 MHz, CDCl$_3$) δ 162.56, 155.44, 142.44, 139.27, 136.32, 134.16, 127.00, 126.95, 123.13, 122.91, 119.40, 109.85, 32.07, 29.85, 29.81, 29.75, 29.61, 29.51, 29.39, 27.89, 27.87, 22.84, 14.27. MS (ESI-TOF) for C$_{29}$H$_{43}$N$_3$OS [M+H]$^+$ calculated 482.3200; found, 482.3187.

4-(2-Isopentyl-1H-benzo[d]imidazol-1-yl)thiophene-2-carboxamide (7m). Compound 6m (34.25 mg, 0.1 mmol) was used as reagent. Brown solid (28 mg, 89%). $^1$H NMR (500 MHz, Methanol-d$_4$) δ 7.99-7.95 (m, 1H), 7.86-7.83 (m, 1H), 7.64 (d, J=7.0 Hz, 1H), 7.32-7.19 (m, 3H), 2.92-2.83 (m, 2H), 1.66-1.50 (m, 3H), 0.87 (d, J=6.4 Hz, 6H). $^{13}$C NMR (126 MHz, MeOD) δ 165.27, 157.19, 142.71, 141.57, 137.31, 134.61, 129.16, 128.20, 124.42, 124.05, 119.23, 111.25, 37.82, 28.91, 26.39, 22.53. MS (ESI-TOF) for C$_{17}$H$_{19}$N$_3$OS [M+H]$^+$ calculated 314.1322; found, 314.1310.

4-(2-(3-Methylbut-3-en-1-yl)-1H-benzo[d]imidazol-1-yl)thiophene-2-carboxamide (7n). Compound 6n (34.04 mg, 0.1 mmol) was used as reagent. White solid (29 mg, 93%). $^1$H NMR (500 MHz, Methanol-d$_4$) δ 7.98 (s, 1H), 7.85 (s, 1H), 7.65 (d, J=7.2 Hz, 1H), 7.37-7.18 (m, 3H), 4.69 (s, 1H), 4.61 (s, 1H), 3.07-2.99 (m, 2H), 2.44 (t, J=7.8 Hz, 2H), 1.67 (s, 3H). $^{13}$C NMR (126 MHz, MeOD) δ 165.27, 156.42, 145.19, 142.70, 141.58, 137.27, 134.53, 129.17, 128.23, 124.49, 124.10, 119.29, 111.75, 111.30, 36.68, 27.15, 22.25. MS (ESI-TOF) for C$_{17}$H$_{17}$N$_3$OS [M+H]$^+$ calculated 312.1165; found, 312.1149.

Example 3: General Procedure for the Synthesis of Compounds 8, 9, 10, 11a-c and 13a-c

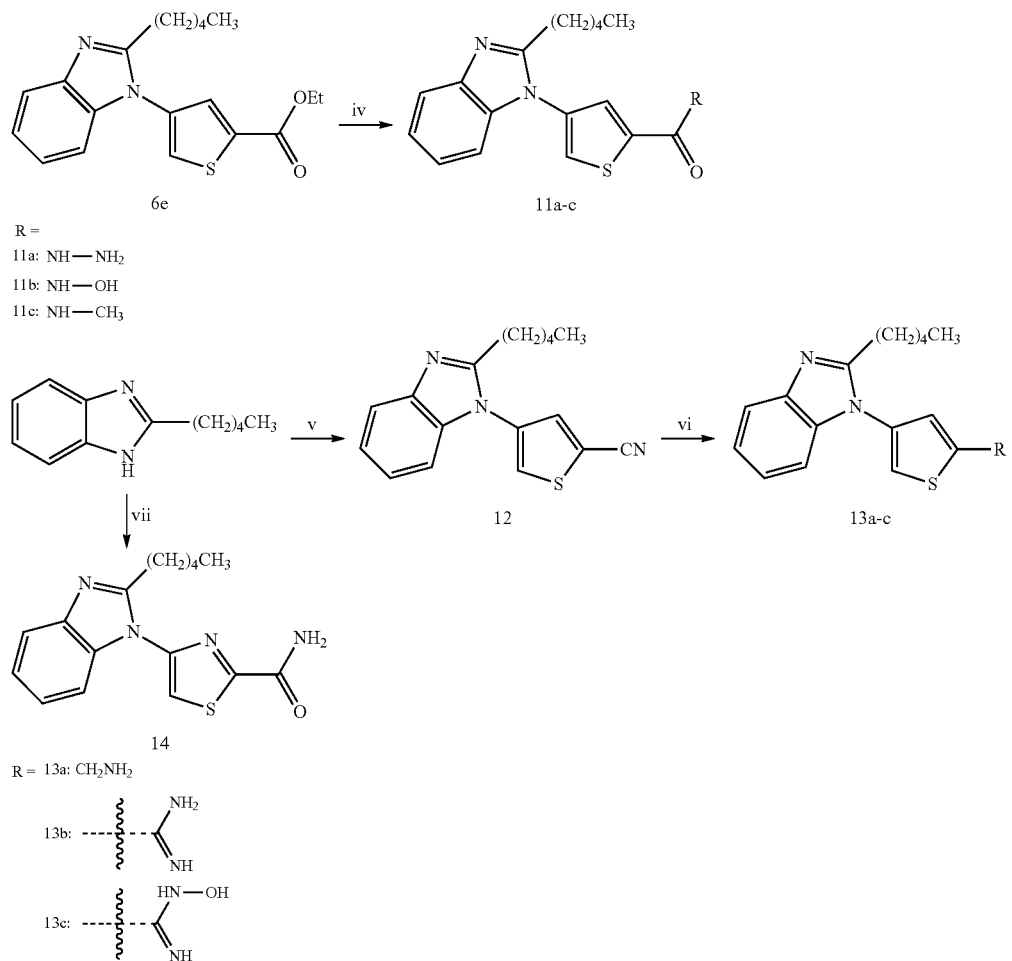

Reagents and Conditions
(iv) hydrazine hydrate, EtOH, 80° C., 24 h (for 11a); hydroxylamine hydrochloride, KOH, MeOH, 65° C., 12 h (for 11b); methylamine solution (2 M in MeOH), MeOH, 65° C., 12 h (for 11c);
(v) 4-bromothiophene-2-carbonitrile, CuI, L-proline, $K_2CO_3$, DMF, microwave, 120° C., 1 h;
(vi) LiAlH$_4$, THF, 80° C., 2 h (for 13a); 7 N NH$_3$ in MeOH, 60° C., 12 h (for 13b); hydroxylamine hydrochloride, EtOH, DIPEA, 80° C., 4 h (for 13c);
(vii) 4-bromothiazole-2-carboxamide, CuI, L-proline, $K_2CO_3$, DMF, microwave, 120° C., 1 h.

Compound 11a was synthesized similarly as compound 2b.
4-(2-Pentyl-1H-benzo[d]imidazol-1-yl)thiophene-2-carbohydrazide (11a). Compound 6e (34.25 mg, 0.1 mmol) was used as reagent. White solid (26 mg, 79%). $^1$H NMR (500 MHz, Methanol-d$_4$) δ 7.95 (s, 1H), 7.76 (s, 1H), 7.64 (d, J=7.4 Hz, 1H), 7.33 7.17 (m, 3H), 2.86 (t, J=7.7 Hz, 2H), 1.81-1.66 (m, 2H), 1.42-1.22 (m, 4H), 0.86 (t, J=6.7 Hz, 3H). $^{13}$C NMR (126 MHz, MeOD) δ 163.08, 157.00, 142.71, 139.82, 137.29, 134.62, 128.39, 127.13, 124.42, 124.06, 119.25, 111.25, 32.43, 28.38, 28.30, 23.23, 14.19. MS (ESI-TOF) for $C_{17}H_{20}N_4OS$ [M+H]$^+$ calculated 329.1431; found, 329.1461.

Compound 11b was synthesized similarly as compound 2c.
N-Hydroxy-4-(2-pentyl-1H-benzo[d]imidazol-1-yl)thiophene-2-carboxamide (11b). Compound 6e (34.25 mg, 0.1 mmol) was used as reagent. White solid (24 mg, 73%). $^1$H NMR (500 MHz, Methanol-d$_4$) δ 7.97 (s, 1H), 7.74-7.58 (m, 2H), 7.34-7.13 (m, 3H), 2.86 (t, J=7.7 Hz, 2H), 1.82-1.66 (m, 2H), 1.36-1.21 (m, 4H), 0.87 (t, J=6.7 Hz, 3H). $^{13}$C NMR (126 MHz, MeOD) δ 157.01, 142.70, 138.84, 138.81, 137.29, 134.59, 128.40, 126.98, 124.44, 124.07, 119.25, 111.24, 32.42, 28.39, 28.29, 23.23, 14.19. MS (ESI-TOF) for $C_{17}H_{19}N_3O_2S$ [M+H]$^+$ calculated 330.1271; found, 330.1248.

N-Methyl-4-(2-pentyl-1H-benzo[d]imidazol-1-yl)thiophene-2-carboxamide (11c). To a stirred solution of 6e (34.25 mg, 0.1 mmol) in methanol (2 mL) was added methylamine solution (2 M in MeOH, 250 μL) and heated at 60° C. for 12 h. The solvent was removed under reduced pressure and the residue was purified by flash chromatography (5% MeOH/DCM) to obtain the compound 11c as white solid (20 mg, 61%). $^1$H NMR (500 MHz, Methanol-d$_4$) δ 7.93 (s, 1H), 7.79-7.71 (m, 1H), 7.64 (d, J=7.4 Hz, 1H), 7.34-7.16 (m, 3H), 2.93 (s, 3H), 2.87 (t, J=7.7 Hz, 2H), 1.81-1.67 (m, 2H), 1.39-1.24 (m, 4H), 0.86 (t, J=6.7 Hz, 3H). $^{13}$C NMR (126 MHz, MeOD) δ 163.77, 157.01, 142.71, 141.68, 137.29, 134.55, 128.40, 127.13, 124.42, 124.06, 119.25, 111.25, 32.42, 28.38, 28.29, 26.80, 23.22, 14.18. MS (ESI-TOF) for $C_{18}H_{21}N_3OS$ [M+H]$^+$ calculated 328.1478; found, 328.1468.

Compound 12 was synthesized similarly as compound 3f.

4-(2-Pentyl-1H-benzo[d]imidazol-1-yl)thiophene-2-carbonitrile (12). 4-Bromothiophene-2-carbonitrile (94.03 mg, 0.5 mmol) was used as reagents. Pale yellow solid (52 mg, 35%). $^1$H NMR (500 MHz, Methanol-d$_4$) δ 8.20 (s, 1H), 8.04 (s, 1H), 7.65 (d, J=7.1 Hz, 1H), 7.35-7.24 (m, 2H), 7.21 (d, J=7.2 Hz, 1H), 2.85 (t, J=7.7 Hz, 2H), 1.74 (p, J=7.3 Hz, 2H), 1.37-1.27 (m, 4H), 0.88 (t, J=6.8 Hz, 3H). $^{13}$C NMR (126 MHz, MeOD) δ 156.97, 142.76, 137.22, 137.21, 135.01, 131.53, 124.63, 124.24, 119.37, 114.13, 112.46, 111.11, 32.42, 28.30, 28.28, 23.25, 14.18. MS (ESI-TOF) for $C_{17}H_{17}N_3S$ [M+H]$^+$ calculated 296.1216; found, 296.1208.

(4-(2-Pentyl-1H-benzo[d]imidazol-1-yl)thiophen-2-yl)methanamine (13a). To a stirred solution of compound 12 (29.54 mg, 0.1 mmol) in anhydrous THF (2 mL) was added LiAlH$_4$ (0.2 mL, 0.2 mmol, 1.0 M in THF) at 0° C. under nitrogen atmosphere. The reaction mixture was stirred for 30 min at room temperature, then 2 h at 80° C. The reaction mixture was cooled to room temperature and quenched carefully with ice-cold water. The resulting mixture was basified with 10% NaOH (to pH=8.0) and extracted with ethyl acetate (3×10 mL). The combined organic layer was dried over Na$_2$SO$_4$ and concentrated under reduced pressure, and the crude material was purified by flash chromatography (10% MeOH/DCM) to obtain the compound 13a as brown solid (14 mg, 47%). $^1$H NMR (500 MHz, Methanol-d$_4$) δ 7.62 (d, J=7.6 Hz, 1H), 7.54 (s, 1H), 7.29-7.17 (m, 3H), 7.12 (s, 1H), 4.05 (s, 2H), 2.86 (t, J=7.7 Hz, 2H), 1.80-1.69 (m, 2H), 1.40-1.19 (m, 4H), 0.87 (t, J=5.4 Hz, 3H). $^{13}$C NMR (126 MHz, MeOD) δ 157.08, 149.41, 142.70, 137.42, 133.95, 124.14, 123.81, 123.80, 122.11, 119.10, 111.42, 41.69, 32.48, 28.45, 28.32, 23.25, 14.22. MS (ESI-TOF) for $C_{17}H_{21}N_3S$ [M+H]$^+$ calculated 300.1529; found, 300.1513.

Compound 13b was synthesized similarly as compound 2a.

4-(2-Pentyl-1H-benzo[d]imidazol-1-yl)thiophene-2-carboximidamide (13b). Compound 12 (29.54 mg, 0.1 mmol) was used as reagent. White solid (22 mg, 70%). $^1$H NMR (500 MHz, Methanol-d$_4$) δ 8.33 (s, 1H), 8.10 (s, 1H), 7.66 (d, J=7.4 Hz, 1H), 7.37-7.19 (m, 3H), 2.89 (t, J=7.7 Hz, 2H), 1.82-1.70 (m, 2H), 1.42-1.23 (m, 4H), 0.88 (t, J=6.6 Hz, 3H). $^{13}$C NMR (126 MHz, MeOD) δ 160.96, 156.94, 142.78, 137.17, 135.64, 132.73, 131.57, 131.41, 124.63, 124.31, 119.42, 111.16, 32.45, 28.32, 28.30, 23.27, 14.21. MS (ESI-TOF) for $C_{17}H_{20}N_4S$ [M+H]$^+$ calculated 313.1481; found, 313.1446.

Compound 13c was synthesized similarly as compound 4b.

N-Hydroxy-4-(2-pentyl-1H-benzo[d]imidazol-1-yl)thiophene-2-carboximidamide (13c). Compound 112 (29.54 mg, 0.1 mmol) was used as reagent. White solid (22 mg, 67%). $^1$H NMR (500 MHz, Methanol-d$_4$) δ 7.71-7.60 (m, 2H), 7.55-7.48 (m, 1H), 7.32-7.19 (m, 3H), 2.88 (t, J=7.7 Hz, 2H), 1.81-1.67 (m, 2H), 1.36-1.23 (m, 4H), 0.87 (t, J=6.8 Hz, 3H). $^{13}$C NMR (126 MHz, MeOD) δ 157.08, 149.95, 142.70, 138.56, 137.35, 134.10, 124.59, 124.31, 124.30, 123.93, 119.15, 111.38, 32.45, 28.42, 28.31, 23.24, 14.20. MS (ESI-TOF) for $C_{17}H_{20}N_4OS$ [M+H]$^+$ calculated 329.1431; found, 329.1411.

Compound 14 was synthesized similarly as compound 12.

4-(2-Pentyl-1H-benzo[d]imidazol-1-yl)thiazole-2-carboxamide (14). 4-Bromothiazole-2-carboxamide (103.52 mg, 0.5 mmol) was used as reagent. White solid (41 mg, 26%). $^1$H NMR (500 MHz, Methanol-d$_4$) δ 8.35 (s, 1H), 7.80 (d, J=7.7 Hz, 1H), 7.61-7.48 (m, 3H), 3.23-3.10 (m, 2H), 1.81 (p, J=7.5 Hz, 2H), 1.42-1.31 (m, 4H), 0.89 (t, J=6.9 Hz, 3H). $^{13}$C NMR (126 MHz, MeOD) δ 165.76, 162.45, 157.09, 156.25, 143.41, 135.02, 127.05, 126.98, 124.18, 116.64, 113.29, 32.25, 27.65, 27.57, 23.11, 14.10. MS (ESI-TOF) for $C_{16}H_{18}N_4OS$ [M+H]$^+$ calculated 315.1274; found, 315.1275.

Example 4: General Procedure for the Synthesis of Compounds 15, 16, 17a-b, 18a-b and 19a-b

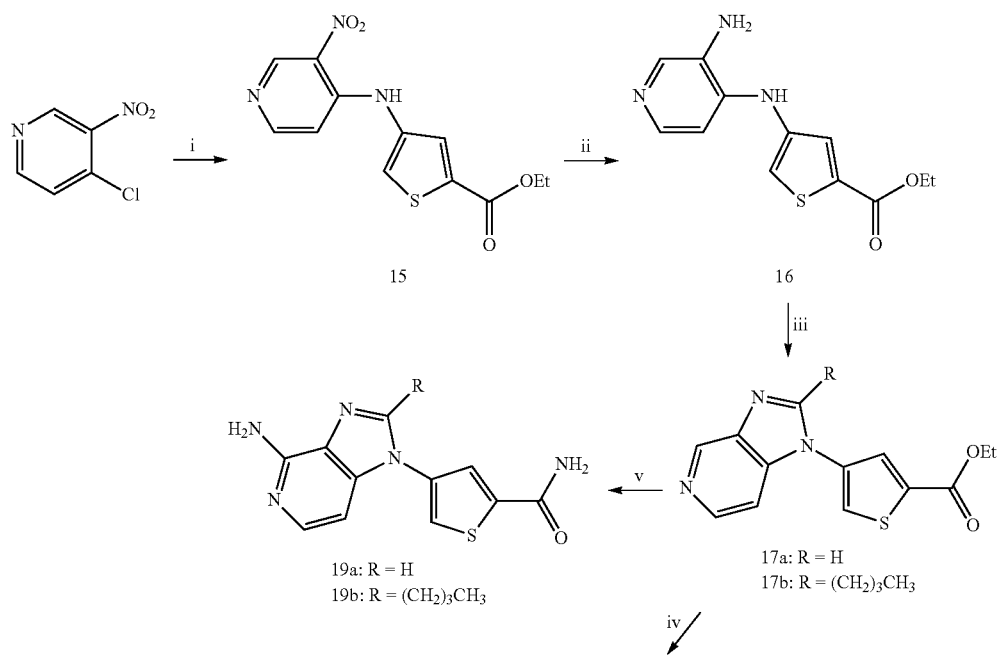

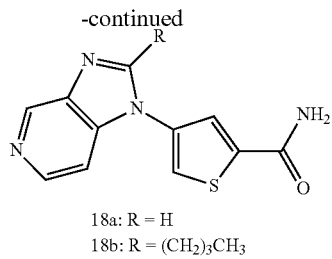

18a: R = H
18b: R = (CH₂)₃CH₃

Reagents and Conditions
(i) Ethyl 4-aminothiophene-2-carboxylate, DIPEA, CH₃CN, 80° C., 2 h;
(ii) H₂, Pd/C, EtOAc, 30 psi, 2 h;
(iii) formamidine acetate salt, 2-methoxyethanol, 120° C., 3 h (for 17a); valeroyl chloride, THF, TEA, 2 h; AcOH, 80° C., 12 h (for 17b);
(iv) 7 N NH₃ in MeOH, 60° C., 12 h;
(v) (a) 3-chloroperoxybenzoic acid, MeOH:DCM:CH3Cl (0.1:1:1), 45° C., 2 h; (b) benzoyl isocyanate, DCM, 45° C., 2 h; (c) 7 N NH3 in MeOH, 60° C., 12 h.

Ethyl 4-((3-nitropyridin-4-yl)amino)thiophene-2-carboxylate (15). To a solution of 4-chloro-3-nitropyridine (317.08 mg, 2 mmol) in acetonitrile (10 mL) were added ethyl 4-aminothiophene-2-carboxylate (342.43 mg, 2 mmol) and DIPEA (1045.15 µL, 6 mmol). The reaction mixture was stirred at 80° C. for 2 h. The solvent was removed under reduced pressure, and the residue was purified by flash chromatography (20% EtOAc/hexanes) to obtain the compound 15 as orange solid (422 mg, 72%). MS (ESI-TOF) for $C_{12}H_{11}N_3O_4S$ [M+H]⁺ calculated 294.0543; found, 394.0539.

Ethyl 4-((3-aminopyridin-4-yl)amino)thiophene-2-carboxylate (16). To a solution of compound 15 (410.62 mg, 1.4 mmol) in anhydrous EtOAc (30 mL) was added catalytic amount of Pd/C, and the reaction mixture was subjected to hydrogenation at 30 psi for 2 h. The reaction mixture was filtered and the filtrate was concentrated under reduced pressure. The crude product was purified by flash chromatography (10% MeOH/DCM) to obtain the compound 16 as a white solid (350 mg, 95%). ¹H NMR (500 MHz, Methanol-d₄) δ 7.87 (s, 1H), 7.72 (d, J=5.3 Hz, 1H), 7.68 (s, 1H), 7.27 (s, 1H), 6.95 (d, J=5.4 Hz, 1H), 4.34 (q, J=7.0 Hz, 2H), 1.37 (t, J=7.1 Hz, 3H). ¹³C NMR (126 MHz, MeOD) δ 163.37, 141.39, 141.14, 140.74, 136.48, 134.17, 133.50, 129.82, 118.23, 108.60, 62.48, 14.58. MS (ESI-TOF) for $C_{12}H_{13}N_3O_2S$ [M+H]⁺ calculated 264.0801; found, 264.0815.

Ethyl 4-(1H-imidazo[4,5-c]pyridin-1-yl)thiophene-2-carboxylate (17a). To a solution of compound 16 (263.31 mg, 1 mmol) in anhydrous 2-methoxyethanol (5 mL) was added formamidine acetate salt (208.22 mg, 2 mmol), and the reaction mixture was stirred at 120° C. for 3 h. The solvent was removed under reduced pressure, and the crude product was purified by flash chromatography (5% MeOH/DCM) to obtain the compound 17a as a white solid (251 mg, 92%). ¹H NMR (500 MHz, Methanol-d₄) δ 9.03 (s, 1H), 8.68 (s, 1H), 8.47 (d, J=5.6 Hz, 1H), 8.15 (s, 2H), 7.76 (d, J=5.4 Hz, 1H), 4.41 (q, J=7.0 Hz, 2H), 1.40 (t, J=7.0 Hz, 3H). ¹³C NMR (126 MHz, MeOD) δ 162.60, 146.48, 143.84, 143.02, 141.56, 139.98, 136.60, 134.58, 129.25, 125.85, 108.04, 62.96, 14.56. MS (ESI-TOF) for $C_{13}H_{11}N_3O_2S$ [M+H]⁺ calculated 274.0645; found, 274.0640.

Compound 17b was synthesized similarly as compound 6a. Ethyl 4-(2-butyl-1H-imidazo[4,5-c]pyridin-1-yl)thiophene-2-carboxylate (17b). N-Acyl intermediate. Compound 16 (263.31 mg, 1 mmol) and valeroyl chloride (142.42 µL, mmol) were used as reagents. White solid (306 mg, 88%). MS (ESI-TOF) for $C_{17}H_{21}N_3O_3S$ [M+H]⁺ calculated 348.1376; found, 348.1358.

Compound 17b. N-Acyl intermediate (173.72 mg, 0.5 mmol) was used as reagent. White solid (140 mg, 85%). ¹H NMR (500 MHz, Methanol-d₄) δ 8.89 (s, 1H), 8.34 (d, J=5.6 Hz, 1H), 8.17-8.10 (m, 1H), 7.97 (s, 1H), 7.33 (d, J=5.6 Hz, 1H), 4.41 (q, J=7.1 Hz, 2H), 2.91 (t, J=7.7 Hz, 2H), 1.77 (p, J=7.6 Hz, 2H), 1.44-1.31 (m, 5H), 0.91 (t, J=7.4 Hz, 3H). ¹³C NMR (126 MHz, MeOD) δ 162.54, 159.91, 143.14, 142.88, 141.30, 140.42, 136.74, 133.62, 131.86, 131.26, 107.40, 62.99, 30.40, 28.09, 23.28, 14.55, 13.94. MS (ESI-TOF) for $C_{17}H_{19}N_3O_2S$ [M+H]⁺ calculated 330.1271; found, 330.1262.

Compounds 18a-b were synthesized similarly as compound 2a.

4-(1H-Imidazo[4,5-c]pyridin-1-yl)thiophene-2-carboxamide (18a). Compound 17a (27.33 mg, 0.1 mmol) was used as reagent. White solid (23 mg, 94%). ¹H NMR (500 MHz, Methanol-d₄) δ 9.04 (s, 1H), 8.65 (s, 1H), 8.48 (d, J=5.8 Hz, 1H), 8.07 (d, J=3.9 Hz, 2H), 7.80 (d, J=5.7 Hz, 1H). ¹³C NMR (126 MHz, MeOD) δ 165.20, 146.49, 143.68, 142.95, 141.94, 141.55, 140.03, 134.21, 125.29, 124.38, 108.13. MS (ESI-TOF) for $C_{11}H_8N_4OS$ [M+H]⁺ calculated 245.0492; found, 245.0490.

4-(2-Butyl-1H-imidazo[4,5-c]pyridin-1-yl)thiophene-2-carboxamide (18b). Compound 17b (32.94 mg, 0.1 mmol) was used as reagent. White solid (29 mg, 97%). ¹H NMR (500 MHz, Methanol-d₄) δ 8.90 (s, 1H), 8.35 (d, J=5.6 Hz, 1H), 8.06 (s, 1H), 7.86 (s, 1H), 7.36 (d, J=5.6 Hz, 1H), 2.93 (t, J=7.7 Hz, 2H), 1.77 (p, J=7.6 Hz, 2H), 1.39 (h, J=7.4 Hz, 2H), 0.91 (t, J=7.4 Hz, 3H). ¹³C NMR (126 MHz, MeOD) δ 165.10, 159.90, 143.14, 142.82, 142.04, 141.32, 140.38, 133.22, 129.62, 127.75, 107.46, 30.42, 28.10, 23.29, 13.95. MS (ESI-TOF) for $C_{15}H_{16}N_4OS$ [M+H]⁺ calculated 301.1118; found, 301.1110.

4-(4-Amino-1H-imidazo[4,5-c]pyridin-1-yl)thiophene-2-carboxamide (19a). To a solution of compound 17a (81.99 mg, 0.3 mmol) in a mixture of solvents CH₃OH/CH₂Cl₂/CHCl₃ (0.1:1:1) was added 3-chloroperoxybenzoic acid (103.54 mg, 0.6 mmol), and the reaction mixture was stirred at 45° C. for 2 h. The solvent was removed under reduced pressure, and the residue was purified by flash chromatography (5% MeOH/DCM) to obtain the N-oxide intermediate as a white solid (84 mg, 97%). MS (ESI-TOF) for $C_{13}H_{11}N_3O_3S$ [M+H]⁺ calculated 290.0594; found, 290.0589. To a solution of N-oxide intermediate (72.33 mg, 0.25 mmol) in anhydrous DCM (5 mL) was added benzoyl isocyanate (55.17 mg, 0.375 mmol), and the reaction mixture was stirred at 45° C. for 2 h. The solvent was removed under reduced pressure, and the residue was purified by flash chromatography (5% MeOH/DCM) to obtain the N-benzoyl intermediate as a white solid (80 mg, 82%). MS (ESI-TOF) for $C_{20}H_{16}N_4O_3S$ [M+H]$^+$ calculated 393.1016; found, 393.1029. The N-benzoyl intermediate (39.24 mg, 0.1 mmol) was dissolved in 7N ammonia in methanol (1 mL) and heated in a sealed vial at 60° C. for 12 h. The solvent was removed under reduced pressure and the crude material was purified by flash chromatography (10% MeOH/DCM) to obtain the desired compound 19a as white solid (24 mg, 93%). $^1$H NMR (500 MHz, DMSO-d$_6$) δ 8.42 (s, 1H), 8.17 (s, 1H), 8.14 (s, 1H), 8.09 (s, 1H), 7.79 (d, J=5.8 Hz, 1H), 7.63 (s, 1H), 6.93 (d, J=5.8 Hz, 1H), 6.35 (s, 2H). $^{13}$C NMR (126 MHz, DMSO-d$_6$) δ 162.07, 152.68, 141.82, 141.09, 140.40, 137.21, 133.72, 126.31, 123.30, 120.97, 96.64. MS (ESI-TOF) for $C_{11}H_9N_5OS$ [M+H]$^+$ calculated 260.0601; found, 260.0593.

Compound 19b was synthesized similarly as compound 19a. 4-(4-Amino-2-butyl-1H-imidazo[4,5-c]pyridin-1-yl)thiophene-2-carboxamide (19b). N-Oxide intermediate. Compound 17b (98.83 mg, 0.3 mmol) was used as reagent. White solid (98 mg, 95%). MS (ESI-TOF) for $C_{17}H_{19}N_3O_3S$ [M+H]$^+$ calculated 346.1220; found, 346.1241. N-Benzoyl intermediate. N-Oxide intermediate (86.35 mg, 0.25 mmol) was used as reagent. White solid (93 mg, 83%). MS (ESI-TOF) for $C_{24}H_{24}N_4O_3S$ [M+H]$^+$ calculated 449.1642; found, 449.1629.

Compound 19b. N-Benzoyl intermediate (44.85 mg, 0.1 mmol) was used as reagent. White solid (28 mg, 89%). $^1$H NMR (500 MHz, Methanol-d$_4$) δ 7.98 (s, 1H), 7.82 (s, 1H), 7.69 (d, J=5.9 Hz, 1H), 6.58 (d, J=5.9 Hz, 1H), 2.86 (t, J=7.7 Hz, 2H), 1.74 (p, J=7.6 Hz, 2H), 1.38 (h, J=7.4 Hz, 2H), 0.91 (t, J=7.4 Hz, 3H). $^{13}$C NMR (126 MHz, MeOD) δ 165.17, 155.70, 152.49, 142.54, 141.75, 141.24, 133.96, 129.22, 127.85, 126.09, 98.40, 30.64, 27.99, 23.28, 13.99. MS (ESI-TOF) for $C_{15}H_{17}N_5OS$ [M+H]$^+$ calculated 316.1227; found, 316.1225.

The biological activity of compounds of the invention can be evaluated using the following assays Example 5: High-throughput screens in porcine blood: Curated compound collections were obtained from the Institute for Therapeutics Discovery & Development at the University of Minnesota. Compound transfers from source (80 nL of 10 mM stocks) to assay plates were performed using an Echo 550 acoustic liquid handler (Labcyte, Sunnyvale, Calif.). For most libraries, a target final concentration of 10 μM of compound (in a final volume of 80 μL for the assay described below) was achieved. Compound plates were hermetically sealed and stored at −80° C. until used. Fresh, heparin-anticoagulated porcine blood from healthy animals were obtained under USDA supervision from Midwest Research Swine, LLC (Glencoe, Minn.). 80 μL of hematocrit-enriched porcine blood (low-speed centrifugation, followed by resuspension in DMEM supplemented with 10% fetal bovine serum) was added to compound plates and incubated for 15 h. The following day, the plates were briefly centrifuged (100 g, 10 min), and supernatants were transferred using an automated ViaFlow 384 transfer device (Integra Biosciences Corp., Hudson, N.H.) to assay plates containing of 10$^6$ cells/mL of each of the following NF-κB/ secreted alkaline phosphatase reporter cells suspended in HEK-Blue Detection Media: human IFN-α/β, human IFN-γ, human TNF-α/IL-1β (InvivoGen, San Diego, Calif.). NF-κB translocation was assayed spectrophotometrically using an alkaline phosphatase-specific chromogen (present in HEK-detection medium as supplied by InvivoGen) at 620 nm using a SpectraMax M4 multimode microplate reader (Molecular Devices, Sunnyvale, Calif.). Z' factors were computed for each TLR/NOD-specific signals. Hits were defined as signals >4σ (in-plate standard deviations for test compounds above negative control means), were deconvoluted in full dose-response assays in human TLR-2/-3/-4/-5/-7/-8/-9 and NOD-1/NOD-2-specific reporter cells in liquid handler-assisted assay formats as described previously.

Example 6: Murine knockout cell-lines: The following reagents were obtained through BEI Resources, NIAID, NIH: the microglial cell line derived from MAL/MyD88 double knockout Mice (NR-9904), and the macrophage cell line derived from TRIF/TRAM knockout mice (NR-9568).

Example 7: Human NOD1/2-specific reporter gene assays (NF-κB induction), and TLR-2/-3/-4/-5/-7/-8/-9/STING/ ISG counter-screens: The induction of NF-κB was quantified using human TLR-2/-3/-4/-5/-7/-8/-9/NOD-1/NOD-2/ STING/ISG-specific, rapid-throughput, liquid handler-assisted reporter gene assays as previously described by us (Wu, W. et al. *J. Med. Chem.* 2010, 53, 3198-3213; Shukla, N. M. et al. *J. Med. Chem.* 2010, 53, 4450-4465; Agnihotri, G. et al. *J. Med. Chem.* 2011, 54, 1490-1510 and Ukani, R. et al. *Bioorg. Med. Chem. Lett.* 2012, 22, 293-295). HEK293 cells stably co-transfected with the appropriate hTLR and secreted alkaline phosphatase (sAP) were maintained in HEK-Blue™ Selection medium. Stable expression of secreted alkaline phosphatase (sAP) under control of NF-κB/AP-1/IRF promoters is inducible by appropriate innate immune stimuli, and extracellular sAP in the supernatant is proportional to NF-κB/IRF induction. Reporter cells were incubated at a density of ~10$^5$ cells/ml in a volume of 80 μl/well, in 384-well, flat-bottomed, cell culture-treated microtiter plates in the presence of graded concentrations of stimuli. sAP was assayed spectrophotometrically using an alkaline phosphatase-specific chromogen (present in HEK-detection medium as supplied by InvivoGen) at 620 nm.

Example 8: Multiplexed immunoassays for human cytokines: Fresh human peripheral blood mononuclear cells (hPBMC) were isolated from human blood obtained by venipuncture in Cell Preparation Tubes (CPT, Beckton-Dickinson) with informed consent and as per guidelines approved by the University of Minnesota Human Subjects Experimentation Committee. Aliquots of PBMCs or THP-1 cells (10$^5$ cells in 100 μL/well) were stimulated for 16 h with graded concentrations of test compounds. Supernatants were isolated by centrifugation, and were assayed in duplicates using analyte-specific multiplexed cytokine/chemokine bead array assays (HCYTMAG-60K-PX41 MILLIPLEX MAP Human Cytokine/Chemokine Magnetic Bead Panel, EMD Millipore, Billerica, Mass.) as reported previously (Beesu, M. et al. *J. Med. Chem.* 2016, 59, 3311-3330). The following analytes were quantified: sCD40L, VEGF, TNF-β, TNF-α, TGF-α, RANTES, PDGF-AB/BB, PDGF-AA, MIP-1β, MIP-1α, MDC (CCL22), MCP-3, MCP-1, IP-10, IL-17A, IL-15, IL-13, IL-12 (p70), IL-12 (p40), IL-10, IL-9, IL-8, IL-7, IL-6, IL-5, IL-4, IL-3, IL-2, IL-1ra, IL-1β, IL-1α, IFN-γ, IFN-α2, GRO, GM-CSF, G-CSF, fractalkine, Flt-3 ligand, FGF-2, eotaxin, EGF.

Example 9: Multiplexed immunoassays for murine cytokines: Supernatants from were isolated by centrifugation, and were assayed in duplicates using analyte-specific multiplexed cytokine/chemokine bead array assays (MCY-TOMAG-70K Cytokine/Chemokine Murine Magnetic Bead Panel, EMD Millipore, Billerica, Mass.) as reported by us previously. The following analytes were quantified: G-CSF, GM-CSF, IFN-γ, IL-1α, IL-1β, IL-2, IL-3, IL-4, IL-5, IL-6, IL-7, IL-9, IL-10, IL-12 (p40), IL-12 (p70), IL-13, IL-15, IL-17, IP-10, KC, LIF, LIX, MCP-1, M-CSF, MIG, MIP-1α, MIP-1β, MIP-2, RANTES, TNF-α, VEGF, Eotaxin/CCL11.

Example 10. The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound having formula Ia or formula Ib:

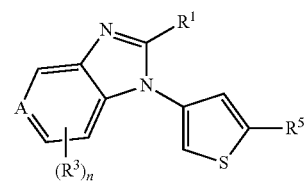

(Ia)

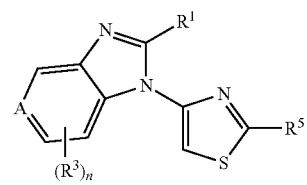

(Ib)

or a salt thereof, wherein
A is CH or N,
$R^1$ is selected from the group consisting of $C_1$-$C_{20}$ alkyl, and $C_2$-$C_{20}$ alkenyl,
each $R^3$ is independently selected from the group consisting of F, Cl, —CN, —NR$^a$R$^b$, —NO$_2$, —OR$^a$, and —($C_1$-$C_6$ alkyl)-NR$^a$R$^b$,
$R^5$ is selected from the group consisting of —CN, —C(=NH)NH(OH), —C(=NH)NH$_2$, —C(=O)NR$^a$R$^b$, —C(=O)NR$^a$—NR$^a$R$^b$, —C(=O)NH($C_1$-$C_6$ alkyl)-NR$^a$R$^b$, and —($C_1$-$C_6$ alkyl)-NR$^a$R$^b$;
$R^a$ and $R^b$ are independently selected from H, OH, phenyl, benzyl, 5-6 membered ring, and $C_1$-$C_6$ alkyl, where phenyl, benzyl or 5-6 membered ring is optionally substituted with one or more groups independently selected from the group consisting of F, Cl, —CN, $C_1$-$C_{12}$ alkyl, $C_2$-$C_{12}$ alkenyl, —($C_1$-$C_6$ alkyl)-NR$^a$R$^b$, —C(=NH)NH(OH), —C(=NH)NH$_2$, —C(=O)NR$^a$R$^b$, —C(=O)NR$^a$—NR$^a$R$^b$, —C(=O)NH($C_1$-$C_6$ alkyl)-NR$^a$R$^b$, —C(=O)OR$^a$, —NR$^a$R$^b$, —NO$_2$, —OR$^a$, —OC(=O)R$^a$, —SR$^a$, —S(O)R$^a$, —S(O)$_2$R$^a$, —S(O)$_2$NR$^a$, and —S(O)$_3$H; or
$R^a$ and $R^b$ are taken together to form a 4-6 membered ring heterocycle with N;
each alkyl and alkenyl are optionally and independently substituted with one or more groups independently selected from the group consisting of F, Cl, —CN, —NR$^a$R$^b$, —NO$_2$, and —OR$^a$, —OC(=O)R$^a$, —SR$^a$, —S(O)R$^a$, —S(O)$_2$R$^a$, —S(O)$_2$NR$^a$, and —S(O)$_3$H; and
n is 0, 1, 2, 3.

2. The compound of claim 1 wherein $R^5$ is selected from the group consisting of —$CH_2NH_2$, —$C(=O)NH_2$, —$C(=O)NH(OH)$, —$C(=O)NH(CH_3)$, —$C(=O)NH(C_4H_9)$ and —$C(=NH)NH_2$.

3. The compound of claim 1 having formula Ia, wherein $R^5$ is —$C(=O)NR^aR^b$, wherein $R^a$ is H and $R^b$ is phenyl, pyridinyl or benzyl.

4. The compound of claim 1 having formula Ia, wherein $R^5$ is —$C(=O)NR^a$—$NR^aR^b$, wherein $R^a$ is H and $R^b$ is phenyl.

5. The compound of claim 1 having formula Ia, wherein $R^5$ is —$C(=O)NH(C_1\text{-}C_6\ alkyl)\text{-}NR^aR^b$, wherein $R^a$ and $R^b$ together form piperidinyl, morpholinyl or piperazinyl.

6. The compound of claim 1 wherein $R^1$ is methyl, ethyl, n-propyl, n-butyl, iso-pentyl, n-pentyl, n-hexyl, n-octyl, n-nonyl, n-undecyl, n-tridecyl, n-pentadecyl, n-heptadecyl or iso-pentenyl.

7. The compound of claim 1 wherein A is CH.
8. The compound of claim 1 wherein A is N.
9. The compound of claim 1 wherein n is 0.
10. The compound of claim 1 wherein $R^3$ is —$NH_2$.
11. The compound of claim 1 selected from:

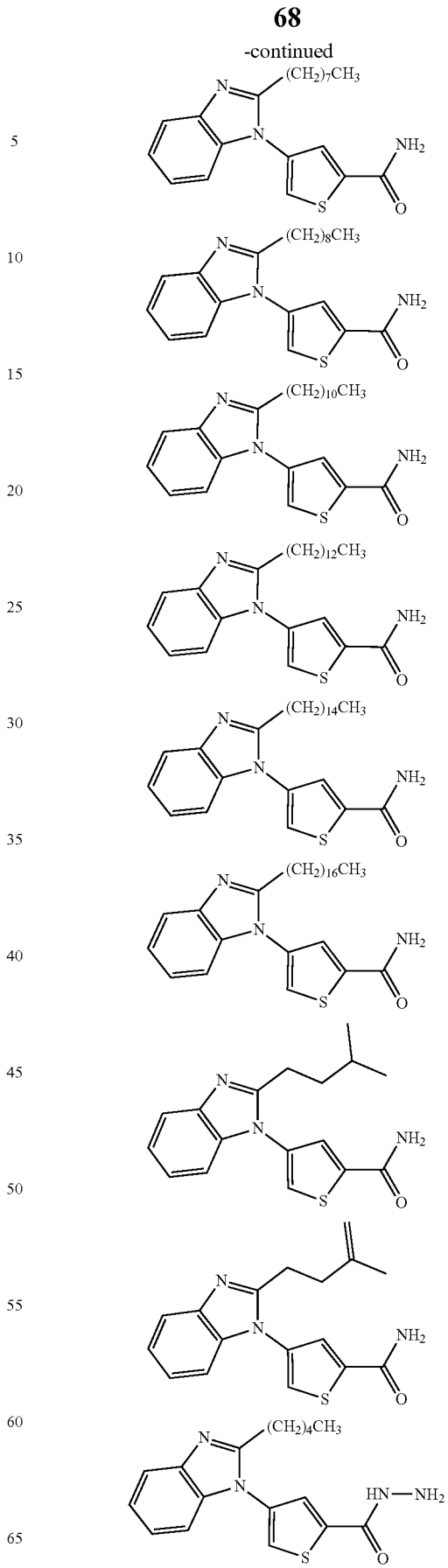

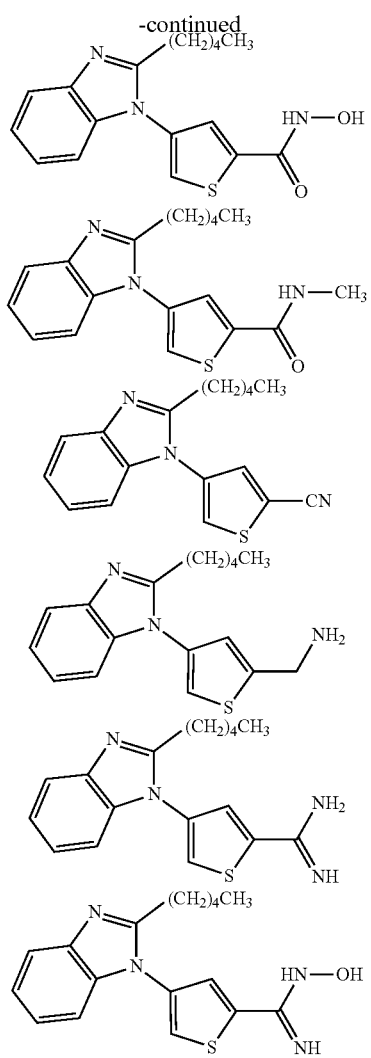

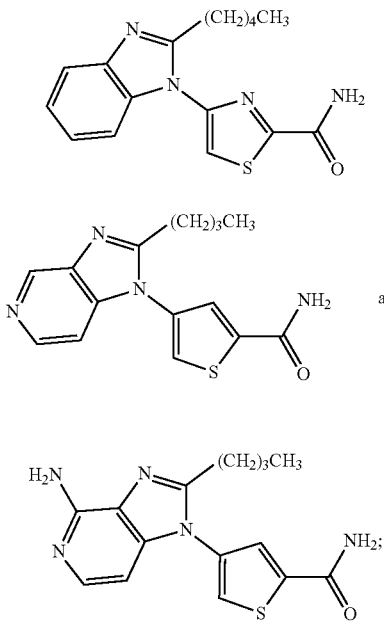

or a salt thereof.

12. The compound of claim 1, wherein the compound stimulates the immune system in the animal comprises, regulates the secretion of cytokines or chemokines in human blood, activates the nucleotide-binding oligomerization domain 2 (NOD2) receptor, or activates the Toll-like receptor (TLR7/8) receptor.

13. A pharmaceutical composition comprising a compound as described in claim 1, or a pharmaceutically acceptable salt thereof, and a pharmaceutically acceptable excipient.

* * * * *